US005990091A

United States Patent [19]

[11] Patent Number: 5,990,091
[45] Date of Patent: Nov. 23, 1999

Tartaglia et al.

[54] VECTORS HAVING ENHANCED EXPRESSION, AND METHODS OF MAKING AND USES THEREOF

[75] Inventors: James Tartaglia, Schenectady; William I. Cox, Sand Lake; Russell Robert Gettig, Averill Park; Hector Martinez, Menands; Enzo Paoletti, Delmar; Steven E. Pincus, East Greenbush, all of N.Y.

[73] Assignee: Virogenetics Corporation, Troy, N.Y.

[21] Appl. No.: 08/816,155

[22] Filed: Mar. 12, 1997

[51] Int. Cl.$^6$ .......................... C12N 15/67; C12N 15/86; A61K 48/00

[52] U.S. Cl. .......................... 514/44; 424/93.2; 435/69.1; 435/172.3; 435/320.1

[58] Field of Search .......................... 514/44; 424/93.2; 435/69.1, 172.3, 320.1

[56] References Cited

U.S. PATENT DOCUMENTS

| | | | |
|---|---|---|---|
| 4,738,922 | 4/1988 | Haseltine et al. | 435/69.3 |
| 5,302,517 | 4/1994 | Rhode, III | 435/69.1 |

OTHER PUBLICATIONS

Park et al., Proc. Natl. Acad. Sci. USA 91:4713–4717 (1994).

*Primary Examiner*—Johnny F. Railey, II
*Attorney, Agent, or Firm*—Frommer Lawrence & Haug LLP; William S. Frommer; Thomas J. Kowalski

[57] ABSTRACT

Disclosed and claimed are vectors having enhanced expression and methods for making and using them. Enhancement of expression is from substantially co-temporal expression of at least one first nucleic acid molecule and at least one second nucleic acid molecule. The second nucleic acid molecule encodes a transcription factor or a translation factor or a transcription factor and a translation factor. The contemporaneous expression can be from operably linking the first and second nucleic molecules to a single promoter, or from operably linking the first nucleic acid molecule to a first promoter and the second nucleic molecule to a second promoter wherein the first and second promoters function substantially contemporaneously. Thus, the first and second nucleic acid molecules can be at the same locus in the vector, or at different loci. The second nucleic acid molecule can encode: one transcription factor or more than one transcription factor; or one translation factor or more than one translation factor; or at least one transcription factor and at least one translation factor. The transcription factor can be from vaccinia H4L, D6, A7, G8R, A1L, A2L, H5R, or combinations thereof. The translation factor can be from a K3L open reading frame, an E3L open reading frame, a VAI RNA, an EBER RNA, a sigma 3 open reading frame, a TRBP open reading frame, or combinations thereof. The vector can be a poxvirus such as an attenuated poxvirus, e.g., NYVAC, or ALVAC.

51 Claims, 30 Drawing Sheets

FIG. 1A

Nucleotide sequence of the insert in vP1380 containing the mutagenized H4L orf and lacZ orf under the H6 promoter.

| Characteristic | Position(s) |
|---|---|
| Left arm | 1-798 |
| Right arm | 6636-7319 |
| H6 promoter | C3307-3184 and C6495-6372 |
| H4L orf | C3183-799 |
| T to C mutations | C2836 and C2839 |
| lacZ orf | C6371-3327 |

```
   1 GGATCCTGCC GTTCCTATTC TAGACCAAAA ATTCGGTTTC ATGTTTTCGA AGCGGTGTTC
  61 TGCAACAAGT CGGGGATCGT GTTCTACATA TTTGGCGGCA TTATCCAGTA TCTGCCTATT
 121 GATCTTCATT TCGTTTTCGA TTCTGGCTAT TTCAAAATAA AATCCCGATG ATAGACCTCC
 181 AGACTTTATA ATTTCATCTA CGATGTTCAG CGCCGTAGTA ACTCTAATAA TATAGGCTGA
 241 TAAGCTAACA TCATACCCTC CTGTATATGT GAATATGGTA TGATTTTTGT CCATTACAAG
 301 CTCGGTTTTA ACTTTATTGC CTGTAATAAT TTCTCTCATC TGTAGGATAT CTATTTTTTT
 361 GTCATGCATT GCCTTCAAGA CGGGACGAAG AAACGTAATA TCCTCAATAA CGTTATCGTT
 421 TTCTACAATA ACTACATATT CTACCTTTTT ATTTTCTAAC TCGGTAAAAA AATTAGAATC
 481 CCATAGGGCT AAATGTCTAG CGATATTTCT TTTCGTTTCC TCTGTACACA TAGTGTTACA
 541 AAACCCTGAA AAGAAGTGAG TATACTTGTC ATCATTTCTA ATGTTTCCTC CAGTCCACTG
 601 TATAAACGCA TAATCCTTGT AATGATCTGG ATCATCCTTG ACTACCACAA CATTTCTTTT
 661 TTCTGGCATA ACTTCGTTGT CCTTTACATC ATCGAACTTC TGATCATTAA TATGCTCATG
 721 AACATTAGGA AATGTTTCTG ATGGAGGTCT ATCAATAACT GGCACAACAA TAACAGGAGT
 781 TTTCACCGCC GCCATTTAGT TATTGAAATT AATCATATAC AACTCTTTAA TACGAGTTAT
 841 ATTTTCGTCT ATCCATTGTT TCACATTTAC ATATTTCGAC AAAAAGATAT AAAATGCGTA
 901 TTCCAATGCT TCTCTGTTTA ATGAATTACT AAAATATACA AACACGTCAC TGTCTGGCAA
 961 TAAATGATAT CTTAGAATAT TGTAACAATT TATTTTGTAT TGCACATGTT CGTGATCTAT
1021 GAGTTCTTCT TCGAATGGCA TAGGATCTCC GAATCTGAAA ACGTATAAAT AGGAGTTAGA
1081 ATAATAATAT TTGAGAGTAT TGGTAATATA TAAACTCTTT AGCGGTATAA TTAGTTTTTT
1141 TCTCTCAATT TCTATTTTTA GATGTGATGG AAAAATGACT AATTTTGTAG CATTAGTATC
1201 ATGAACTCTA ATCAAAATCT TAATATCTTC GTCACACGTT AGCTCTTTGA AGTTTTTAAG
1261 AGATGCATCA GTTGGTTCTA CAGATGGAGT AGGTGCAACA ATTTTTTGTT CTACACATGT
1321 ATGTACTGGA GCCATTGTTT TAACTATAAT GGTGCTTGTA TCGAAAAACT TTAATGCAGA
1381 TAGCGGAAGC TCTTCGCCGC GACTTTCTAC ATCGTAATTG GGTTCTAACG CCGATCTCTG
1441 AATGGATACT AGTTTTCTAA GTTCTAATGT GATTCTCTGA AAATGTAAAT CCAATTCCTC
1501 CGGCATTATA GATGTGTATA CATCGGTAAA TAAAACTATA GTATCCAACG ATCCCTTCTC
1561 GCAAATTCTA GTCTTAACCA AAAAATCGTA TATAACCACG GAGATGGCGT ATTTAAGAGT
1621 GGATTCTTCT ACCGTTTTGT TCTTGGATGT CATATAGGAA ACTATAAAGT CCGCACTACT
1681 GTTAAGAATG ATTACTAACG CAACTATATA GTTCAAATTA AGCATTTTGG AAACATAAAA
1741 TAACTCTGTA GACGATACTT GACTTTCGAA TAAGTTTGCA GACAAACGAA GAAAGAACAG
1801 ACCTCTCTTA ATTTCAGAAG AAAACTTTTT TTCGTATTCC TGACGTCTAG AGTTTATATC
1861 AATAAGAAAG TTAAGAATTA GTCGGTTAAT GTTGTATTTC ATTACCCAAG TTTGAGATTT
1921 CATAATATTA TCAAAAGACA TGATAATATT AAAGATAAAG CGCTGACTAT GAACGAAATA
1981 GCTATATGGT TCGCTCAAAA ATATAGTCTT GTTAAACGTG GAAACGATAA CTGTATTTTT
2041 AATCACGTCA GCGGCATCTA AATTAAATAT AGGTATATTT ATTCCACACA CTCTACAATA
2101 TGCCACACCA TCTTCATAAT AAATAAATTC GTTAGCAAAA TTATTAATTT TAGTGAAATA
2161 GTTAGCGTCA ACTTTCATAG CTTCCTTCAA TCTAATTTGA TGCTCACACG GTGCGAATTC
2221 TACTCTAACA TCCCTTTTCC ATGCCTCAGG TTCATCGATC TCTATAATAT CTAGTTTTTT
2281 GCGTTTCACA AACACAGGCT CGTCTCTCGC GATGAGATCT GTATAGTAAC TATGTAAATG
2341 ATAACTAGAT AGAAAGATGT AGCTATATAG ATGACGATCC TTTAAGAGAG GTATAATAAC
2401 TTTACCCCAA TCAGATAGAC TGTTGTTATG GTCTTCGGAA AAAGAATTTT TATAAATTTT
```

FIG. 1B

2461 TCCAGTATTT TCCAAATATA CGTACTTAAC ATCTAAAAAA TCCTTAATGA TAATAGGAAT
2521 GGATAATCCG TCTATTTTAT AAAGAAATAC ATATCGCACA TTATACTTTT TTTTGGAAAT
2581 GGGAATACCG ATGTGTCTAC ATAAATATGC AAAGTCTAAA TATTTTTTAG AGAATCTTAG
2641 TTGGTCCAAA TTCTTTTCCA AGTACGGTAA TAGATTTTTC ATATTGAACG GTATCTTCTT
2701 AATCTCTGGT TCTAGTTCCG CATTAAATGA TGAAACTAAG TCACTATTTT TATAACTAAC
2761 GATTACATCA CCTCTAACAT CATCATTTAC CAGAATACTG ATCTTCTTTT GTCGTAAATA
2821 CATGTCTAAT GTGTTGAAGA AAAGATCATA CAAGTTATAC GTCATTTCAT CTGTGGTATT
2881 CTTGTCATTG AAGGATAAAC TCGTACTAAT CTCTTCTTTA ACAGCCTGTT CAAATTTATA
2941 TCCTATATAC GAAAAAATAG CAACCAGTGT TTGATCATCC GCGTCAATAT TCTGTTCTAT
3001 CGTAGTGTAT AACAATCGTA TATCTTCTTC TGTGATAGTC GATACGTTAT AAAGGTTGAT
3061 AACGAAAATA TTTTTATTTC GTGAAATAAA GTCATCGTAG GATTTTGGAC TTATATTCGC
3121 GTCTAGTAGA TATGCTTTTA TTTTTGGAAT GATCTCAATT AGAATAGTCT CTTTAGAGTC
3181 CATTACGATA CAAACTTAAC GGATATCGCG ATAATGAAAT AATTTATGAT TATTTCTCGC
3241 TTTCAATTTA ACACAACCCT CAAGAACCTT TGTATTTATT TTCACTTTTT AAGTATAGAA
3301 TAAAGAAGCT TCCCGGGGGA TCCTTATTTT TGACACCAGA CCAACTGGTA ATGGTAGCGA
3361 CCGGCGCTCA GCTGGAATTC CGCCGATACT GACGGGCTCC AGGAGTCGTC GCCACCAATC
3421 CCCATATGGA AACCGTCGAT ATTCAGCCAT GTGCCTTCTT CCGCGTGCAG CAGATGGCGA
3481 TGGCTGGTTT CCATCAGTTG CTGTTGACTG TAGCGGCTGA TGTTGAACTG GAAGTCGCCG
3541 CGCCACTGGT GTGGGCCATA ATTCAATTCG CGCGTCCCGC AGCGCAGACC GTTTTCGCTC
3601 GGGAAGACGT ACGGGGTATA CATGTCTGAC AATGGCAGAT CCCAGCGGTC AAAACAGGCG
3661 GCAGTAAGGC GGTCGGGATA GTTTTCTTGC GGCCCTAATC CGAGCCAGTT TACCCGCTCT
3721 GCTACCTGCG CCAGCTGGCA GTTCAGGCCA ATCCGCGCCG GATGCGGTGT ATCGCTCGCC
3781 ACTTCAACAT CAACGGTAAT CGCCATTTGA CCACTACCAT CAATCCGGTA GGTTTTCCGG
3841 CTGATAAATA AGGTTTTCCC CTGATGCTGC CACGCGTGAG CGGTCGTAAT CAGCACCGCA
3901 TCAGCAAGTG TATCTGCCGT GCACTGCAAC AACGCTGCTT CGGCCTGGTA ATGGCCCGCC
3961 GCCTTCCAGC GTTCGACCCA GGCGTTAGGG TCAATGCGGG TCGCTTCACT TACGCCAATG
4021 TCGTTATCCA GCGGTGCACG GGTGAACTGA TCGCGCAGCG GCGTCAGCAG TTGTTTTTTA
4081 TCGCCAATCC ACATCTGTGA AAGAAAGCCT GACTGGCGGT TAAATTGCCA ACGCTTATTA
4141 CCCAGCTCGA TGCAAAAATC CATTTCGCTG GTGGTCAGAT GCGGGATGGC GTGGGACGCG
4201 GCGGGGAGCG TCACACTGAG GTTTTCCGCC AGACGCCACT GCTGCCAGGC GCTGATGTGC
4261 CCGGCTTCTG ACCATGCGGT CGCGTTCGGT TGCACTACGC GTACTGTGAG CCAGAGTTGC
4321 CCGGCGCTCT CCGGCTGCGG TAGTTCAGGC AGTTCAATCA ACTGTTTACC TTGTGGAGCG
4381 ACATCCAGAG GCACTTCACC GCTTGCCAGC GGCTTACCAT CCAGCGCCAC CATCCAGTGC
4441 AGGAGCTCGT TATCGCTATG ACGGAACAGG TATTCGCTGG TCACTTCGAT GGTTTGCCCG
4501 GATAAACGGA ACTGGAAAAA CTGCTGCTGG TGTTTTGCTT CCGTCAGCGC TGGATGCGGC
4561 GTGCGGTCGG CAAAGACCAG ACCGTTCATA CAGAACTGGC GATCGTTCGG CGTATCGCCA
4621 AAATCACCGC CGTAAGCCGA CCACGGGTTG CCGTTTTCAT CATATTTAAT CAGCGACTGA
4681 TCCACCCAGT CCCAGACGAA GCCGCCCTGT AAACGGGGAT ACTGACGAAA CGCCTGCCAG
4741 TATTTAGCGA AACCGCCAAG ACTGTTACCC ATCGCGTGGG CGTATTCGCA AAGGATCAGC
4801 GGGCGCGTCT CTCCAGGTAG CGAAAGCCAT TTTTTGATGG ACCATTTCGG CACAGCCGGG
4861 AAGGGCTGGT CTTCATCCAC GCGCGCGTAC ATCGGGCAAA TAATATCGGT GGCCGTGGTG
4921 TCGGCTCCGC CGCCTTCATA CTGCACCGGG CGGGAAGGAT CGACAGATTT GATCCAGCGA
4981 TACAGCGCGT CGTGATTAGC GCCGTGGCCT GATTCATTCC CCAGCGACCA GATGATCACA
5041 CTCGGGTGAT TACGATCGCG CTGCACCATT CGCGTTACGC GTTCGCTCAT CGCCGGTAGC
5101 CAGCGCGGAT CATCGGTCAG ACGATTCATT GGCACCATGC CGTGGGTTTC AATATTGGCT
5161 TCATCCACCA CATACAGGCC GTAGCGGTCG CACAGCGTGT ACCACAGCGG ATGGTTCGGA
5221 TAATGCGAAC AGCGCACGGC GTTAAAGTTG TTCTGCTTCA TCAGCAGGAT ATCCTGCACC
5281 ATCGTCTGCT CATCCATGAC CTGACCATGC AGAGGATGAT GCTCGTGACG GTTAACGCCT
5341 CGAATCAGCA ACGGCTTGCC GTTCAGCAGC AGCAGACCAT TTTCAATCCG CACCTCGCGG
5401 AAACCGACAT CGCAGGCTTC TGCTTCAATC AGCGTGCCGT CGGCGGTGTG CAGTTCAACC
5461 ACCGCACGAT AGAGATTCGG GATTTCGGCG CTCCACAGTT TCGGGTTTTC GACGTTCAGA
5521 CGTAGTGTGA CGCGATCGGC ATAACCACCA CGCTCATCGA TAATTTCACC GCCGAAAGGC
5581 GCGGTGCCGC TGGCGACCTG CGTTTCACCC TGCCATAAAG AAACTGTTAC CCGTAGGTAG
5641 TCACGCAACT CGCCGCACAT CTGAACTTCA GCCTCCAGTA CAGCGCGGCT GAAATCATCA
5701 TTAAAGCGAG TGGCAACATG GAAATCGCTG ATTTGTGTAG TCGGTTTATG CAGCAACGAG
5761 ACGTCACGGA AAATGCCGCT CATCCGCCAC ATATCCTGAT CTTCCAGATA ACTGCCGTCA
5821 CTCCAACGCA GCACCATCAC CGCGAGGCGG TTTTCTCCGG CGCGTAAAAA TGCGCTCAGG
5881 TCAAATTCAG ACGGCAAACG ACTGTCCTGG CCGTAACCGA CCCAGCGCCC GTTGCACCAC
5941 AGATGAAACG CCGAGTTAAC GCCATCAAAA ATAATTCGCG TCTGGCCTTC CTGTAGCCAG
6001 CTTTCATCAA CATTAAATGT GAGCGAGTAA CAACCCGTCG GATTCTCCGT GGGAACAAAC
6061 GGCGGATTGA CCGTAATGGG ATAGGTTACG TTGGTGTAGA TGGGCGCATC GTAACCGTGC
6121 ATCTGCCAGT TTGAGGGGAC GACGACAGTA TCGGCCTCAG GAAGATCGCA CTCCAGCCAG

FIG. 1C

6181 CTTTCCGGCA CCGCTTCTGG TGCCGGAAAC CAGGCAAAGC GCCATTCGCC ATTCAGGCTG

6241 CGCAACTGTT GGGAAGGGCG ATCGGTGCGG GCCTCTTCGC TATTACGCCA GCTGGCGAAA

6301 GGGGGATGTG CTGCAAGGCG ATTAAGTTGG GTAACGCCAG GGTTTTCCCA GTCACGACGT

6361 TGTAAAACCA TTACGATACA AACTTAACGG ATATCGCGAT AATGAAATAA TTTATGATTA

6421 TTTCTCGCTT TCAATTTAAC ACAACCCTCA AGAACCTTTG TATTTATTTT CACTTTTTAA

6481 GTATAGAATA AAGAACCCGG GAAGCTTGTC TAGCTGGTGC TGAGTTTCTA CGTGAGTTGA

6541 TTCGTCTCTT GCGTGCCTCT CGTGATCCAA TTGTCCCGAG ATATTCTCTT CTCTTCCGGT

6601 GCTTCTTATG AAACTTTCCC TGACGGTGGC GTTTTAAAGT TACAAACAAC TAGGAAATTG

6661 GTTTATGATG TATAATTTTT TTAGTTTTTA TAGATTCTTT ATTCTATACT TAAAAAATGA

6721 AAATAAATAC AAAGGTTCTT GAGGGTTGTG TTAAATTGAA AGCGAGAAAT AATCATAAAT

6781 TATTTCATTA TCGCGATATC CGTTAAGTTT GTATCGTAAT GGCGTGGTCA ATTACAAATA

6841 AAGCGGATAC TAGTAGCTTC ACAAAGATGG CTGAAATCAG AGCTCATCTA AAAAATAGCG

6901 CTGAAAATAA AGATAAAAAC GAGGATATTT TCCCGGAAGA TGTAATAATT CCATCTACTA

6961 AGCCCAAAAC CAAACGAGCC ACTACTCCTC GTAAACCAGC GGCTACTAAA AGATCAACCA

7021 AAAAGGAGGA AGTGGAAGAA GAAGTAGTTA TAGAGGAATA TCATCAAACA ACTGAAAAAA

7081 ATTCTCCATC TCCTGGAGTC GGCGACATTG TAGAAAGCGT GGCTGCTGTA GAGCTCGATG

7141 ATAGCGACGG GGATGATGAA CCTATGGTAC AAGTTGAAGC TGGTAAAGTA AATCATAGTG

7201 CTAGAAGCGA TCTTTCTGAC CTAAAGGTGG CTACCGACAA TATCGTTAAA GATCTTAAGA

7261 AAATTATTAC TAGAATCTCT GCAGTATCGA CGGTTCTAGA GGATGTTCAA GCAGGATCC

FIG. 2A

Nucleotide Sequence of the ALVAC C8 Insertion site containing the H6/H4L expression cassette

| Characteristic | Position(s)bp |
|---|---|
| Left Arm | 1-487 |
| Right Arm | 3016-4225 |
| H6 Promoter | 495-618 |
| H4L orf | 619-3003 |

```
   1 GAGCTCACTT ATTACATCCT ACTGACTATA TACAGCGAAT TAACCATAGG CGTAATTGTA
  61 CAGAAACCAG GAAATTATTA CCGCCTTTTA TAAGAAGTAT TAATAAAACA TGTAGCGTAT
 121 GTCTAGAAAG AATATACGAA AAAGAAATAA ATAAACAATA TTTCGGTATT TTACCAAATT
 181 GTAAACACGT GTTTTGTTTT TACTGTATAC AACGTTGGAT GTCTATAATA AAAGGTACGG
 241 ATACCGAAGG TACATGTCCT GTATGTAGAA CAGTTTCTGT ATTTATAGTG CCTAATAGGT
 301 ACTGGATAGA CGATAAATAT GAAAAGAGAT TAATTATAAA TAAATATAAG AATGACAGAA
 361 AGACTTATAA AGCGTTTAAA CATTATATAG GAAGATACGT ATTATTTTAT ACAGTAAACA
 421 ACAGTTTATT TGTTACTAAT GATTAAGGTA CGTGACTAAT TAGCTATAAA AAGGATCCAT
 481 CGATGATGGG AAGCTTCTTT ATTCTATACT TAAAAAGTGA AAATAAATAC AAAGGTTCTT
 541 GAGGGTTGTG TTAAATTGAA AGCGAGAAAT AATCATAAAT TATTTCATTA TCGCGATATC
 601 CGTTAAGTTT GTATCGTAAT GGACTCTAAA GAGACTATTC TAATTGAGAT CATTCCAAAA
 661 ATAAAAGCAT ATCTACTAGA CGCGAATATA AGTCCAAAAT CCTACGATGA CTTTATTTCA
 721 CGAAATAAAA ATATTTTCGT TATCAACCTT TATAACGTAT CGACTATCAC AGAAGAAGAT
 781 ATACGATTGT TATACACTAC GATAGAACAG AATATTGACG CGGATGATCA AACACTGGTT
 841 GCTATTTTTT CGTATATAGG ATATAAATTT GAACAGGCTG TTAAAGAAGA GATTAGTACG
 901 AGTTTATCCT TCAATGACAA GAATACCACA GATGAAATGA CGTATAACTT GTATGATCTT
 961 TTCTTCAACA CATTAGACAT GTATTTACGA CAAAAGAAGA TCAGTATTCT GGTAAATGAT
1021 GATGTTAGAG GTGATGTAAT CGTTAGTTAT AAAAATAGTG ACTTAGTTTC ATCATTTAAT
1081 GCGGAACTAG AACCAGAGAT TAAGAAGATA CCGTTCAATA TGAAAAATCT ATTACCGTAC
1141 TTGGAAAAGA ATTTGGACCA ACTAAGATTC TCTAAAAAAT ATTTAGACTT TGCATATTTA
1201 TGTAGACACA TCGGTATTCC CATTTCCAAA AAAAAGTATA ATGTGCGATA TGTATTTCTT
1261 TATAAAATAG ACGGATTATC CATTCCTATT ATCATTAAGG ATTTTTTAGA TGTTAAGTAC
1321 GTATATTTGG AAAATACTGG AAAAATTTAT AAAAATTCTT TTTCCGAAGA CCATAACAAC
1381 AGTCTATCTG ATTGGGGTAA AGTTATTATA CCTCTCTTAA AGGATCGTCA TCTATATAGC
1441 TACATCTTTC TATCTAGTTA TCATTTACAT AGTTACTATA CAGATCTCAT CGCGAGAGAC
1501 GAGCCTGTGT TTGTGAAACG CAAAAAACTA GATATTATAG AGATCGATGA ACCTGAGGCA
1561 TGGAAAAGGG ATGTTAGAGT AGAATTCGCA CCGTGTGAGC ATCAAATTAG ATTGAAGGAA
1621 GCTATGAAAG TTGACGCTAA CTATTTCACT AAAATTAATA ATTTTGCTAA CGAATTTATT
1681 TATTATGAAG ATGGTGTGGC ATATTGTAGA GTGTGTGGAA TAAATATACC TATATTTAAT
1741 TTAGATGCCG CTGACGTGAT TAAAAATACA GTTATCGTTT CCACGTTTAA CAAGACTATA
1801 TTTTTGAGCG AACCATATAG CTATTTCGTT CATAGTCAGC GCTTTATCTT TAATATTATC
1861 ATGTCTTTTG ATAATATTAT GAAATCTCAA ACTTGGGTAA TGAAATACAA CATTAACCGA
1921 CTAATTCTTA ACTTTCTTAT TGATATAAAC TCTAGACGTC AGGAATACGA AAAAAAGTTT
1981 TCTTCTGAAA TTAAGAGAGG TCTGTTCTTT CTTCGTTTGT CTGCAAACTT ATTCGAAAGT
2041 CAAGTATCGT CTACAGAGTT ATTTTATGTT TCCAAAATGC TTAATTTGAA CTATATAGTT
2101 GCGTTAGTAA TCATTCTTAA CAGTAGTGCG GACTTTATAG TTTCCTATAT GACATCCAAG
2161 AACAAAACGG TAGAAGAATC CACTCTTAAA TACGCCATCT CCGTGGTTAT ATACGATTTT
2221 TTGGTTAAGA CTAGAATTTG CGAGAAGGGA TCGTTGGATA CTATAGTTTT ATTTACCGAT
2281 GTATACACAT CTATAATGCC GGAGGAATTG GATTTACATT TTCAGAGAAT CACATTAGAA
2341 CTTAGAAAAC TAGTATCCAT TCAGAGATCG GCGTTAGAAC CCAATTACGA TGTAGAAAGT
2401 CGCGGCGAAG AGCTTCCGCT ATCTGCATTA AAGTTTTTCG ATACAAGCAC CATTATAGTT
2461 AAAACAATGG CTCCAGTACA TACATGTGTA GAACAAAAAA TTGTTGCACC TACTCCATCT
2521 GTAGAACCAA CTGATGCATC TCTTAAAAAC TTCAAAGAGC TAACGTGTGA CGAAGATATT
2581 AAGATTTTGA TTAGAGTTCA TGATACTAAT GCTACAAAAT TAGTCATTTT TCCATCACAT
2641 CTAAAAATAG AAATTGAGAG AAAAAAACTA ATTATACCGC TAAAGAGTTT ATATATTACC
2701 AATACTCTCA AATATTATTA TTCTAACTCC TATTTATACG TTTTCAGATT CGGAGATCCT
2761 ATGCCATTCG AAGAAGAACT CATAGATCAC GAACATGTGC AATACAAAAT AAATTGTTAC
2821 AATATTCTAA GATATCATTT ATTGCCAGAC AGTGACGTGT TTGTATATTT TAGTAATTCA
2881 TTAAACAGAG AAGCATTGGA ATACGCATTT TATATCTTTT TGTCGAAATA TGTAAATGTG
2941 AAACAATGGA TAGACGAAAA TATAACTCGT ATTAAAGAGT TGTATATGAT TAATTTCAAT
3001 AACTAAAAGC TTCCCATCCT GCAGCTCGAG TTTTTATGAC TAGTTAATCA CGGCCGCTCA
```

FIG. 2B

```
3061 ATATTGTATT GGATGGTTAG AGATCAAAGG ATACAAGATA ACTGGGCTCA TTTCAGCTTT
3121 ACATTCATCC CTATAAGCTT TCATAATGGG ATTTTTCTCC ATAATGTCAA AATCACTTTG
3181 GATATATTCA AAATTTTCTA CAAAATGTTT TGGTTGTTCT GAGCTAAACA CGATGTTAGA
3241 TATTAATAAC TTTGCTATCT CAAGACCTTC TGAAGTATCA ACTTTGATAT TGGAAAGAGG
3301 TGTAAAATAA GGTGATGAAG CGATTGTTGT ATCTGCACAG AATGTTAACA GTATATCTAC
3361 TAATTCTACA TTTCCATCTG TCACAGCATG CCATAGAGGA GTATTCCAGT ACCTGTCCTT
3421 AGCATTTATA TCAGCACCGA ATTCCAAAAG CATAATAGTT ATCTTTACAG ATCCTATACA
3481 CACAGCATAA TGCAAAGGAG TCATCCTATG GCTATCTTTA ACGTTAGTAT ATGCTCCAGC
3541 TAGAAGTAAT TGCTCTATTA TCTCCATGTT TTCAGATTTA ACAGCATAAT GCAATGGATA
3601 CATATATCCT CTGTAACCAT AATTTATACT CGATCCAGCT TTTAGTAACA TACTCACAAT
3661 TTCCAAATTT TCTCTCTTTA TAGCCTCGAT TATGGGATGA TTTTCCCTGT ACTCATTGTC
3721 AACATCAGCG TTATACTCCA GAAGTAACTT TACAATTTCC ACATTCTCTA TAGAGACAGC
3781 ATACTGGAGT GGAGTCTTTA CTTTGTAGTC CTCATATGTA TCCACATTAG CGCCATGATC
3841 CAACAAGAGT TTCACCAGAT CTATGTTCTG AACTTTGACA GCTCTATGCA ACGGAGAAGA
3901 TACTTGTTCG CTAGATATAT CAGGATCAGC TCCTGCTAAC AATAGAGCTT TGGCTATTTC
3961 AAATTTTTCA TTTTCTACAG CACAATGAAG GGGTGAGCAG CCATAATCGT TGAATACGTC
4021 CAGGTTAATG CCGGTTTTCA CAATATCTAG CACGCTAGAC AGAGATCCAG ATTCAATAGC
4081 TTCGAATAAG TATGCCTCCA TTTTGTGTAA TAGTAGTAAG TAATAATTTT CTGAAGAAAC
4141 TACTAACTTA CCGAGCTATA GTAGATAGTT ATAATTTCAT TTTTTTACAA GTAGTATCAC
4201 ATAGTGATTG CTTATTAAAG GTACC
```

FIG. 3A

Nucleotide sequence of the ALVAC C6 insertion site containing the H6 / K3L and E3L expression cassette.

| Characteristic | Position(s) |
|---|---|
| Left Arm | 1-385 |
| Right Arm | 3273-4434 |
| K3L orf | C727-464 |
| H6 Promoter | C850-728 |
| E3L | C2758-2188 |

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAG ATCTCTCGAG
 421 GTCGACGGTA TCGATAAGCT TGATATCGAA TTCATAAAAA TTATTGATGT CTACACATCC
 481 TTTTGTAATT GACATCTATA TATCCTTTTG TATAATCAAC TCTAATCACT TTAACTTTTA
 541 CAGTTTTCCC TACCAGTTTA TCCCTATATT CAACATATCT ATCCATATGC ATCTTAACAC
 601 TCTCTGCCAA GATAGCTTCA GAGTGAGGAT AGTCAAAAAG ATAAATGTAT AGAGCATAAT
 661 CCTTCTCGTA TACTCTGCCC TTTATTACAT CGCCCGCATT GGGCAACGAA TAACAAAATG
 721 CAAGCATACG ATACAAACTT AACGGATATC GCGATAATGA AATAATTTAT GATTATTTCT
 781 CGCTTTCAAT TTAACACAAC CCTCAAGAAC CTTTGTATTT ATTTTCACTT TTTAAGTATA
 841 GAATAAAGAA AGCTCTAATT AATTAATGAA CAGATTGTTT CGTTTTCCCC TTGGCGTATC
 901 ACTAATTAAT TAACCCGGGC TGCAGCTCGA GGAATTCAAC TATATCGACA TATTTCATTT
 961 GTATACACAT AACCATTACT AACGTAGAAT GTATAGGAAG AGATGTAACG GGAACAGGGT
1021 TTGTTGATTC GCAAACTATT CTAATACATA ATTCTTCTGT TAATACGTCT TGCACGTAAT
1081 CTATTATAGA TGCCAAGATA TCTATATAAT TATTTTGTAA GATGATGTTA ACTATGTGAT
1141 CTATATAAGT AGTGTAATAA TTCATGTATT TCGATATATG TTCCAACTCT GTCTTTGTGA
1201 TGTCTAGTTT CGTAATATCT ATAGCATCCT CAAAAAATAT ATTCGCATAT ATTCCCAAGT
1261 CTTCAGTTCT ATCTTCTAAA AAATCTTCAA CGTATGGAAT ATAATAATCT ATTTTACCTC
1321 TTCTGATATC ATTAATGATA TAGTTTTTGA CACTATCTTC TGTCAATTGA TTCTTATTCA
1381 CTATATCTAA GAAACGGATA GCGTCCCTAG GACGAACTAC TGCCATTAAT ATCTCTATTA
1441 TAGCTTCTGG ACATAATTCA TCTATTATAC CAGAATTAAT GGGAACTATT CCGTATCTAT
1501 CTAACATAGT TTTAAGAAAG TCAGAATCTA AGACCTGATG TTCATATATT GGTTCATACA
1561 TGAAATGATC TCTATTGATG ATAGTGACTA TTTCATTCTC TGAAAATTGG TAACTCATTC
1621 TATATATGCT TTCCTTGTTG ATGAAGGATA GAATATACTC AATAGAATTT GTACCAACAA
1681 ACTGTTCTCT TATGAATCGT ATATCATCAT CTGAAATAAT CATGTAAGGC ATACATTTAA
1741 CAATTAGAGA CTTGTCTCCT GTTATCAATA TACTATTCTT GTGATAATTT ATGTGTGAGG
1801 CAAATTTGTC CACGTTCTTT AATTTTGTTA TAGTAGATAT CAAATCCAAT GGAGCTACAG
1861 TTCTTGGCTT AAACAGATAT AGTTTTTCTG GAACAAATTC TACAACATTA TTATAAAGGA
1921 CTTTGGGTAG ATAAGTGGGA TGAAATCCTA TTTTAATTAA TGCTATCGCA TTGTCCTCGT
1981 GCAAATATCC AAACGCTTTT GTGATAGTAT GGCATTCATT GTCTAGAAAC GCTCTACGAA
2041 TATCTGTGAC AGATATCATC TTTAGAGAAT ATACTAGTCG CGTTAATAGT ACTACAATTT
2101 GTATTTTTTA ATCTATCTCA ATAAAAAAAT TAATATGTAT GATTCAATGT ATAACTAAAC
2161 TACTAACTGT TATTGATAAC TAGAATCAGA ATCTAATGAT GACGTAACCA AGAAGTTTAT
2221 CTACTGCCAA TTTAGCTGCA TTATTTTTAG CATCTCGTTT AGATTTTCCA TCTGCCTTAT
2281 CGAATACTCT TCCGTCGATG TCTACACAGG CATAAAATGT AGGAGAGTTA CTAGGCCCAA
2341 CTGATTCAAT ACGAAAAGAC CAATCTCTCT TAGTTATTTG GCAGTACTCA TTAATAATGG
2401 TGACAGGGTT AGCATCTTTC CAATCAATAA TTTTTTTAGC CGGAATAACA TCATCAAAAG
2461 ACTTATGATC CTCTCTCATT GATTTTTCGC GGGATACATC ATCTATTATG ACGTCAGCCA
```

FIG. 3B

```
2521 TAGCATCAGC ATCCGGCTTA TCCGCCTCCG TTGTCATAAA CCAACGAGGA GGAATATCGT
2581 CGGAGCTGTA CACCATAGCA CTACGTTGAA GATCGTACAG AGCTTTATTA ACTTCTCGCT
2641 TCTCCATATT AAGTTGTCTA GTTAGTTGTG CAGCAGTAGC TCCTTCGATT CCAATGTTTT
2701 TAATAGCCGC ACACACAATC TCTGCGTCAG AACGCTCGTC AATATAGATC TTAGACATTT
2761 TTAGAGAGAA CTAACACAAC CAGCAATAAA ACTGAACCTA CTTTATCATT TTTTTATTCA
2821 TCATCCTCTG GTGGTTCGTC GTTTCTATCG AATGTAGCTC TGATTAACCC GTCATCTATA
2881 GGTGATGCTG GTTCTGGAGA TTCTGGAGGA GATGGATTAT TATCTGGAAG AATCTCTGTT
2941 ATTTCCTTGT TTTCATGTAT CGATTGCGTT GTAACATTAA GATTGCGAAA TGCTCTAAAT
3001 TTGGGAGGCT TAAAGTGTTG TTTGCAATCT CTACACGCGT GTCTAACTAG TGGAGGTTCG
3061 TCAGCTGCTC TAGTTTGAAT CATCATCGGC GTAGTATTCC TACTTTTACA GTTAGGACAC
3121 GGTGTATTGT ATTTCTCGTC GAGAACGTTA AAATAATCGT TGTAACTCAC ATCCTTTATT
3181 TTATCTATAT TGTATTCTAC TCCTTTCTTA ATGCATTTTA TACCGAATAA GAGATAGCGA
3241 AGGAATTCTT TTTATTGATT AACTAGTCAA ATGAGTATAT ATAATTGAAA AAGTAAAATA
3301 TAAATCATAT AATAATGAAA CGAAATATCA GTAATAGACA GGAACTGGCA GATTCTTCTT
3361 CTAATGAAGT AAGTACTGCT AAATCTCCAA AATTAGATAA AAATGATACA GCAAATACAG
3421 CTTCATTCAA CGAATTACCT TTTAATTTTT TCAGACACAC CTTATTACAA ACTAACTAAG
3481 TCAGATGATG AGAAAGTAAA TATAAATTTA ACTTATGGGT ATAATATAAT AAAGATTCAT
3541 GATATTAATA ATTTACTTAA CGATGTTAAT AGACTTATTC CATCAACCCC TTCAAACCTT
3601 TCTGGATATT ATAAAATACC AGTTAATGAT ATTAAAATAG ATTGTTTAAG AGATGTAAAT
3661 AATTATTTGG AGGTAAAGGA TATAAAATTA GTCTATCTTT CACATGGAAA TGAATTACCT
3721 AATATTAATA ATTATGATAG GAATTTTTTA GGATTTACAG CTGTTATATG TATCAACAAT
3781 ACAGGCAGAT CTATGGTTAT GGTAAAACAC TGTAACGGGA AGCAGCATTC TATGGTAACT
3841 GGCCTATGTT TAATAGCCAG ATCATTTTAC TCTATAAACA TTTTACCACA AATAATAGGA
3901 TCCTCTAGAT ATTTAATATT ATATCTAACA ACAACAAAAA AATTTAACGA TGTATGGCCA
3961 GAAGTATTTT CTACTAATAA AGATAAAGAT AGTCTATCTT ATCTACAAGA TATGAAAGAA
4021 GATAATCATT TAGTAGTAGC TACTAATATG GAAAGAAATG TATACAAAAA CGTGGAAGCT
4081 TTTATATTAA ATAGCATATT ACTAGAAGAT TTAAAATCTA GACTTAGTAT AACAAAACAG
4141 TTAAATGCCA ATATCGATTC TATATTTCAT CATAACAGTA GTACATTAAT CAGTGATATA
4201 CTGAAACGAT CTACAGACTC AACTATGCAA GGAATAAGCA ATATGCCAAT TATGTCTAAT
4261 ATTTTAACTT TAGAACTAAA ACGTTCTACC AATACTAAAA ATAGGATACG TGATAGGCTG
4321 TTAAAAGCTG CAATAAATAG TAAGGATGTA GAAGAAATAC TTTGTTCTAT ACCTTCGGAG
4381 GAAAGAACTT TAGAACAACT TAAGTTTAAT CAAACTTGTA TTTATGAAGG TACC
```

FIG. 4A

DNA sequence of the coding region of FHV gB with modified T5NT motifs.

```
   1 ATGTCCACTC GTGGCGATCT TGGGAAGCGG CGACGAGGGA GTCGTTGGCA GGGACACAGT
  61 GGCTATTTTC GACAGAGATG TTTTTTCCCT TCTCTACTCG GTATTGCAGC GACTGGCTCC
 121 AGACATGGTA ACGGATCGTC GGGATTAACC AGACTAGCTA GATATGTTTC ATTTATCTGG
 181 ATCGTACTAT TCTTAGTCGG TCCCCGTCCA GTAGAGGGTC AATCTGGAAG CACATCGGAA
 241 CAACCCCGGC GGACTGTAGC TACCCCTGAG GTAGGGGGTA CACCACCAAA ACCAACTACA
 301 GATCCCACCG ATATGTCGGA TATGAGGGAA GCTCTCCGTG CGTCCCAAAT AGAGGCTAAC
 361 GGACCATCGA CTTTCTATAT GTGTCCACCA CCTTCAGGAT CTACTGTCGT GCGTTTAGAG
 421 CCACCACGGG CCTGTCCAGA TTATAAACTA GGGAAAAATT TTACCGAGGG TATAGCTGTA
 481 ATATTTAAAG AAAATATAGC GCCATATAAA TTCAAGGCAA ATATATACTA TAAAAACATT
 541 ATTATGACAA CGGTATGGTC TGGGAGTTCC TATGCCGTTA CAACCAACCG ATATACAGAC
 601 AGGGTTCCCG TGAAAGTTCA AGAGATTACA GATCTCATAG ATAGACGGGG TATGTGCCTC
 661 TCGAAAGCTG ATTACGTTCG TAACAATTAT CAATTTACGG CCTTTGATCG AGACGAGGAT
 721 CCCAGAGAAC TGCCTCTGAA ACCCTCCAAG TTCAACACTC CAGAGTCCCG TGGATGGCAC
 781 ACCACCAATG AAACATACAC AAAGATCGGT GCTGCTGGAT TTCACCACTC TGGGACCTCT
 841 GTAAATTGCA TCGTAGAGGA AGTGGATGCA AGATCTGTAT ATCCATATGA CTCATTTGCT
 901 ATCTCCACTG GTGACGTGAT TCACATGTCT CCATTCTTTG GGCTGAGGGA TGGAGCCCAT
 961 GTAGAACATA CTAGTTATTC TTCAGACAGA TTTCAACAAA TCGAGGGATA CTATCCAATA
1021 GACTTGGATA CGCGATTACA ACTGGGGGCA CCAGTTTCTC GCAATTTTTT GGAAACTCCG
1081 CATGTGACAG TGGCCTGGAA CTGGACCCCA AAGTCTGGTC GGGTATGTAC CTTAGCCAAA
1141 TGGAGGGAAA TAGATGAAAT GCTACGCGAT GAATATCAGG GCTCCTATAG ATTTACAGCC
1201 AAGACCATAT CCGCTACTTT CATCTCCAAT ACTTCACAAT TTGAAATCAA TCGTATCCGT
1261 TTGGGGGACT GTGCCACCAA GGAGGCAGCC GAAGCCATAG ACCGGATTTA TAAGAGTAAA
1321 TATAGTAAAA CTCATATTCA GACTGGAACC CTGGAGACCT ACCTAGCCCG TGGGGGATTT
1381 CTAATAGCTT TCCGTCCCAT GATCAGCAAC GAACTAGCAA AGTTATATAT CAATGAATTA
```

FIG. 4B

```
1441 GCACGTTCCA ATCGCACGGT AGATCTCAGT GCACTCCTCA ATCCATCTGG GGAAACAGTA
1501 CAACGAACTA GAAGATCGGT CCCATCTAAT CAACATCATA GGTCGCGGCG CAGCACAATA
1561 GAGGGGGGTA TAGAAACCGT GAACAATGCA TCACTCCTCA AGACCACCTC ATCTGTGGAA
1621 TTCGCAATGC TACAATTTGC CTATGACTAC ATACAAGCCC ATGTAAATGA AATGTTGAGT
1681 CGGATAGCCA CTGCCTGGTG TACACTTCAG AACCGCGAAC ATGTGCTGTG GACAGAGACC
1741 CTAAAACTCA ATCCCGGTGG GGTGGTCTCG ATGGCCCTAG AACGTCGTGT ATCCGCGCGC
1801 CTACTTGGAG ATGCCGTCGC CGTAACACAA TGTGTTAACA TTTCTAGCGG ACATGTCTAT
1861 ATCCAAAATT CTATGCGGGT GACGGGTTCA TCAACGACAT GTTACAGCCG CCCTCTTGTT
1921 TCCTTCCGTG CCCTCAATGA CTCCGAATAC ATAGAAGGAC AACTAGGGGA AAACAATGAA
1981 CTTCTCGTGG AACGAAAACT AATTGAGCCT TGCACTGTCA ATAATAAGCG GTATTTTAAG
2041 TTTGGGGCAG ATTATGTATA TTTTGAGGAT TATGCGTATG TCCGTAAAGT CCCGCTATCG
2101 GAGATAGAAC TGATAAGTGC GTATGTGAAT TTAAATCTTA CTCTCCTAGA GGATCGTGAA
2161 TTTCTCCCAC TCGAAGTTTA TACACGAGCT GAGCTGGAAG ATACCGGCCT TTTGGACTAC
2221 AGCGAGATTC AACGCCGCAA CCAACTCCAC GCCTTAAAAT TTTATGATAT AGACAGCATA
2281 GTCAGAGTGG ATAATAATCT TGTCATCATG CGTGGTATGG CAAATTTCTT TCAGGGACTC
2341 GGGGATGTGG GGGCTGGTTT CGGCAAGGTG GTCTTAGGGG CTGCGAGTGC GGTAATCTCA
2401 ACAGTATCAG GCGTATCATC ATTTCTAAAC AACCCATTTG GAGCATTGGC CGTGGGACTG
2461 TTAATATTAG CTGGCATCGT CGCAGCATTC CTGGCATATC GCTATATATC TAGATTACGT
2521 GCAAATCCAA TGAAAGCCTT ATATCCTGTG ACGACTAGGA ATTTGAAACA GACGCTAAGA
2581 GCCCGCTCAA CGGCTGGTGG GGATAGCGAC CCGGGAGTCG ATGACTTCGA TGAGGAAAAG
2641 CTAATGCAGG CAAGGGAGAT GATAAAATAT ATGTCCCTCG TATCGGCTAT GGAGCAACAA
2701 GAACATAAGG CGATGAAAAA GAATAAGGGC CCAGCGATCC TAACGAGTCA TCTCACTAAC
2761 ATGGCCCTCC GTCGCCGTGG ACCTAAATAC CAACGCCTCA ATAATCTTGA TAGCGGTGAT
2821 GATACTGAAA CAAATCTTGT CTAA
```

FIG. 5A

DNA sequence of the the H6 promoted FHV gB donor plasmid pC3H6FHVB.

H6 promoter: 3958 - 3835

FHV gB coding region: 3834 - 991

C3 left arm: 15 - 939

C3 right arm: 4056 - 6628

```
   1 GCGGCCGCGT CGACATGCAT TGTTAGTTCT GTAGATCAGT AACGTATAGC ATACGAGTAT
  61 AATTATCGTA GGTAGTAGGT ATCCTAAAAT AAATCTGATA CAGATAATAA CTTTGTAAAT
 121 CAATTCAGCA ATTTCTCTAT TATCATGATA ATGATTAATA CACAGCGTGT CGTTATTTTT
 181 TGTTACGATA GTATTTCTAA AGTAAAGAGC AGGAATCCCT AGTATAATAG AAATAATCCA
 241 TATGAAAAAT ATAGTAATGT ACATATTTCT AATGTTAACA TATTTATAGG TAAATCCAGG
 301 AAGGGTAATT TTTACATATC TATATACGCT TATTACAGTT ATTAAAAATA TACTTGCAAA
 361 CATGTTAGAA GTAAAAAAGA AAGAACTAAT TTTACAAAGT GCTTTACCAA AATGCCAATG
 421 GAAATTACTT AGTATGTATA TAATGTATAA AGGTATGAAT ATCACAAACA GCAAATCGGC
 481 TATTCCCAAG TTGAGAAACG GTATAATAGA TATATTTCTA GATACCATTA ATAACCTTAT
 541 AAGCTTGACG TTTCCTATAA TGCCTACTAA GAAAACTAGA AGATACATAC ATACTAACGC
 601 CATACGAGAG TAACTACTCA TCGTATAACT ACTGTTGCTA ACAGTGACAC TGATGTTATA
 661 ACTCATCTTT GATGTGGTAT AAATGTATAA TAACTATATT ACACTGGTAT TTTATTTCAG
 721 TTATATACTA TATAGTATTA AAAATTATAT TTGTATAATT ATATTATTAT ATTCAGTGTA
 781 GAAAGTAAAA TACTATAAAT ATGTATCTCT TATTTATAAC TTATTAGTAA AGTATGTACT
 841 ATTCAGTTAT ATTGTTTTAT AAAAGCTAAA TGCTACTAGA TTGATATAAA TGAATATGTA
 901 ATAAATTAGT AATGTAGTAT ACTAATATTA ACTCACATTT GACTAATTAG CTATAAAAAC
 961 CCGGGCTGCA GCCCGGGAAG CTTACAAAAA TTAGACAAGA TTTGTTTCAG TATCATCACC
1021 GCTATCAAGA TTATTGAGGC GTTGGTATTT AGGTCCACGG CGACGGAGGG CCATGTTAGT
1081 GAGATGACTC GTTAGGATCG CTGGGCCCTT ATTCTTTTTC ATCGCCTTAT GTTCTTGTTG
1141 CTCCATAGCC GATACGAGGG ACATATATTT TATCATCTCC CTTGCCTGCA TTAGCTTTTC
1201 CTCATCGAAG TCATCGACTC CCGGGTCGCT ATCCCCACCA GCCGTTGAGC GGGCTCTTAG
1261 CGTCTGTTTC AAATTCCTAG TCGTCACAGG ATATAAGGCT TTCATTGGAT TTGCACGTAA
1321 TCTAGATATA TAGCGATATG CCAGGAATGC TGCGACGATG CCAGCTAATA TTAACAGTCC
1381 CACGGCCAAT GCTCCAAATG GGTTGTTTAG AAATGATGAT ACGCCTGATA CTGTTGAGAT
1441 TACCGCACTC GCAGCCCCTA AGACCACCTT GCCGAAACCA GCCCCCACAT CCCCGAGTCC
1501 CTGAAAGAAA TTTGCCATAC CACGCATGAT GACAAGATTA TTATCCACTC TGACTATGCT
1561 GTCTATATCA TAAAATTTTA AGGCGTGGAG TTGGTTGCGG CGTTGAATCT CGCTGTAGTC
1621 CAAAAGGCCG GTATCTTCCA GCTCAGCTCG TGTATAAACT TCGAGTGGGA GAAATTCACG
1681 ATCCTCTAGG AGAGTAAGAT TTAAATTCAC ATACGCACTT ATCAGTTCTA TCTCCGATAG
1741 CGGGACTTTA CGGACATACG CATAATCCTC AAAATATACA TAATCTGCCC CAAACTTAAA
1801 ATACCGCTTA TTATTGACAG TGCAAGGCTC AATTAGTTTT CGTTCCACGA GAAGTTCATT
1861 GTTTTCCCCT AGTTGTCCTT CTATGTATTC GGAGTCATTG AGGGCACGGA AGGAAACAAG
1921 AGGGCGGCTG TAACATGTCG TTGATGAACC CGTCACCCGC ATAGAATTTT GGATATAGAC
1981 ATGTCCGCTA GAAATGTTAA CACATTGTGT TACGGCGACG GCATCTCCAA GTAGGCGCGC
2041 GGATACACGA CGTTCTAGGG CCATCGAGAC CACCCCACCG GGATTGAGTT TTAGGGTCTC
2101 TGTCCACAGC ACATGTTCGC GGTTCTGAAG TGTACACCAG GCAGTGGCTA TCCGACTCAA
2161 CATTTCATTT ACATGGGCTT GTATGTAGTC ATAGGCAAAT TGTAGCATTG CGAATTCCAC
2221 AGATGAGGTG GTCTTGAGGA GTGATGCATT GTTCACGGTT TCTATACCCC CCTCTATTGT
```

FIG. 5B

2281 GCTGCGCCGC GACCTATGAT GTTGATTAGA TGGGACCGAT CTTCTAGTTC GTTGTACTGT
2341 TTCCCCAGAT GGATTGAGGA GTGCACTGAG ATCTACCGTG CGATTGGAAC GTGCTAATTC
2401 ATTGATATAT AACTTTGCTA GTTCGTTGCT GATCATGGGA CGGAAAGCTA TTAGAAATCC
2461 CCCACGGGCT AGGTAGGTCT CCAGGGTTCC AGTCTGAATA TGAGTTTTAC TATATTTACT
2521 CTTATAAATC CGGTCTATGG CTTCGGCTGC CTCCTTGGTG GCACAGTCCC CCAAACGGAT
2581 ACGATTGATT TCAAATTGTG AAGTATTGGA GATGAAAGTA GCGGATATGG TCTTGGCTGT
2641 AAATCTATAG GAGCCCTGAT ATTCATCGCG TAGCATTTCA TCTATTTCCC TCCATTTGGC
2701 TAAGGTACAT ACCCGACCAG ACTTTGGGGT CCAGTTCCAG GCCACTGTCA CATGCGGAGT
2761 TTCCAAAAAA TTGCGAGAAA CTGGTGCCCC CAGTTGTAAT CGCGTATCCA AGTCTATTGG
2821 ATAGTATCCC TCGATTTGTT GAAATCTGTC TGAAGAATAA CTAGTATGTT CTACATGGGC
2881 TCCATCCCTC AGCCCAAAGA ATGGAGACAT GTGAATCACG TCACCAGTGG AGATAGCAAA
2941 TGAGTCATAT GGATATACAG ATCTTGCATC CACTTCCTCT ACGATGCAAT TTACAGAGGT
3001 CCCAGAGTGG TGAAATCCAG CAGCACCGAT CTTTGTGTAT GTTTCATTGG TGGTGTGCCA
3061 TCCACGGGAC TCTGGAGTGT TGAACTTGGA GGGTTTCAGA GGCAGTTCTC TGGGATCCTC
3121 GTCTCGATCA AAGGCCGTAA ATTGATAATT GTTACGAACG TAATCAGCTT TCGAGAGGCA
3181 CATACCCCGT CTATCTATGA GATCTGTAAT CTCTTGAACT TTCACGGGAA CCCTGTCTGT
3241 ATATCGGTTG GTTGTAACGG CATAGGAACT CCCAGACCAT ACCGTTGTCA TAATAATGTT
3301 TTTATAGTAT ATATTTGCCT TGAATTTATA TGGCGCTATA TTTTCTTTAA ATATTACAGC
3361 TATACCCTCG GTAAAATTTT TCCCTAGTTT ATAATCTGGA CAGGCCCGTG GTGGCTCTAA
3421 ACGCACGACA GTAGATCCTG AAGGTGGTGG ACACATATAG AAAGTCGATG GTCCGTTAGC
3481 CTCTATTTGG GACGCACGGA GAGCTTCCCT CATATCCGAC ATATCGGTGG GATCTGTAGT
3541 TGGTTTTGGT GGTGTACCCC CTACCTCAGG GGTAGCTACA GTCCGCCGGG GTTGTTCCGA
3601 TGTGCTTCCA GATTGACCCT CTACTGGACG GGGACCGACT AAGAATAGTA CGATCCAGAT
3661 AAATGAAACA TATCTAGCTA GTCTGGTTAA TCCCGACGAT CCGTTACCAT GTCTGGAGCC
3721 AGTCGCTGCA ATACCGAGTA GAGAAGGGAA AAAACATCTC TGTCGAAAAT AGCCACTGTG
3781 TCCCTGCCAA CGACTCCCTC GTCGCCGCTT CCCAAGATCG CCACGAGTGG ACATTACGAT
3841 ACAAACTTAA CGGATATCGC GATAATGAAA TAATTTATGA TTATTTCTCG CTTTCAATTT
3901 AACACAACCC TCAAGAACCT TTGTATTTAT TTTCACTTTT TAAGTATAGA ATAAAGAAGC
3961 TCTAATTAAT TAAGCTACAA ATAGTTTCGT TTTCACCTTG TCTAATAACT AATTAATTAA
4021 CCCGGATCGA TCCCGATTTT TATGACTAGT TAATCAAATA AAAAGCATAC AAGCTATTGC
4081 TTCGCTATCG TTACAAAATG GCAGGAATTT TGTGTAAACT AAGCCACATA CTTGCCAATG
4141 AAAAAAATAG TAGAAAGGAT ACTATTTTAA TGGGATTAGA TGTTAAGGTT CCTTGGGATT
4201 ATAGTAACTG GGCATCTGTT AACTTTTACG ACGTTAGGTT AGATACTGAT GTTACAGATT
4261 ATAATAATGT TACAATAAAA TACATGACAG GATGTGATAT TTTTCCTCAT ATAACTCTTG
4321 GAATAGCAAA TATGGATCAA TGTGATAGAT TTGAAAATTT CAAAAAGCAA ATAACTGATC
4381 AAGATTTACA GACTATTTCT ATAGTCTGTA AAGAAGAGAT GTGTTTTCCT CAGAGTAACG
4441 CCTCTAAACA GTTGGGAGCG AAAGGATGCG CTGTAGTTAT GAAACTGGAG GTATCTGATG
4501 AACTTAGAGC CCTAAGAAAT GTTCTGCTGA ATGCGGTACC CTGTTCGAAG GACGTGTTTG
4561 GTGATATCAC AGTAGATAAT CCGTGGAATC CTCACATAAC AGTAGGATAT GTTAAGGAGG
4621 ACGATGTCGA AAACAAGAAA CGCCTAATGG AGTGCATGTC CAAGTTTAGG GGGCAAGAAA
4681 TACAAGTTCT AGGATGGTAT TAATAAGTAT CTAAGTATTT GGTATAATTT ATTAAATAGT
4741 ATAATTATAA CAAATAATAA ATAACATGAT AACGGTTTTT ATTAGAATAA AATAGAGATA
4801 ATATCATAAT GATATATAAT ACTTCATTAC CAGAAATGAG TAATGGAAGA CTTATAAATG
4861 AACTGCATAA AGCTATAAGG TATAGAGATA TAAATTTAGT AAGGTATATA CTTAAAAAAT
4921 GCAAATACAA TAACGTAAAT ATACTATCAA CGTCTTTGTA TTTAGCCGTA AGTATTTCTG
4981 ATATAGAAAT GGTAAAATTA TTACTAGAAC ACGGTGCCGA TATTTTAAAA TGTAAAAATC
5041 CTCCTCTTCA TAAAGCTGCT AGTTTAGATA ATACAGAAAT TGCTAAACTA CTAATAGATT
5101 CTGGCGCTGA CATAGAACAG ATACATTCTG GAAATAGTCC GTTATATATT TCTGTATATA
5161 GAAACAATAA GTCATTAACT AGATATTTAT TAAAAAAAGG TGTTAATTGT AATAGATTCT
5221 TTCTAAATTA TTACGATGTA CTGTATGATA AGATATCTGA TGATATGTAT AAAATATTTA
5281 TAGATTTTAA TATTGATCTT AATATACAAA CTAGAAATTT TGAAACTCCG TTACATTACG
5341 CTATAAAGTA TAAGAATATA GATTTAATTA GGATATTGTT AGATAATAGT ATTAAAATAG
5401 ATAAAAGTTT ATTTTTGCAT AAACAGTATC TCATAAAGGC ACTTAAAAAT AATTGTAGTT
5461 ACGATATAAT AGCGTTACTT ATAAATCACG GAGTGCCTAT AAACGAACAA GATGATTTAG

FIG. 5C

5521 GTAAAACCCC ATTACATCAT TCGGTAATTA ATAGAAGAAA AGATGTAACA GCACTTCTGT
5581 TAAATCTAGG AGCTGATATA AACGTAATAG ATGACTGTAT GGGCAGTCCC TTACATTACG
5641 CTGTTTCACG TAACGATATC GAAACAACAA AGACACTTTT AGAAAGAGGA TCTAATGTTA
5701 ATGTGGTTAA TAATCATATA GATACCGTTC TAAATATAGC TGTTGCATCT AAAAACAAAA
5761 CTATAGTAAA CTTATTACTG AAGTACGGTA CTGATACAAA GTTGGTAGGA TTAGATAAAC
5821 ATGTTATTCA CATAGCTATA GAAATGAAAG ATATTAATAT ACTGAATGCG ATCTTATTAT
5881 ATGGTTGCTA TGTAAACGTC TATAATCATA AAGGTTTCAC TCCTCTATAC ATGGCAGTTA
5941 GTTCTATGAA AACAGAATTT GTTAAACTCT TACTTGACCA CGGTGCTTAC GTAAATGCTA
6001 AAGCTAAGTT ATCTGGAAAT ACTCCTTTAC ATAAAGCTAT GTTATCTAAT AGTTTTAATA
6061 ATATAAAATT ACTTTTATCT TATAACGCCG ACTATAATTC TCTAAATAAT CACGGTAATA
6121 CGCCTCTAAC TTGTGTTAGC TTTTTAGATG ACAAGATAGC TATTATGATA ATATCTAAAA
6181 TGATGTTAGA AATATCTAAA AATCCTGAAA TAGCTAATTC AGAAGGTTTT ATAGTAAACA
6241 TGGAACATAT AAACAGTAAT AAAAGACTAC TATCTATAAA AGAATCATGC GAAAAAGAAC
6301 TAGATGTTAT AACACATATA AAGTTAAATT CTATATATTC TTTTAATATC TTTCTTGACA
6361 ATAACATAGA TCTTATGGTA AAGTTCGTAA CTAATCCTAG AGTTAATAAG ATACCTGCAT
6421 GTATACGTAT ATATAGGGAA TTAATACGGA AAAATAAATC ATTAGCTTTT CATAGACATC
6481 AGCTAATAGT TAAAGCTGTA AAAGAGAGTA AGAATCTAGG AATAATAGGT AGGTTACCTA
6541 TAGATATCAA ACATATAATA ATGGAACTAT TAAGTAATAA TGATTTACAT TCTGTTATCA
6601 CCAGCTGTTG TAACCCAGTA GTATAAAG

FIG. 6A

POL/NEF epitopes

```
        10         20         30         40         50         60         70         80         90        100        110
     *    *     *    *     *    *     *    *     *    *     *    *     *    *     *    *     *    *     *    *     *    *
TTTTTTTCAT TATTTAGAAA TTATGCATTT TAGATCTTTA TAAGCGGCCG TGATTAACTA GTCATAAAAA CCCGGGATCG ATTCTAGACT CGAGGGTACC GGATCTTAAT
AAAAAAAGTA ATAAATCTTT AATACGTAAA ATCTAGAAAT ATTCGCCGGC ACTAATTGAT CAGTATTTTT GGGCCCTAGC TAAGATCTGA GCTCCCATGG CCTAGAATTA

       120        130        140        150        160        170        180        190        200        210        220
     *    *     *    *     *    *     *    *     *    *     *    *     *    *     *    *     *    *     *    *     *    *
TAATTAGTCA TCAGGCAGGG CGAGAACGAG ACTATCTGCT CGTTAATTAA TTAGGTCGAC GGATCCCCCA ACAAAAACTA ATCAGCTATC GGGGTTAATT AATTAGTTAT
ATTAATCAGT AGTCCGTCCC GCTCTTGCTC TGATAGACGA GCAATTAATT AATCCAGCTG CCTAGGGGGT TGTTTTTGAT TAGTCGATAG CCCCAATTAA TTAATCAATA

       230        240        250        260        270        280        290        300        310        320        330
     *    *     *    *     *    *     *    *     *    *     *    *     *    *     *    *     *    *     *    *     *    *
TAGACAAGGT GAAAACGAAA CTATTTGTAG CTTAATTAAT TAGAGCTTCT TTATTCTATA CTTAAAAAGT GAAAATAAAT ACAAAGGTTC TTGAGGGTTG TGTTAAATTG
ATCTGTTCCA CTTTTGCTTT GATAAACATC GAATTAATTA ATCTCGAAGA AATAAGATAT GAATTTTTCA CTTTTATTTA TGTTTCCAAG AACTCCCAAC ACAATTTAAC
                                                ___________________________H6 promoter__________________________>

       340        350        360        370        380        390         400        410        420        430
     *    *     *    *     *    *     *    *     *    *     *    *      *      *      *      *      *      *      *      *
AAAGCGAGAA ATAATCATAA ATTATTTCAT TATCGCGATA TCCGTTAAGT TTGTATCGTA ATG CCA CTA ACA GAA GAA GCA GAG CTA GAA CTG GCA GAA AAC
TTTCGCTCTT TATTAGTATT TAATAAAGTA ATAGCGCTAT AGGCAATTCA AACATAGCAT TAC GGT GAT TGT CTT CTT CGT CTC GAT CTT GAC CGT CTT TTG
_________________________H6 promoter________________________> Met Pro Leu Thr Glu Glu Ala Glu Leu Glu Leu Ala Glu Asn
                                                              _________________POL/NEF Epitopes________________>
```

FIG. 6B

```
       440          450          460          470          480          490          500          510          520
 *      *      *      *      *      *      *      *      *      *      *      *      *      *      *      *      *      *
AGA GAG ATT CTA AAA GAA CCA GTA CAT GGA GTG TAT TAT GAC CCA TCA AAA GAC TTA ATA GCA GAA ATA CAG AAG CAG GGG CAA GGC CAA
TCT CTC TAA GAT TTT CTT GGT CAT GTA CCT CAC ATA ATA CTG GGT AGT TTT CTG AAT TAT CGT CTT TAT GTC TTC GTC CCC GTT CCG GTT
Arg Glu Ile Leu Lys Glu Pro Val His Gly Val Tyr Tyr Asp Pro Ser Lys Asp Leu Ile Ala Glu Ile Gln Lys Gln Gly Gln Gly Gln
_____________________________________________POL/NEF Epitopes_______________________________________________________>

       530          540          550          560          570          580          590          600          610
 *      *      *      *      *      *      *      *      *      *      *      *      *      *      *      *      *      *
TGG ACA TAT CAA ATT TAT CAA GAG CCA TTT AAA AAT CTG AAA ACA GGA ATG GAG TGG AGA TTT GAT TCT AGA TTA GCA TTT CAT CAC GTA
ACC TGT ATA GTT TAA ATA GTT CTC GGT AAA TTT TTA GAC TTT TGT CCT TAC CTC ACC TCT AAA CTA AGA TCT AAT CGT AAA GTA GTG CAT
Trp Thr Tyr Gln Ile Tyr Gln Glu Pro Phe Lys Asn Leu Lys Thr Gly Met Glu Trp Arg Phe Asp Ser Arg Leu Ala Phe His His Val
_____________________________________________POL/NEF Epitopes_______________________________________________________>

       620          630          640          650          660          670          680          690          700
 *      *      *      *      *      *      *      *      *      *      *      *      *      *      *      *      *      *
GCT AGA GAA TTA CAT CCT GAA TAT TTT AAA AAT TGT AAG CTT ATG GCA ATA TTC CAA AGT AGC ATG ACA AAA ATC TTA GAG CCT TTT AGA
CGA TCT CTT AAT GTA GGA CTT ATA AAA TTT TTA ACA TTC GAA TAC CGT TAT AAG GTT TCA TCG TAC TGT TTT TAG AAT CTC GGA AAA TCT
Ala Arg Glu Leu His Pro Glu Tyr Phe Lys Asn Cys Lys Leu Met Ala Ile Phe Gln Ser Ser Met Thr Lys Ile Leu Glu Pro Phe Arg
_____________________________________________POL/NEF Epitopes_______________________________________________________>

       710          720          730          740          750          760          770          780          790
 *      *      *      *      *      *      *      *      *      *      *      *      *      *      *      *      *      *
AAA CAA AAT CCA GAC ATA GTT ATC TAT CAA TAC ATG GAT GAT TTG TAT GTA GGA TCT GAC TTA GAA ATA GGG CAG CAT AGA ACA AAA ATA
TTT GTT TTA GGT CTG TAT CAA TAG ATA GTT ATG TAC CTA CTA AAC ATA CAT CCT AGA CTG AAT CTT TAT CCC GTC GTA TCT TGT TTT TAT
Lys Gln Asn Pro Asp Ile Val Ile Tyr Gln Tyr Met Asp Asp Leu Tyr Val Gly Ser Asp Leu Glu Ile Gly Gln His Arg Thr Lys Ile
_____________________________________________POL/NEF Epitopes_______________________________________________________>

       800          810          820          830          840          850          860          870          880
 *      *      *      *      *      *      *      *      *      *      *      *      *      *      *      *      *      *
GAG GAG CTG AGA CAA CAT CTG TTG AGG TGG GGA CTT ACA ACC ATG GTA GGT TTT CCA GTA ACA CCT CAA GTA CCT TTA AGA CCA ATG ACT
CTC CTC GAC TCT GTT GTA GAC AAC TCC ACC CCT GAA TGT TGG TAC CAT CCA AAA GGT CAT TGT GGA GTT CAT GGA AAT TCT GGT TAC TGA
Glu Glu Leu Arg Gln His Leu Leu Arg Trp Gly Leu Thr Thr Met Val Gly Phe Pro Val Thr Pro Gln Val Pro Leu Arg Pro Met Thr
_____________________________________________POL/NEF Epitopes_______________________________________________________>
```

FIG. 6C

```
        890         900          910          920          930          940          950          960          970
  *      *     *      *     *      *     *      *     *      *     *      *     *      *     *      *     *      *
TAC AAA GCA GCT GTA GAT CTT TCT CAC TTT TTA AAA GAA AAA GGA GGT TTA GAA GGG CTA ATT CAT TCT CAA CGA AGA CAA GAT ATT CTT
ATG TTT CGT CGA CAT CTA GAA AGA GTG AAA AAT TTT CTT TTT CCT CCA AAT CTT CCC GAT TAA GTA AGA GTT GCT TCT GTT CTA TAA GAA
Tyr Lys Ala Ala Val Asp Leu Ser His Phe Leu Lys Glu Lys Gly Gly Leu Glu Gly Leu Ile His Ser Gln Arg Arg Gln Asp Ile Leu
____________________________________________POL/NEF Epitopes____________________________________________>

        980         990         1000         1010         1020         1030         1040         1050         1060
  *      *     *      *     *      *     *      *     *      *     *      *     *      *     *      *     *      *
GAT TTG TGG ATT TAT CAT ACA CAA GGA TAT TTT CCT GAT TGG CAG AAT TAC ACA CCA GGA CCA GGA GTC AGA TAC CCA TTA ACC TTT GGT
CTA AAC ACC TAA ATA GTA TGT GTT CCT ATA AAA GGA CTA ACC GTC TTA ATG TGT GGT CCT GGT CCT CAG TCT ATG GGT AAT TGG AAA CCA
Asp Leu Trp Ile Tyr His Thr Gln Gly Tyr Phe Pro Asp Trp Gln Asn Tyr Thr Pro Gly Pro Gly Val Arg Tyr Pro Leu Thr Phe Gly
____________________________________________POL/NEF Epitopes____________________________________________>

       1070        1080         1090         1100         1110         1120         1130         1140         1150
  *      *     *      *     *      *     *      *     *      *     *      *     *      *     *      *     *      *
TGG TGC TAC AAG CTA GTA CCA ATG ATT GAG ACT GTA CCA GTA AAA TTA AAG CCA GGA ATG GAT GGC CCA AAA GTT AAA CAA TGG CCA TTG
ACC ACG ATG TTC GAT CAT GGT TAC TAA CTC TGA CAT GGT CAT TTT AAT TTC GGT CCT TAC CTA CCG GGT TTT CAA TTT GTT ACC GGT AAC
Trp Cys Tyr Lys Leu Val Pro Met Ile Glu Thr Val Pro Val Lys Leu Lys Pro Gly Met Asp Gly Pro Lys Val Lys Gln Trp Pro Leu
____________________________________________POL/NEF Epitopes____________________________________________>

       1160        1170         1180         1190         1200         1210         1220         1230        1240
  *      *     *      *     *      *     *      *     *      *     *      *     *      *     *      *     *      *
ACA GAA GAA AAA ATA AAA GCA TTA GTA GAA ATT TGT ACA GAG ATG GAA AAG GAA GGG AAA ATT TCA AAA ATT GGG CCT TAA TTTTTCT
TGT CTT CTT TTT TAT TTT CGT AAT CAT CTT TAA ACA TGT CTC TAC CTT TTC CTT CCC TTT TAA AGT TTT TAA CCC GGA ATT AAAAAGA
Thr Glu Glu Lys Ile Lys Ala Leu Val Glu Ile Cys Thr Glu Met Glu Lys Glu Gly Lys Ile Ser Lys Ile Gly Pro
____________________________________POL/NEF Epitopes____________________________________>

        1250       1260       1270       1280       1290       1300       1310       1320       1330       1340       1350
    *     *     *     *     *     *     *     *     *     *     *     *     *     *     *     *     *     *     *     *     *     *
GCAGCCCGGG GGATCCTTTT TATAGCTAAT TAGTCACGTA CCTTTGAGAG TACCACTTCA GCTACCTCTT TTGTGTCTCA GAGTAACTTT CTTTAATCAA TTCCAAAACA
CGTCGGGCCC CCTAGGAAAA ATATCGATTA ATCAGTGCAT GGAAACTCTC ATGGTGAAGT CGATGGAGAA AACACAGAGT CTCATTGAAA GAAATTAGTT AAGGTTTTGT
```

FIG. 7A gag (+ pro) and gp120 (+ transmembrane)

| FEATURES | From | To/Span | Description |
|---|---|---|---|
| frag | 1 | 56 | C3 flanking arm |
| frag | 162 | 76 (C) | HIV1 (IIIB) env transmembrane region |
| frag | 1728 | 163 (C) | HIV1 (MN) gp120 gene |
| frag | 1853 | 1729 (C) | vaccinia H6 promoter |
| frag | 1925 | 1983 | vaccinia I3L promoter |
| frag | 1984 | 3746 | HIV1 (IIIB) gag/pro gene |
| frag | 3753 | 3808 | C3 flanking arm |

```
        10        20        30        40        50        60        70        80        90       100       110       120
TAATGTAGTATACTAATATTAACTCACATTTGACTAATTAGCTATAAAAACCCGGGATCGATTCTAGAATAAAAATTATCCCTGCCTAACTCTATTCACTACAGAGAGTACAGCAAAAAC
ATTACATCATATGATTATAATTGAGTGTAAACTGATTAATCGATATTTTTGGGCCCTAGCTAAGATCTTATTTTTAATAGGGACGGATTGAGATAAGTGATGTCTCTCATGTCGTTTTTG
____________________C3 FLANKING ARM____________________>                            G  Q  R  V  R  N  V  V  S  L  V  A  F  V
                                                                             <____HIV1 (IIIB) ENV TRANSMEMBRANE REGION_____

       130       140       150       160       170       180       190       200       210       220       230       240
TATTCTTAAACCTACCAAGCCTCCTACTATCATTATGAATAATCTTTTTTCTCTCTGCACCACTCTTCTCTTTGCCTTGGTGGGTGCTACTCCTAATGGTTCAATTGTTACTACTTTATA
ATAAGAATTTGGATGGTTCGGAGGATGATAGTAATACTTATTAGAAAAAAGAGAGACGTGGTGAGAAGAGAAACGGAACCACCCACGATGAGGATTACCAAGTTAACAATGATGAAATAT
 I  R  L  G  V  L  G  G  V  I  M  I  F  L  R  K  E  R  Q  V  V  R  R  K  A  K  T  P  A  V  G  L  P  E  I  T  V  V  K  Y
<__HIV1 (IIIB) ENV TRANSMEMBRANE REGION___
                                          <____________________________HIV1 (MN) GP120 GENE______________________________

       250       260       270       280       290       300       310       320       330       340       350       360
TTTATATAATTCACTTCTCCAATTGTCCCTCATATCTCCTCCTCCAGGTCTGAAGATCTCGGTGTCGTTCGTGTCCGTGTCCTTACCACCATCTCTTGTTAATAGTAGCCCTGTAATATT
AAATATATTAAGTGAAGAGGTTAACAGGGAGTATAGAGGAGGAGGTCCAGACTTCTAGAGCCACAGCAAGCACAGGCACAGGAATGGTGGTAGAGAACAATTATCATCGGGACATTATAA
 K  Y  L  E  S  R  W  N  D  R  M  D  G  G  G  P  R  F  I  E  T  D  N  T  D  T  D  K  G  G  D  R  T  L  L  L  G  T  I  N
<_______________________________________________HIV1 (MN) GP120 GENE__________________________________________________
```

FIG. 7B

```
        370       380       390       400       410       420       430       440       450       460       470       480
TGATGAACATCTAATTTGTCCTTCAATGGGAGGGGCATATATTGCTTTTCCTACTTCCTGCCACATGTTTATAATTTGTTTTATTTTGCATTGAAGTGTGATATTGTTATTTGACCCTGT
ACTACTTGTAGATTAAACAGGAAGTTACCCTCCCCGTATATAACGAAAAGGATGAAGGACGGTGTACAAATATTAAACAAAATAAAACGTAACTTCACACTATAACAATAAACTGGGACA
 S  S  C  R  I  Q  G  E  I  P  P  A  Y  I  A  K  G  V  E  Q  W  M  N  I  I  Q  K  I  K  C  Q  L  T  I  N  N  N  S  G  T
<________________________________________________HIV1 (MN) GP120 GENE__________________________________________________

        490       500       510       520       530       540       550       560       570       580       590       600
AGTATTATTCCAAGTATTATTACCATTCCAAGTACTATTAAACAGTGGTGATGAATTACAGTAGAAGAATTCCCCTCCACAATTAAAACTGTGCATTACAATTTCTGGGTCCCCTCCTGA
TCATAATAAGGTTCATAATAATGGTAAGGTTCATGATAATTTGTCACCACTACTTAATGTCATCTTCTTAAGGGGAGGTGTTAATTTTGACACGTAATGTTAAAGACCCAGGGGAGGACT
 T  N  N  W  T  N  N  G  N  W  T  S  N  F  L  P  S  S  N  C  Y  F  F  E  G  G  C  N  F  S  H  M  V  I  E  P  D  G  G  S
<________________________________________________HIV1 (MN) GP120 GENE__________________________________________________

        610       620       630       640       650       660       670       680       690       700       710       720
GGATTGATTAAAGACTATTGTTTTATTCTTAAATTGTTCTTTTAATTTGCTAACTATCTGTCTTAAAGTGTCATTCCATTTTGCTCTACTAATGTTACAATGTGCTTGTCTTATAGTTCC
CCTAACTAATTTCTGATAACAAAATAAGAATTTAACAAGAAAATTAAACGATTGATAGACAGAATTTCACAGTAAGGTAAAACGAGATGATTACAATGTTACACGAACAGAATATCAAGG
 S  Q  N  F  V  I  T  K  N  K  F  Q  E  K  L  K  S  V  I  Q  R  L  T  D  N  W  K  A  R  S  I  N  C  H  A  Q  R  I  T  G
<________________________________________________HIV1 (MN) GP120 GENE__________________________________________________

        730       740       750       760       770       780       790       800       810       820       830       840
TATTATATTTTTTGTTGTATAAAATGCTCTCCCTGGTCCTATATGTATCCTTTTTCTTTTATTGTAGTTGGGTCTTGTACAATTAATTTGTACAGATTCATTCAGATGTACTATGATGGT
ATAATATAAAAAACAACATATTTTACGAGAGGGACCAGGATATACATAGGAAAAAGAAAATAACATCAACCCAGAACATGTTAATTAAACATGTCTAAGTAAGTCTACATGATACTACCA
 I  I  N  K  T  T  Y  F  A  R  G  P  G  I  H  I  R  K  R  K  N  Y  N  P  R  T  C  N  I  Q  V  S  E  N  L  H  V  I  I  T
<________________________________________________HIV1 (MN) GP120 GENE__________________________________________________

        850       860       870       880       890       900       910       920       930       940       950       960
TTTAGCATTATCATTGAAATTCTCAGATCTAATTACTACCTCTTCTTCTGCTAGACTGCCATTTAACAGCAGTTGAGTTGATACTACTGGCCTAATTCCATGTGTACATTGTACTGTGCT
AAATCGTAATAGTAACTTTAAGAGTCTAGATTAATGATGGAGAAGAAGACGATCTGACGGTAAATTGTCGTCAACTCAACTATGATGACCGGATTAAGGTACACATGTAACATGACACGA
 K  A  N  D  N  F  N  E  S  R  I  V  V  E  E  E  A  L  S  G  N  L  L  L  Q  T  S  V  V  P  R  I  G  H  T  C  Q  V  T  S
<________________________________________________HIV1 (MN) GP120 GENE__________________________________________________
```

FIG. 7C

```
       970       980       990      1000      1010      1020      1030      1040      1050      1060      1070      1080
GACATTTTTACATGATCCTTTTCCACTGAACTTTTTATCGTTACACTTTAGAATCGCAAAACCAGCCGGGGCACAATAGTGTATGGGAATTGGCTCAAAGGATATCTTTGGACAAGCTTG
CTGTAAAAATGTACTAGGAAAAGGTGACTTGAAAAATAGCAATGTGAAATCTTAGCGTTTTGGTCGGCCCCGTGTTATCACATACCCTTAACCGAGTTTCCTATAGAAACCTGTTCGAAC
 V  N  K  C  S  G  K  G  S  F  K  K  D  N  C  K  L  I  A  F  G  A  P  A  C  Y  H  I  P  I  P  E  F  S  I  K  P  C  A  Q
<______________________________________HIV1 (MN) GP120 GENE______________________________________

      1090      1100      1110      1120      1130      1140      1150      1160      1170      1180      1190      1200
TGTAATGACTGAGGTATTACAACTTATCAACCTATAGCTGGTACTATCATTATTTATTGATACTATATCAAGTTTATAAAGAAGTGCATATTCTTTCTGCATCTTATCTCTTATGCTTGT
ACATTACTGACTCCATAATGTTGAATAGTTGGATATCGACCATGATAGTAATAAATAACTATGATATAGTTCAAATATTTCTTCACGTATAAGAAAGACGTAGAATAGAGAATACGAACA
 T  I  V  S  T  N  C  S  I  L  R  Y  S  T  S  D  N  N  I  S  V  I  D  L  K  Y  L  L  A  Y  E  K  Q  M  K  D  R  I  S  T
<______________________________________HIV1 (MN) GP120 GENE______________________________________

      1210      1220      1230      1240      1250      1260      1270      1280      1290      1300      1310      1320
GGTGATATTGAAAGAGCAGTTTTTCATTTCTCCTCCCTTTATTGTTCCCTCGCTATTACTATTGTTATTAGCAGTACTATTATTGGTATTAGTAGTATTCCTCAAATCAGTGCAATTTAA
CCACTATAACTTTCTCGTCAAAAAGTAAAGAGGAGGGAAATAACAAGGGAGCGATAATGATAACAATAATCGTCATGATAATAACCATAATCATCATAAGGAGTTTAGTCACGTTAAATT
 T  I  N  F  S  C  N  K  M  E  G  G  K  I  T  G  E  S  N  S  N  N  N  A  T  S  N  N  T  N  T  T  N  R  L  D  T  C  N  L
<______________________________________HIV1 (MN) GP120 GENE______________________________________

      1330      1340      1350      1360      1370      1380      1390      1400      1410      1420      1430      1440
AGTAACACAGAGTGGGGTTAATTTTACACATGGCTTTAGGCTTTGATCCCATAAACTGATTATATCCTCATGCATCTGTTCTACCATGTTATTTTTCCACATGTTAAAATTTTCTGTCAC
TCATTGTGTCTCACCCCAATTAAAATGTGTACCGAAATCCGAAACTAGGGTATTTGACTAATATAGGAGTACGTAGACAAGATGGTACAATAAAAAGGTGTACAATTTTAAAAGACAGTG
 T  V  C  L  P  T  L  K  V  C  P  K  L  S  Q  D  W  L  S  I  I  D  E  H  M  Q  E  V  M  N  N  K  W  M  N  F  N  E  T  V
<______________________________________HIV1 (MN) GP120 GENE______________________________________

      1450      1460      1470      1480      1490      1500      1510      1520      1530      1540      1550      1560
ATTTACCAATTCTACTTCTTGTGGGTTGGGGTCTGTGGGTACACAGGCATGTGTGGCCCAAACATTATGTACCTCTGTATCATATGCTTTAGCATCTGATGCACAAAATAGAGTGGTGGT
TAAATGGTTAAGATGAAGAACACCCAACCCCAGACACCCATGTGTCCGTACACACCGGGTTTGTAATACATGGAGACATAGTATACGAAATCGTAGACTACGTGTTTTATCTCACCACCA
 N  V  L  E  V  E  Q  P  N  P  D  T  P  V  C  A  H  T  A  W  V  N  H  V  E  T  D  Y  A  K  A  D  S  A  C  F  L  T  T  T
<______________________________________HIV1 (MN) GP120 GENE______________________________________
```

FIG. 7D

```
      1570      1580      1590      1600      1610      1620      1630      1640      1650      1660      1670      1680
TGCTTCTTTCCACACAGGTACCCCATAATAGACTGTGACCCACAATTTTTCTGTAGCACTACAGATCATCAACATCCCAAGGAGCATGGTGCCCCATCTCCACCCCCATCTCCACAAGTG
ACGAAGAAAGGTGTGTCCATGGGGTATTATCTGACACTGGGTGTTAAAAAGACATCGTGATGTCTAGTAGTTGTAGGGTTCCTCGTACCACGGGGTAGAGGTGGGGGTAGAGGTGTTCAC
 A  E  K  W  V  P  V  G  Y  Y  V  T  V  W  L  K  E  T  A  S  C  I  M  L  M  G  L  L  M  T  G  W  R  W  G  W  R  W  L  H
<________________________________________________HIV1 (MN) GP120 GENE___________________________________________________

      1690      1700      1710      1720      1730      1740      1750      1760      1770      1780      1790      1800
CTGATATTTCTCCTTCACTCTCATTGCCACTGTCTTCTGCTCTTTCATATACGATACAAACTTAACGCATATCGCGATAATGAAATAATTTATGATTATTTCTCGCTTTCAATTTAACAC
GACTATAAAGAGGAAGTGAGAGTAACGGTGACAGAAGACGAGAAAGTATATGCTATGTTTGAATTGCGTATAGCGCTATTACTTTATTAAATACTAATAAAGAGCGAAAGTTAAATTGTG
 Q  Y  K  E  K  V  R  M  A  V  T  K  Q  E  K  M
<____________HIV1 (MN) GP120 GENE______________
                                               <________________________VACCINIA H6 PROMOTER___________________________

      1810      1820      1830      1840      1850      1860      1870      1880      1890      1900      1910      1920
AACCCTCAAGAACCTTTGTATTTATTTTCACTTTTTAAGTATAGAATAAAGAAGCTCTAATTAATTAAGCTACAAATAGTTTCGTTTTCACCTTGTCTAATAACTAATTAATTAACCCGG
TTGGGAGTTCTTGGAAACATAAATAAAAGTGAAAAATTCATATCTTATTTCTTCGAGATTAATTAATTCGATGTTTATCAAAGCAAAAGTGGAACAGATTATTGATTAATTAATTGGGCC
<______________VACCINIA H6 PROMOTER__________________

      1930      1940      1950      1960      1970      1980      1990      2000      2010      2020      2030      2040
ATCTTGAGATAAAGTGAAAATATATATCATTATATTACAAAGTACAATTATTTAGGTTTAATCATGGGTGCGAGAGCGTCAGTATTAAGCGGGGGAGAATTAGATCGATGGAAAAAATT
TAGAACTCTATTTCACTTTTATATATAGTAATATAATGTTTCATGTTAATAAATCCAAATTAGTACCCACGCTCTCGCAGTCATAATTCGCCCCCTCTTAATCTAGCTACCCTTTTTTAA
   _________________VACCINIA I3L PROMOTER____________________> M  G  A  R  A  S  V  L  S  G  G  E  L  D  R  W  E  K  I
                                                               ________________HIV1 (IIIB) GAG/PRO GENE__________________>

      2050      2060      2070      2080      2090      2100      2110      2120      2130      2140      2150      2160
CGGTTAAGGCCAGGGGGAAAGAAAAAATATAAATTAAAACATATAGTATGGGCAAGCAGGGAGCTAGAACGATTCGCAGTTAATCCTGGCCTGTTAGAAACATCAGAAGGCTGTAGACAA
GCCAATTCCGGTCCCCCTTTCTTTTTTATATTTAATTTTGTATATCATACCCGTTCGTCCCTCGATCTTGCTAAGCGTCAATTAGGACCGGACAATCTTTGTAGTCTTCCGACATCTGTT
 R  L  R  P  G  G  K  K  K  Y  K  L  K  H  I  V  W  A  S  R  E  L  E  R  F  A  V  N  P  G  L  L  E  T  S  E  G  C  R  Q
________________________________________________HIV1 (IIIB) GAG/PRO GENE_________________________________________________>

      2170      2180      2190      2200      2210      2220      2230      2240      2250      2260      2270      2280
```

```
ATACTGGGACAGCTACAACCATCCCTTCAGACAGGATCAGAAGAACTTAGATCATTATATAATACAGTAGCAACCCTCTATTGTGTGCATCAAAGGATAGAGATAAAAGACACCAAGGAA
TATGACCCTGTCGATGTTGGTAGGGAAGTCTGTCCTAGTCTTCTTGAATCTAGTAATATATTATGTCATCGTTGGGAGATAACACACGTAGTTTCCTATCTCTATTTTCTGTGGTTCCTT
 I  L  G  Q  L  Q  P  S  L  Q  T  G  S  E  E  L  R  S  L  Y  N  T  V  A  T  L  Y  C  V  H  Q  R  I  E  I  K  D  T  K  E
______________________________HIV1 (IIIB) GAG/PRO GENE______________________________>

      2290      2300      2310      2320      2330      2340      2350      2360      2370      2380      2390      2400
GCTTTAGACAAGATAGAGGAAGAGCAAAACAAAAGTAAGAAAAAAGCACAGCAAGCAGCAGCTGACACAGGACACAGCAATCAGGTCAGCCAAAATTACCCTATAGTGCAGAACATCCAG
CGAAATCTGTTCTATCTCCTTCTCGTTTTGTTTTCATTCTTTTTTCGTGTCGTTCGTCGTCGACTGTGTCCTGTGTCGTTAGTCCAGTCGGTTTTAATGGGATATCACGTCTTGTAGGTC
 A  L  D  K  I  E  E  E  Q  N  K  S  K  K  K  A  Q  Q  A  A  A  D  T  G  H  S  N  Q  V  S  Q  N  Y  P  I  V  Q  N  I  Q
______________________________HIV1 (IIIB) GAG/PRO GENE______________________________>

      2410      2420      2430      2440      2450      2460      2470      2480      2490      2500      2510      2520
GGGCAAATGGTACATCAGGCCATATCACCTAGAACTTTAAATGCATGGGTAAAAGTAGTAGAAGAGAAGGCTTTCAGCCCAGAAGTGATACCCATGTTTTCAGCATTATCAGAAGGAGCC
CCCGTTTACCATGTAGTCCGGTATAGTGGATCTTGAAATTTACGTACCCATTTTCATCATCTTCTCTTCCGAAAGTCGGGTCTTCACTATGGGTACAAAAGTCGTAATAGTCTTCCTCGG
 G  Q  M  V  H  Q  A  I  S  P  R  T  L  N  A  W  V  K  V  V  E  E  K  A  F  S  P  E  V  I  P  M  F  S  A  L  S  E  G  A
______________________________HIV1 (IIIB) GAG/PRO GENE______________________________>

      2530      2540      2550      2560      2570      2580      2590      2600      2610      2620      2630      2640
ACCCCACAAGATTTAAACACCATGCTAAACACAGTGGGGGGACATCAAGCAGCCATGCAAATGTTAAAAGAGACCATCAATGAGGAAGCTGCAGAATGGGATAGAGTGCATCCAGTGCAT
TGGGGTGTTCTAAATTTGTGGTACGATTTGTGTCACCCCCCTGTAGTTCGTCGGTACGTTTACAATTTTCTCTGGTAGTTACTCCTTCGACGTCTTACCCTATCTCACGTAGGTCACGTA
 T  P  Q  D  L  N  T  M  L  N  T  V  G  G  H  Q  A  A  M  Q  M  L  K  E  T  I  N  E  E  A  A  E  W  D  R  V  H  P  V  H
______________________________HIV1 (IIIB) GAG/PRO GENE______________________________>

      2650      2660      2670      2680      2690      2700      2710      2720      2730      2740      2750      2760
GCAGGGCCTATTGCACCAGGCCAGATGAGAGAACCAAGGGGAAGTGACATAGCAGGAACTACTAGTACCCTTCAGGAACAAATAGGATGGATGACAAATAATCCACCTATCCCAGTAGGA
CGTCCCGGATAACGTGGTCCGGTCTACTCTCTTGGTTCCCCTTCACTGTATCGTCCTTGATGATCATGGGAAGTCCTTGTTTATCCTACCTACTGTTTATTAGGTGGATAGGGTCATCCT
 A  G  P  I  A  P  G  Q  M  R  E  P  R  G  S  D  I  A  G  T  T  S  T  L  Q  E  Q  I  G  W  M  T  N  N  P  P  I  P  V  G
______________________________HIV1 (IIIB) GAG/PRO GENE______________________________>
```

FIG. 7F

```
    2770      2780      2790      2800      2810      2820      2830      2840      2850      2860      2870      2880
GAAATTTATAAAAGATGGATAATCCTGGGATTAAATAAAATAGTAAGAATGTATAGCCCTACCAGCATTCTGGACATAAGACAAGGACCAAAAGAACCCTTTAGAGACTATGTAGACCGG
CTTTAAATATTTTCTACCTATTAGGACCCTAATTTATTTTATCATTCTTACATATCGGGATGGTCGTAAGACCTGTATTCTGTTCCTGGTTTTCTTGGGAAATCTCTGATACATCTGGCC
 E  I  Y  K  R  W  I  I  L  G  L  N  K  I  V  R  M  Y  S  P  T  S  I  L  D  I  R  Q  G  P  K  E  P  F  R  D  Y  V  D  R
_______________________________________________HIV1 (IIIB) GAG/PRO GENE_______________________________________________>

    2890      2900      2910      2920      2930      2940      2950      2960      2970      2980      2990      3000
TTCTATAAAACTCTAAGAGCCGAGCAAGCTTCACAGGAGGTAAAAAATTGGATGACAGAAACCTTGTTGGTCCAAAATGCGAACCCAGATTGTAAGACTATTTTAAAAGCATTGGGACCA
AAGATATTTTGAGATTCTCGGCTCGTTCGAAGTGTCCTCCATTTTTTAACCTACTGTCTTTGGAACAACCAGGTTTTACGCTTGGGTCTAACATTCTGATAAAATTTTCGTAACCCTGGT
 F  Y  K  T  L  R  A  E  Q  A  S  Q  E  V  K  N  W  M  T  E  T  L  L  V  Q  N  A  N  P  D  C  K  T  I  L  K  A  L  G  P
_______________________________________________HIV1 (IIIB) GAG/PRO GENE_______________________________________________>

    3010      3020      3030      3040      3050      3060      3070      3080      3090      3100      3110      3120
GCGGCTACACTAGAAGAAATGATGACAGCATGTCAGGGAGTAGGAGGACCCGGCCATAAGGCAAGAGTTTTGGCTGAAGCAATGAGCCAAGTAACAAATTCAGCTACCATAATGATGCAG
CGCCGATGTGATCTTCTTTACTACTGTCGTACAGTCCCTCATCCTCCTGGGCCGGTATTCCGTTCTCAAAACCGACTTCGTTACTCGGTTCATTGTTTAAGTCGATGGTATTACTACGTC
 A  A  T  L  E  E  M  M  T  A  C  Q  G  V  G  G  P  G  H  K  A  R  V  L  A  E  A  M  S  Q  V  T  N  S  A  T  I  M  M  Q
_______________________________________________HIV1 (IIIB) GAG/PRO GENE_______________________________________________>

    3130      3140      3150      3160      3170      3180      3190      3200      3210      3220      3230      3240
AGAGGCAATTTTAGGAACCAAAGAAAGATTGTTAAGTGTTTCAATTGTGGCAAAGAAGGGCACACAGCCAGAAATTGCAGGGCCCCTAGGAAAAAGGGCTGTTGGAAATGTGGAAAGGAA
TCTCCGTTAAAATCCTTGGTTTCTTTCTAACAATTCACAAAGTTAACACCGTTTCTTCCCGTGTGTCGGTCTTTAACGTCCCGGGGATCCTTTTTCCCGACAACCTTTACACCTTTCCTT
 R  G  N  F  R  N  Q  R  K  I  V  K  C  F  N  C  G  K  E  G  H  T  A  R  N  C  R  A  P  R  K  K  G  C  W  K  C  G  K  E
_______________________________________________HIV1 (IIIB) GAG/PRO GENE_______________________________________________>

    3250      3260      3270      3280      3290      3300      3310      3320      3330      3340      3350      3360
GGACACCAAATGAAAGATTGTACTGAGAGACAGGCTAATTTTTTAGGGAAGATCTGGCCTTCCTACAAGGGAAGGCCAGGGAATTTTCTTCAGAGCAGACCAGAGCCAACAGCCCCACCA
CCTGTGGTTTACTTTCTAACATGACTCTCTGTCCGATTAAAAAATCCCTTCTAGACCGGAAGGATGTTCCCTTCCGGTCCCTTAAAAGAAGTCTCGTCTGGTCTCGGTTGTCGGGGTGGT
 G  H  Q  M  K  D  C  T  E  R  Q  A  N  F  L  G  K  I  W  P  S  Y  K  G  R  P  G  N  F  L  Q  S  R  P  E  P  T  A  P  P
_______________________________________________HIV1 (IIIB) GAG/PRO GENE_______________________________________________>
```

FIG. 7G

```
        3370      3380      3390      3400      3410      3420      3430      3440      3450      3460      3470      3480
GAAGAGAGCTTCAGGTCTGGGGTAGAGACAACAACTCCCCCTCAGAAGCAGGAGCCGATAGACAAGGAACTGTATCCTTTAACTTCCCTCAGATCACTCTTTGGCAACGACCCCTCGTCA
CTTCTCTCGAAGTCCAGACCCCATCTCTGTTGTTGAGGGGGAGTCTTCGTCCTCGGCTATCTGTTCCTTGACATAGGAAATTGAAGGGAGTCTAGTGAGAAACCGTTGCTGGGGAGCAGT
 E  E  S  F  R  S  G  V  E  T  T  T  P  P  Q  K  Q  E  P  I  D  K  E  L  Y  P  L  T  S  L  R  S  L  F  G  N  D  P  S  S
                                                                                P  Q  I  T  L  W  Q  R  P  L  V
_______________________________________________HIV1 (IIIB) GAG/PRO GENE_______________________________________________>

        3490      3500      3510      3520      3530      3540      3550      3560      3570      3580      3590      3600
CAATAAAGATAGGGGGGCAACTAAAGGAAGCTCTATTAGATACAGGAGCAGATGATACAGTATTAGAAGAAATGAGTTTGCCAGGAAGATGGAAACCAAAAATGATAGGGGGAATTGGAG
GTTATTTCTATCCCCCCGTTGATTTCCTTCGAGATAATCTATGTCCTCGTCTACTATGTCATAATCTTCTTTACTCAAACGGTCCTTCTACCTTTGGTTTTTACTATCCCCCTTAACCTC
 Q
T  I  K  I  G  G  Q  L  K  E  A  L  L  D  T  G  A  D  D  T  V  L  E  E  M  S  L  P  G  R  W  K  P  K  M  I  G  G  I  G
_______________________________________________HIV1 (IIIB) GAG/PRO GENE_______________________________________________>

        3610      3620      3630      3640      3650      3660      3670      3680      3690      3700      3710      3720
GTTTTATCAAAGTAAGACAGTATGATCAGATACTCATAGAAATCTGTGGACATAAAGCTATAGGTACAGTATTAGTAGGACCTACACCTGTCAACATAATTGGAAGAAATCTGTTGACTC
CAAAATAGTTTCATTCTGTCATACTAGTCTATGAGTATCTTTAGACACCTGTATTTCGATATCCATGTCATAATCATCCTGGATGTGGACAGTTGTATTAACCTTCTTTAGACAACTGAG
G  F  I  K  V  R  Q  Y  D  Q  I  L  I  E  I  C  G  H  K  A  I  G  T  V  L  V  G  P  T  P  V  N  I  I  G  R  N  L  L  T
_______________________________________________HIV1 (IIIB) GAG/PRO GENE_______________________________________________>

        3730      3740      3750      3760      3770      3780      3790      3800
AGATTGGTTGCACTTTAAATTTTTAACCCGGGGGATCCCGATTTTTATGACTAGTTAATCAAATAAAAAGCATACAAGCTATTGCTTC
TCTAACCAACGTGAAATTTAAAAATTGGGCCCCCTAGGGCTAAAAATACTGATCAATTAGTTTATTTTTCGTATGTTCGATAACGAAG
Q  I  G  C  T  L  N  F          <___________________C3 FLANKING ARM___________________
___HIV1 (IIIB) GAG/PRO____>
```

```
         10         20         30         40         50         60         70         80         90        100        110
     *    *    *    *    *    *    *    *    *    *    *    *    *    *    *    *    *    *    *    *    *    *
GAGCTCGCGG CCGCCTATCA AAAGTCTTAA TGAGTTAGGT GTAGATAGTA TAGATATTAC TACAAAGGTA TTCATATTTC CTATCAATTC TAAAGTAGAT GATATTAATA
CTCGAGCGCC GGCGGATAGT TTTCAGAATT ACTCAATCCA CATCTATCAT ATCTATAATG ATGTTTCCAT AAGTATAAAG GATAGTTAAG ATTTCATCTA CTATAATTAT

        120        130        140        150        160        170        180        190        200        210        220
     *    *    *    *    *    *    *    *    *    *    *    *    *    *    *    *    *    *    *    *    *    *
ACTCAAAGAT GATGATAGTA GATAATAGAT ACGCTCATAT AATGACTGCA AATTTGGACG GTTCACATTT TAATCATCAC GCGTTCATAA GTTTCAACTG CATAGATCAA
TGAGTTTCTA CTACTATCAT CTATTATCTA TGCGAGTATA TTACTGACGT TTAAACCTGC CAAGTGTAAA ATTAGTAGTG CGCAAGTATT CAAAGTTGAC GTATCTAGTT

        230        240        250        260        270        280        290        300        310        320        330
     *    *    *    *    *    *    *    *    *    *    *    *    *    *    *    *    *    *    *    *    *    *
AATCTCACTA AAAAGATAGC CGATGTATTT GAGAGAGATT GGACATCTAA CTACGCTAAA GAAATTACAG TTATAAATAA TACATAATGG ATTTTGTTAT CATCAGTTAT
TTAGAGTGAT TTTTCTATCG GCTACATAAA CTCTCTCTAA CCTGTAGATT GATGCGATTT CTTTAATGTC AATATTTATT ATGTATTACC TAAAACAATA GTAGTCAATA

        340        350        360        370        380        390        400        410        420        430        440
     *    *    *    *    *    *    *    *    *    *    *    *    *    *    *    *    *    *    *    *    *    *
ATTTAACATA AGTACAATAA AAAGTATTAA ATAAAAATAC TTACTTACGA AAAAATGACT AATTAGCTAT AAAAACCCAG ATCTCTCGAG GTCGACGGTA TCGATAAGCT
TAAATTGTAT TCATGTTATT TTTCATAATT TATTTTTATG AATGAATGCT TTTTTACTGA TTAATCGATA TTTTTGGGTC TAGAGAGCTC CAGCTGCCAT AGCTATTCGA

        450        460            470         480         490         500         510         520         530
     *    *    *    *       *      *     *     *     *     *     *     *     *     *     *     *     *     *
TGATATCGAA TTCATAAAAA TT A TTG ATG TCT ACA CAT CCT TTT GTA ATT GAC ATC TAT ATA TCC TTT TGT ATA ATC AAC TCT AAT CAC TTT
ACTATAGCTT AAGTATTTTT AA T AAC TAC AGA TGT GTA GGA AAA CAT TAA CTG TAG ATA TAT AGG AAA ACA TAT TAG TTG AGA TTA GTG AAA
                           <Q   H   R   C   M   R   K   Y   N   V   D   I   Y   G   K   T   Y   D   V   R   I   V   K
                           -------------------------------------------k3L------------------------------------------
```

```
         540         550         560         570         580         590         600         610         620
   *      *      *      *      *      *      *      *      *      *      *      *      *      *      *      *      *      *
AAC TTT TAC AGT TTT CCC TAC CAG TTT ATC CCT ATA TTC AAC ATA TCT ATC CAT ATG CAT CTT AAC ACT CTC TGC CAA GAT AGC TTC AGA
TTG AAA ATG TCA AAA GGG ATG GTC AAA TAG GGA TAT AAG TTG TAT AGA TAG GTA TAC GTA GAA TTG TGA GAG ACG GTT CTA TCG AAG TCT
<V   K   V   T   K   G   V   L   K   D   R   Y   E   V   Y   R   D   M   H   M   K   V   S   E   A   L   I   A   E   S
----------------------------------------------------------------------K3L-------------------------------------------

         630         640         650         660         670         680         690         700         710
   *      *      *      *      *      *      *      *      *      *      *      *      *      *      *      *      *      *
GTG AGG ATA GTC AAA AAG ATA AAT GTA TAG AGC ATA ATC CTT CTC GTA TAC TCT GCC CTT TAT TAC ATC GCC CGC ATT GGG CAA CGA ATA
CAC TCC TAT CAG TTT TTC TAT TTA CAT ATC TCG TAT TAG GAA GAG CAT ATG AGA CGG GAA ATA ATG TAG CGG GCG TAA CCC GTT GCT TAT
<H   P   Y   D   F   L   Y   I   Y   L   A   Y   D   K   E   Y   V   R   G   K   I   V   D   G   A   N   P   L   S   Y
----------------------------------------------------------------------K3L-------------------------------------------

         720         730         740         750         760         770         780         790         800         810
   *      *      *      *      *      *      *      *      *      *      *      *      *      *      *      *      *      *
ACA AAA TGC AAG CAT ACG ATACAAACTT AACGGATATC GCGATAATGA AATAATTTAT GATTATTTCT CGCTTTCAAT TTAACACAAC CCTCAAGAAC
TGT TTT ACG TTC GTA TGC TATGTTTGAA TTGCCTATAG CGCTATTACT TTATTAAATA CTAATAAAGA GCGAAAGTTA AATTGTGTTG GGAGTTCTTG
<C   F   A   L   M
----------------K3L
```

FIG. 8B

```
        820        830        840        850        860        870        880        890        900        910        920
    *     *     *     *     *     *     *     *     *     *     *     *     *     *     *     *     *     *     *     *     *     *
CTTTGTATTT ATTTTCACTT TTTAAGTATA GAATAAAGAA AGCTCTAATT AATTAATGAA CAGATTGTTT CGTTTTCCCC TTGGCGTATC ACTAATTAAT TAACCCGGGC
GAAACATAAA TAAAAGTGAA AAATTCATAT CTTATTTCTT TCGAGATTAA TTAATTACTT GTCTAACAAA GCAAAAGGGG AACCGCATAG TGATTAATTA ATTGGGCCCG

        930        940        950        960        970        980        990       1000       1010       1020       1030
    *     *     *     *     *     *     *     *     *     *     *     *     *     *     *     *     *     *     *     *     *     *
TGCAGCTCGA GGAATTCAAC TATATCGACA TATTTCATTT GTATACACAT AACCATTACT AACGTAGAAT GTATAGGAAG AGATGTAACG GGAACAGGGT TTGTTGATTC
ACGTCGAGCT CCTTAAGTTG ATATAGCTGT ATAAAGTAAA CATATGTGTA TTGGTAATGA TTGCATCTTA CATATCCTTC TCTACATTGC CCTTGTCCCA AACAACTAAG

       1040       1050       1060       1070       1080       1090       1100       1110       1120       1130       1140
    *     *     *     *     *     *     *     *     *     *     *     *     *     *     *     *     *     *     *     *     *     *
GCAAACTATT CTAATACATA ATTCTTCTGT TAATACGTCT TGCACGTAAT CTATTATAGA TGCCAAGATA TCTATATAAT TATTTTGTAA GATGATGTTA ACTATGTGAT
CGTTTGATAA GATTATGTAT TAAGAAGACA ATTATGCAGA ACGTGCATTA GATAATATCT ACGGTTCTAT AGATATATTA ATAAAACATT CTACTACAAT TGATACACTA
```

FIG. 8C

```
      1150       1160       1170       1180       1190       1200       1210       1220       1230       1240       1250
   *     *    *     *    *     *    *     *    *     *    *     *    *     *    *     *    *     *    *     *    *     *
CTATATAAGT AGTGTAATAA TTCATGTATT TCGATATATG TTCCAACTCT GTCTTTGTGA TGTCTAGTTT CGTAATATCT ATAGCATCCT CAAAAAATAT ATTCGCATAT
GATATATTCA TCACATTATT AAGTACATAA AGCTATATAC AAGGTTGAGA CAGAAACACT ACAGATCAAA GCATTATAGA TATCGTAGGA GTTTTTTATA TAAGCGTATA

      1260       1270       1280       1290       1300       1310       1320       1330       1340       1350       1360
   *     *    *     *    *     *    *     *    *     *    *     *    *     *    *     *    *     *    *     *    *     *
ATTCCCAAGT CTTCAGTTCT ATCTTCTAAA AAATCTTCAA CGTATGGAAT ATAATAATCT ATTTTACCTC TTCTGATATC ATTAATGATA TAGTTTTTGA CACTATCTTC
TAAGGGTTCA GAAGTCAAGA TAGAAGATTT TTTAGAAGTT GCATACCTTA TATTATTAGA TAAAATGGAG AAGACTATAG TAATTACTAT ATCAAAAACT GTGATAGAAG

      1370       1380       1390       1400       1410       1420       1430       1440       1450       1460       1470
   *     *    *     *    *     *    *     *    *     *    *     *    *     *    *     *    *     *    *     *    *     *
TGTCAATTGA TTCTTATTCA CTATATCTAA GAAACGGATA GCGTCCCTAG GACGAACTAC TGCCATTAAT ATCTCTATTA TAGCTTCTGG ACATAATTCA TCTATTATAC
ACAGTTAACT AAGAATAAGT GATATAGATT CTTTGCCTAT CGCAGGGATC CTGCTTGATG ACGGTAATTA TAGAGATAAT ATCGAAGACC TGTATTAAGT AGATAATATG

      1480       1490       1500       1510       1520       1530       1540       1550       1560       1570       1580
   *     *    *     *    *     *    *     *    *     *    *     *    *     *    *     *    *     *    *     *    *     *
CAGAATTAAT GGGAACTATT CCGTATCTAT CTAACATAGT TTTAAGAAAG TCAGAATCTA AGACCTGATG TTCATATATT GGTTCATACA TGAAATGATC TCTATTGATG
GTCTTAATTA CCCTTGATAA GGCATAGATA GATTGTATCA AAATTCTTTC AGTCTTAGAT TCTGGACTAC AAGTATATAA CCAAGTATGT ACTTTACTAG AGATAACTAC

      1590       1600       1610       1620       1630       1640       1650       1660       1670       1680       1690
   *     *    *     *    *     *    *     *    *     *    *     *    *     *    *     *    *     *    *     *    *     *
ATAGTGACTA TTTCATTCTC TGAAAATTGG TAACTCATTC TATATATGCT TTCCTTGTTG ATGAAGGATA GAATATACTC AATAGAATTT GTACCAACAA ACTGTTCTCT
TATCACTGAT AAAGTAAGAG ACTTTTAACC ATTGAGTAAG ATATATACGA AAGGAACAAC TACTTCCTAT CTTATATGAG TTATCTTAAA CATGGTTGTT TGACAAGAGA

      1700       1710       1720       1730       1740       1750       1760       1770       1780       1790       1800
   *     *    *     *    *     *    *     *    *     *    *     *    *     *    *     *    *     *    *     *    *     *
TATGAATCGT ATATCATCAT CTGAAATAAT CATGTAAGGC ATACATTTAA CAATTAGAGA CTTGTCTCCT GTTATCAATA TACTATTCTT GTGATAATTT ATGTGTGAGG
ATACTTAGCA TATAGTAGTA GACTTTATTA GTACATTCCG TATGTAAATT GTTAATCTCT GAACAGAGGA CAATAGTTAT ATGATAAGAA CACTATTAAA TACACACTCC
```

FIG. 8D

```
      1810       1820       1830       1840       1850       1860       1870       1880       1890       1900       1910
       *    *      *    *      *    *      *    *      *    *      *    *      *    *      *    *      *    *      *    *      *    *
CAAATTTGTC CACGTTCTTT AATTTTGTTA TAGTAGATAT CAAATCCAAT GGAGCTACAG TTCTTGGCTT AAACAGATAT AGTTTTTCTG GAACAAATTC TACAACATTA
GTTTAAACAG GTGCAAGAAA TTAAAACAAT ATCATCTATA GTTTAGGTTA CCTCGATGTC AAGAACCGAA TTTGTCTATA TCAAAAAGAC CTTGTTTAAG ATGTTGTAAT

      1920       1930       1940       1950       1960       1970       1980       1990       2000       2010       2020
       *    *      *    *      *    *      *    *      *    *      *    *      *    *      *    *      *    *      *    *      *    *
TTATAAAGGA CTTTGGGTAG ATAAGTGGGA TGAAATCCTA TTTTAATTAA TGCTATCGCA TTGTCCTCGT GCAAATATCC AAACGCTTTT GTGATAGTAT GGCATTCATT
AATATTTCCT GAAACCCATC TATTCACCCT ACTTTAGGAT AAAATTAATT ACGATAGCGT AACAGGAGCA CGTTTATAGG TTTGCGAAAA CACTATCATA CCGTAAGTAA

      2030       2040       2050       2060       2070       2080       2090       2100       2110       2120       2130
       *    *      *    *      *    *      *    *      *    *      *    *      *    *      *    *      *    *      *    *      *    *
GTCTAGAAAC GCTCTACGAA TATCTGTGAC AGATATCATC TTTAGAGAAT ATACTAGTCG CGTTAATAGT ACTACAATTT GTATTTTTTA ATCTATCTCA ATAAAAAAAT
CAGATCTTTG CGAGATGCTT ATAGACACTG TCTATAGTAG AAATCTCTTA TATGATCAGC GCAATTATCA TGATGTTAAA CATAAAAAAT TAGATAGAGT TATTTTTTTA

      2140       2150       2160       2170       2180        2190         2200          2210          2220          2230
       *    *      *    *      *    *      *    *      *    *      *     *      *     *      *     *      *     *      *     *
TAATATGTAT GATTCAATGT ATAACTAAAC TACTAACTGT TATTGATAAC TAGAATCA GAA TCT AAT GAT GAC GTA ACC AAG AAG TTT ATC TAC TGC CAA
ATTATACATA CTAAGTTACA TATTGATTTG ATGATTGACA ATAACTATTG ATCTTAGT CTT AGA TTA CTA CTG CAT TGG TTC TTC AAA TAG ATG ACG GTT
                                                                <F   R   I   I   V   Y   G   L   L   K   D   V   A   L
                                                                -------E3L-------------------------------------------

     2240          2250          2260          2270          2280          2290          2300          2310          2320
  *     *     *     *     *     *     *     *     *     *     *     *     *     *     *     *     *     *     *     *
TTT AGC TGC ATT ATT TTT AGC ATC TCG TTT AGA TTT TCC ATC TGC CTT ATC GAA TAC TCT TCC GTC GAT GTC TAC ACA GGC ATA AAA TGT
AAA TCG ACG TAA TAA AAA TCG TAG AGC AAA TCT AAA AGG TAG ACG GAA TAG CTT ATG AGA AGG CAG CTA CAG ATG TGT CCG TAT TTT ACA
<K   A   A   N   N   K   A   D   R   K   S   K   G   D   A   K   D   F   V   R   G   D   I   D   V   C   A   Y   F   T
--------------------------------------------------------------E3L------------------------------------------------------
```

FIG. 8E

```
2330       2340       2350       2360       2370       2380       2390       2400       2410
   *    *    *    *    *    *    *    *    *    *    *    *    *    *    *    *    *    *
AGG AGA GTT ACT AGG CCC AAC TGA TTC AAT ACG AAA AGA CCA ATC TCT CTT AGT TAT TTG GCA GTA CTC ATT AAT AAT GGT GAC AGG GTT
TCC TCT CAA TGA TCC GGG TTG ACT AAG TTA TGC TTT TCT GGT TAG AGA GAA TCA ATA AAC CGT CAT GAG TAA TTA TTA CCA CTG TCC CAA
<P   S   N   S   P   G   V   S   E   I   R   F   S   W   D   R   K   T   I   Q   C   Y   E   N   I   I   T   V   P   N
---------------------------------------------------------E3L-------------------------------------------------------------

       2420       2430       2440       2450       2460       2470       2480       2490       2500
   *    *    *    *    *    *    *    *    *    *    *    *    *    *    *    *    *    *
AGC ATC TTT CCA ATC AAT AAT TTT TTT AGC CGG AAT AAC ATC ATC AAA AGA CTT ATG ATC CTC TCT CAT TGA TTT TTC GCG GGA TAC ATC
TCG TAG AAA GGT TAG TTA TTA AAA AAA TCG GCC TTA TTG TAG TAG TTT TCT GAA TAC TAG GAG AGA GTA ACT AAA AAG CGC CCT ATG TAG
<A   D   K   W   D   I   I   K   K   A   P   I   V   D   D   F   S   K   H   D   E   R   M   S   K   E   R   S   V   D
---------------------------------------------------------E3L-------------------------------------------------------------

       2510       2520       2530       2540       2550       2560       2570       2580       2590
   *    *    *    *    *    *    *    *    *    *    *    *    *    *    *    *    *    *
ATC TAT TAT GAC GTC AGC CAT AGC ATC AGC ATC CGG CTT ATC CGC CTC CGT TGT CAT AAA CCA ACG AGG AGG AAT ATC GTC GGA GCT GTA
TAG ATA ATA CTG CAG TCG GTA TCG TAG TCG TAG GCC GAA TAG GCG GAG GCA ACA GTA TTT GGT TGC TCC TCC TTA TAG CAG CCT CGA CAT
<D   I   I   V   D   A   M   A   D   A   D   P   K   D   A   E   T   T   M   F   W   R   P   P   I   D   D   S   S   Y
---------------------------------------------------------E3L-------------------------------------------------------------

       2600       2610       2620       2630       2640       2650       2660       2670       2680
   *    *    *    *    *    *    *    *    *    *    *    *    *    *    *    *    *    *
CAC CAT AGC ACT ACG TTG AAG ATC GTA CAG AGC TTT ATT AAC TTC TCG CTT CTC CAT ATT AAG TTG TCT AGT TAG TTG TGC AGC AGT AGC
GTG GTA TCG TGA TGC AAC TTC TAG CAT GTC TCG AAA TAA TTG AAG AGC GAA GAG GTA TAA TTC AAC AGA TCA ATC AAC ACG TCG TCA TCG
<V   M   A   S   R   Q   L   D   Y   L   A   K   N   V   E   R   K   E   M   N   L   Q   R   T   L   Q   A   A   T   A
---------------------------------------------------------E3L-------------------------------------------------------------

       2690       2700       2710       2720       2730       2740       2750       2760       2770
   *    *    *    *    *    *    *    *    *    *    *    *    *    *    *    *    *    *
TCC TTC GAT TCC AAT GTT TTT AAT AGC CGC ACA CAC AAT CTC TGC GTC AGA ACG CTC GTC AAT ATA GAT CTT AGA CAT TT TTAGAGAGAA
AGG AAG CTA AGG TTA CAA AAA TTA TCG GCG TGT GTG TTA GAG ACG CAG TCT TGC GAG CAG TTA TAT CTA GAA TCT GTA AA AATCTCTCTT
<G   E   I   G   I   N   K   I   A   A   C   V   I   E   A   D   S   R   E   D   I   Y   I   K   S   M
---------------------------------------------------------E3L--------------------------------------
```

FIG. 8F

```
      2780       2790       2800       2810       2820       2830       2840       2850       2860       2870       2880
CTAACACAAC CAGCAATAAA ACTGAACCTA CTTTATCATT TTTTTATTCA TCATCCTCTG GTGGTTCGTC GTTTCTATCG AATGTAGCTC TGATTAACCC GTCATCTATA
GATTGTGTTG GTCGTTATTT TGACTTGGAT GAAATAGTAA AAAAATAAGT AGTAGGAGAC CACCAACCAG CAAAGATAGC TTACATCGAG ACTAATTGGG CAGTAGATAT

      2890       2900       2910       2920       2930       2940       2950       2960       2970       2980       2990
GGTGATGCTG GTTCTGGAGA TTCTGGAGGA GATGGATTAT TATCTGGAAG AATCTCTGTT ATTTCCTTGT TTTCATGTAT CGATTGCGTT GTAACATTAA GATTGCGAAA
CCACTACGAC CAAGACCTCT AAGACCTCCT CTACCTAATA ATAGACCTTC TTAGAGACAA TAAAGGAACA AAAGTACATA GCTAACGCAA CATTGTAATT CTAACGCTTT

      3000       3010       3020       3030       3040       3050       3060       3070       3080       3090       3100
TGCTCTAAAT TTGGGAGGCT TAAAGTGTTG TTTGCAATCT CTACACGCGT GTCTAACTAG TGGAGGTTCG TCAGCTGCTC TAGTTTGAAT CATCATCGGC GTAGTATTCC
ACGAGATTTA AACCCTCCGA ATTTCACAAC AAACGTTAGA GATGTGCGCA CAGATTGATC ACCTCCAAGC AGTCGACGAG ATCAAACTTA GTAGTAGCCG CATCATAAGG

      3110       3120       3130       3140       3150       3160       3170       3180       3190       3200       3210
TACTTTTACA GTTAGGACAC GGTGTATTGT ATTTCTCGTC GAGAACGTTA AAATAATCGT TGTAACTCAC ATCCTTTATT TTATCTATAT TGTATTCTAC TCCTTTCTTA
ATGAAAATGT CAATCCTGTG CCACATAACA TAAAGAGCAG CTCTTGCAAT TTTATTAGCA ACATTGAGTG TAGGAAATAA AATAGATATA ACATAAGATG AGGAAAGAAT

      3220       3230       3240       3250       3260       3270       3280       3290       3300       3310       3320
ATGCATTTTA TACCGAATAA GAGATAGCGA AGGAATTCTT TTTATTGATT AACTAGTCAA ATGAGTATAT ATAATTGAAA AAGTAAAATA TAAATCATAT AATAATGAAA
TACGTAAAAT ATGGCTTATT CTCTATCGCT TCCTTAAGAA AAATAACTAA TTGATCAGTT TACTCATATA TATTAACTTT TTCATTTTAT ATTTAGTATA TTATTACTTT
```

FIG. 8G

```
      3330       3340       3350       3360       3370       3380       3390       3400       3410       3420       3430
    *    *     *    *     *    *     *    *     *    *     *    *     *    *     *    *     *    *     *    *     *    *
CGAAATATCA GTAATAGACA GGAACTGGCA GATTCTTCTT CTAATGAAGT AAGTACTGCT AAATCTCCAA AATTAGATAA AAATGATACA GCAAATACAG CTTCATTCAA
GCTTTATAGT CATTATCTGT CCTTGACCGT CTAAGAAGAA GATTACTTCA TTCATGACGA TTTAGAGGTT TTAATCTATT TTTACTATGT CGTTTATGTC GAAGTAAGTT

      3440       3450       3460       3470       3480       3490       3500       3510       3520       3530       3540
    *    *     *    *     *    *     *    *     *    *     *    *     *    *     *    *     *    *     *    *     *    *
CGAATTACCT TTTAATTTTT TCAGACACAC CTTATTACAA ACTAACTAAG TCAGATGATG AGAAAGTAAA TATAAATTTA ACTTATGGGT ATAATATAAT AAAGATTCAT
GCTTAATGGA AAATTAAAAA AGTCTGTGTG GAATAATGTT TGATTGATTC AGTCTACTAC TCTTTCATTT ATATTTAAAT TGAATACCCA TATTATATTA TTTCTAAGTA

      3550       3560       3570       3580       3590       3600       3610       3620       3630       3640       3650
    *    *     *    *     *    *     *    *     *    *     *    *     *    *     *    *     *    *     *    *     *    *
GATATTAATA ATTTACTTAA CGATGTTAAT AGACTTATTC CATCAACCCC TTCAAACCTT TCTGGATATT ATAAAATACC AGTTAATGAT ATTAAAATAG ATTGTTTAAG
CTATAATTAT TAAATGAATT GCTACAATTA TCTGAATAAG GTAGTTGGGG AAGTTTGGAA AGACCTATAA TATTTTATGG TCAATTACTA TAATTTTATC TAACAAATTC

      3660       3670       3680       3690       3700       3710       3720       3730       3740       3750       3760
    *    *     *    *     *    *     *    *     *    *     *    *     *    *     *    *     *    *     *    *     *    *
AGATGTAAAT AATTATTTGG AGGTAAAGGA TATAAAATTA GTCTATCTTT CACATGGAAA TGAATTACCT AATATTAATA ATTATGATAG GAATTTTTTA GGATTTACAG
TCTACATTTA TTAATAAACC TCCATTTCCT ATATTTTAAT CAGATAGAAA GTGTACCTTT ACTTAATGGA TTATAATTAT TAATACTATC CTTAAAAAAT CCTAAATGTC

      3770       3780       3790       3800       3810       3820       3830       3840       3850       3860       3870
    *    *     *    *     *    *     *    *     *    *     *    *     *    *     *    *     *    *     *    *     *    *
CTGTTATATG TATCAACAAT ACAGGCAGAT CTATGGTTAT GGTAAAACAC TGTAACGGGA AGCAGCATTC TATGGTAACT GGCCTATGTT TAATAGCCAG ATCATTTTAC
GACAATATAC ATAGTTGTTA TGTCCGTCTA GATACCAATA CCATTTTGTG ACATTGCCCT TCGTCGTAAG ATACCATTGA CCGGATACAA ATTATCGGTC TAGTAAAATG
```

FIG. 8H

```
       3880       3890       3900       3910       3920       3930       3940       3950       3960       3970       3980
     *     *    *     *    *     *    *     *    *     *    *     *    *     *    *     *    *     *    *     *    *     *
TCTATAAACA TTTTACCACA AATAATAGGA TCCTCTAGAT ATTTAATATT ATATCTAACA ACAACAAAAA AATTTAACGA TGTATGGCCA GAAGTATTTT CTACTAATAA
AGATATTTGT AAAATGGTGT TTATTATCCT AGGAGATCTA TAAATTATAA TATAGATTGT TGTTGTTTTT TTAAATTGCT ACATACCGGT CTTCATAAAA GATGATTATT

       3990       4000       4010       4020       4030       4040       4050       4060       4070       4080       4090
     *     *    *     *    *     *    *     *    *     *    *     *    *     *    *     *    *     *    *     *    *     *
AGATAAAGAT AGTCTATCTT ATCTACAAGA TATGAAAGAA GATAATCATT TAGTAGTAGC TACTAATATG GAAAGAAATG TATACAAAAA CGTGGAAGCT TTTATATTAA
TCTATTTCTA TCAGATAGAA TAGATGTTCT ATACTTTCTT CTATTAGTAA ATCATCATCG ATGATTATAC CTTTCTTTAC ATATGTTTTT GCACCTTCGA AAATATAATT

       4100       4110       4120       4130       4140       4150       4160       4170       4180       4190       4200
     *     *    *     *    *     *    *     *    *     *    *     *    *     *    *     *    *     *    *     *    *     *
ATAGCATATT ACTAGAAGAT TTAAAATCTA GACTTAGTAT AACAAAACAG TTAAATGCCA ATATCGATTC TATATTTCAT CATAACAGTA GTACATTAAT CAGTGATATA
TATCGTATAA TGATCTTCTA AATTTTAGAT CTGAATCATA TTGTTTTGTC AATTTACGGT TATAGCTAAG ATATAAAGTA GTATTGTCAT CATGTAATTA GTCACTATAT

       4210       4220       4230       4240       4250       4260       4270       4280       4290       4300       4310
     *     *    *     *    *     *    *     *    *     *    *     *    *     *    *     *    *     *    *     *    *     *
CTGAAACGAT CTACAGACTC AACTATGCAA GGAATAAGCA ATATGCCAAT TATGTCTAAT ATTTTAACTT TAGAACTAAA ACGTTCTACC AATACTAAAA ATAGGATACG
GACTTTGCTA GATGTCTGAG TTGATACGTT CCTTATTCGT TATACGGTTA ATACAGATTA TAAAATTGAA ATCTTGATTT TGCAAGATGG TTATGATTTT TATCCTATGC

       4320       4330       4340       4350       4360       4370       4380       4390       4400       4410       4420
     *     *    *     *    *     *    *     *    *     *    *     *    *     *    *     *    *     *    *     *    *     *
TGATAGGCTG TTAAAAGCTG CAATAAATAG TAAGGATGTA GAAGAAATAC TTTGTTCTAT ACCTTCGGAG GAAAGAACTT TAGAACAACT TAAGTTTAAT CAAACTTGTA
ACTATCCGAC AATTTTCGAC GTTATTTATC ATTCCTACAT CTTCTTTATG AAACAAGATA TGGAAGCCTC CTTTCTTGAA ATCTTGTTGA ATTCAAATTA GTTTGAACAT

       4430
     *     *
TTTATGAAGG TACC
AAATACTTCC ATGG
```

VECTORS HAVING ENHANCED EXPRESSION, AND METHODS OF MAKING AND USES THEREOF

RELATED APPLICATIONS

Reference is made to the concurrently filed application of Tartaglia et al., Ser. No. 08/815,809. Reference is also made to the copending applications of Paoletti et al., Ser. Nos. 08/417,210, 08/303,275, 08/709,209, 08/184,009 (incorporating by reference Ser. Nos. 07/805,567, from which U.S. Pat. No. 5,378,457 issued) and 08/521,016 and to U.S. Pat. Nos. 5,378,457, 5,225,336, 5,453,364, 5,494,807, 5,505,941, and 5,110,587, all of which patents and applications are incorporated herein by reference.

FIELD OF THE INVENTION

The present invention relates to enhanced vectors, and methods for making and using them. The vectors can have enhanced transcription or translation or enhanced transcription and translation and/or expression, e.g., enhanced transcription or translation or transcription and translation and/or expression from a nucleotide sequence of interest.

Several publications are referenced in this application. Full citation to these publications is found where cited or at the end of the specification, immediately preceding the claims or where the publication is mentioned; and each of these publications is hereby incorporated by reference. These publications relate to the state of the art to which the invention pertains; however, there is no admission that any of these publications is indeed prior art.

BACKGROUND OF THE INVENTION

DNA such as plasmids or naked DNA, and other vectors, such as viral vectors, e.g., vaccinia virus and more recently other poxviruses, have been used for the insertion and expression from foreign genes. The basic technique of inserting foreign genes into live infectious poxvirus involves recombination between pox DNA sequences flanking a foreign genetic element in a donor plasmid and homologous sequences present donor plasmid and homologous sequences present in the rescuing poxvirus (Piccini et al., 1987). Recombinant poxviruses are constructed in steps known as in or analogous to methods in U.S. Pat. Nos. 4,769,330, 4,772,848, 4,603,112, 5,505,941, and 5,494,807, incorporated herein by reference. A desire in vector development is attenuated vectors, e.g., for enhanced safety; for instance, so that the vector may be employed in an immunological or vaccine composition.

For instance, the NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen. Likewise, the ALVAC vector, a vaccine strain of canarypox virus, has also proven effective as a recombinant viral vaccine vector (Perkus et al., 1995). In non-avian hosts, both these vectors do not productively replicate (with some exceptions as to NYVAC). Since all poxviruses replicate in the cytoplasm and encode most, if not all of the proteins required for viral transcription (Moss 1990), appropriately engineered foreign coding sequences under the control of poxvirus promoters are transcribed and translated in the absence of productive viral replication.

It would be an improvement over the state of the art to provide enhanced vectors, e.g., vectors having enhanced transcription or translation or transcription and translation and/or expression, for instance such vectors which are attenuated; especially since attenuation may raise issues of expression levels and/or persistence, and it would be an advancement to address such issues.

OBJECTS AND SUMMARY OF THE INVENTION

Recent studies on vaccinia replication have revealed certain poxvirus-encoded functions which play a role in the regulation of viral transcription and translation (reviewed in Moss, 1990; Moss, 1992). Some of these vaccinia encoded functions (e.g., E3L, K3L, H4L, and combinations thereof) have now surprisingly been utilized to increase the levels and persistence of gene expression (e.g., foreign gene expression) in vectors (e.g., the NYVAC and ALVAC vectors); and, are exemplary of the inventive vectors and methods.

Objects of the present invention may include at least one of: providing a method for increasing transcription or translation or transcription and translation and/or expression from at least one nucleotide sequence of interest by a vector, such as a coding nucleotide sequence by a vector; a vector having enhanced transcription or translation or transcription and translation; providing a method for preparing a vector having enhanced transcription or translation or transcription and translation and/or expression; providing a method for enhancing transcription or translation or transcription and translation and/or expression from a vector; providing an improved vector, such as poxvirus vectors, e.g., improved NYVAC, ALVAC or TROVAC vectors; and, products therefrom.

The invention thus provides a vector for enhanced expression of at least one first nucleotide sequence. The vector is modified to comprise at least one second nucleotide sequence encoding a transcription factor or translation factor or a transcription factor and a translation factor. The vector also can be modified to comprise the first nucleotide sequence. There is substantially co-temporal or substantially contemporaneous expression from the first and second nucleotide sequences. The expression is in a cell having a particular phenotype, and preferably the expression of the first and second nucleotide sequences is with respect to the phenotype of the cell. Thus, expression of the second nucleotide sequence enhances expression of the first nucleotide sequence by enhancing transcription or translation or transcription and translation.

The first nucleotide sequence can be operably linked to a first promoter and the second nucleotide sequence can be operably linked to a second promoter, and the first and second promoters are preferably functional substantially co-temporally or contemporaneously. Thus, the first and second nucleotide sequences can be at different loci within the vector. The first and second nucleotide sequences also can be at the same locus within the vector, using the first and second promoters; or, by the first nucleotide sequence and the second nucleotide sequence being operably linked to a promoter.

The transcription factor can be of poxvirus origin, e.g., from a vaccinia virus. The transcription factor can be from an open reading frame selected from the group consisting of H4L, D6, A7, G8R, A1L, A2L, H5R, and combinations thereof. The translation factor can effect inhibition of eIF-2α phosphorylation or inhibition of PKR phosphorylation or otherwise sequester dsRNA which actually increases the concentration required to activate PKR. The translation factor can be selected from the group consisting of: a K3L open reading frame, an E3L open reading frame, a viral associated RNA I (VAI), an EBER RNA, a sigma 3 open reading frame, a TRBP open reading frame, and combinations thereof.

The first nucleotide sequence can be exogenous, e.g., encoding an epitope of interest, a biological response modulator, a growth factor, a recognition sequence, a therapeutic gene, a fusion protein or combinations thereof.

The vector can be a recombinant virus, such as a poxvirus; for instance, an orthopoxvirus or an avipoxvirus, e.g., a vaccinia virus, a fowlpox virus, a canarypox virus; preferably an attenuated virus such as an attenuated poxvirus, e.g., NYVAC, ALVAC, or TROVAC.

The invention further provides a method for preparing a an inventive vector comprising modifying the vector to comprise the at least one second nucleotide sequence. The method can also include modifying the vector so that it comprises at the at least one first nucleotide sequence. Preferably the vector is so modified that there is substantially co-temporal or contemporaneous expression of the first and second nucleotide sequences; and, more preferably, the vector is also so modified that the expression is with respect to the phenotype of the cell.

The method can comprise operably linking the first nucleotide sequence to a first promoter and the second nucleotide sequence to a second promoter, wherein the first and second promoters are functional substantially co-temporally or contemporaneously. The method can also comprise operably linking the first and second nucleotide sequences to a promoter.

The invention further provides an immunological, vaccine or therapeutic composition comprising at least one inventive vector and a pharmaceutically acceptable carrier or diluent.

The invention even still further provides a method for generating an immunological or therapeutic response in a host (animal, human, vertebrate, mammal, etc.) comprising administering to the host at least one inventive composition.

The invention additionally provides a method for increasing expression of at least one first nucleotide sequence by a vector comprising the first nucleotide sequence. The method comprises modifying the vector to comprise at least one second nucleotide sequence encoding a transcription factor or a translation factor or a transcription factor and a translation factor. There is preferably substantially co-temporal or contemporaneous expression of the first and second nucleotide sequences. Expression can be in a cell having a particular phenotype; and it is more preferred to have expression be with respect to the phenotype of the cell. Expression of the second nucleotide sequence enhances expression of the first nucleotide sequence by enhancing transcription or translation or transcription and translation. The method can additionally comprise modifying the vector to comprise the first nucleotide sequence of interest.

The invention in yet another embodiment provides a method for expressing at least one gene product in vitro comprising infecting, or transfecting, a suitable cell with at least one inventive vector. The products therefrom can be an immunogen or epitope of interest, which can be useful in formulating therapeutic, immunological or vaccine compositions; or, for generating antibodies such as monoclonal antibodies; or, in assays, kits, tests and the like, such as diagnostic compositions, e.g., for detection of antibodies.

Thus, the invention can provide compositions and methods for in vitro transcription or translation or transcription and translation and/or expression involving at least one inventive vector, e.g., methods for producing a gene product (which can be used as an immunogen or epitope in a therapeutic, immunological or vaccine composition, or in a diagnostic or detection kit, assay or method, e.g., to ascertain the presence or absence of antibodies, or to generate antibodies, such as monoclonal antibodies, e.g., for use in a diagnostic or detection kit, assay or method), and/or for ex vivo transcription or translation or transcription and translation and/or expression involving at least one inventive vector, e.g., methods for producing a gene product for stimulating cells for reinfusion into a host (e.g., animal, mammal, vertebrate, human).

Additionally, in a further embodiment the invention provides a method for expressing at least one nucleotide sequence (e.g., the at least one first nucleotide sequence) in vivo comprising administering at least one inventive vector to a host (human, animal, vertebrate, mammal, etc.). The nucleotide sequence can encode an immunogen or epitope of interest. The method can obtain antibodies. From generating antibodies one can generate monoclonal antibodies; or, antibodies are useful in assays, kits, tests or diagnostic compositions, e.g., for detection of antigens.

The invention can thus provide methods and compositions for in vivo transcription or translation or transcription and translation and/or expression involving the inventive vectors, e.g., administering at least one inventive vector or a composition comprising at least one inventive vector, for instance, therapeutic, immunological or vaccine compositions comprising at least one inventive vector and a suitable carrier or diluent (e.g., suitable for veterinary and human medicine).

These and other embodiments are disclosed or are obvious from and encompassed by, the following Detailed Description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which:

FIG. 1 (FIGS. 1A, 1B, 1C) shows the nucleotide sequence of the insert in vP1380 containing the mutagenized H4L orf and lacZ orf under the H6 promoter (SEQ ID NO: 1);

FIG. 2 (FIGS. 2A, 2B) shows the nucleotide sequence of the ALVAC C8 Insertion site containing the H6/H42 expression cassette (SEQ ID NO: 2);

FIG. 3 (FIGS. 3A, 3B) shows the nucleotide sequence of the ALVAC C6 insertion site containing the H6/K3L and E3L expression cassette (SEQ ID NO: 3);

FIG. 4 (FIGS. 4A, 4B) shows the DNA sequence of the coding region of FHV gB with modified T5NT motifs (SEQ ID NO: 4);

FIG. 5 (FIGS. 5A, 5B, 5C) shows the DNA sequence of the H6 promoted FHV gB donor plasmid pC3H6FHVB (SEQ ID NO: 5);

FIGS. 6 (FIGS. 6A, 6B, 6C; FIGS. 7A, 7B, 7C, 7D, 7E, 7F, 7G) and 7 show DNA (SEQ ID NOS: 6 and 7), and amino acid sequences (SEQ ID NOS: 43, 44, 45 and 46) of inserts in vCP1433 and vCP1452; and FIG. 8 (FIGS. 8A, 8B, 8C, 8D, 8E, 8F, 8G, 8H) shows the DNA sequence (SEQ ID NO: 8) and amino acid sequences (SEQ ID NOS: 47 and 48) of K3L E3L in vCP1452.

DETAILED DESCRIPTION

U.S. Pat. No. 5,494,807, to Paoletti et al., hereby incorporated herein by reference, relates to a modified recombinant virus having inactivated virus-encoded genetic functions so that the recombinant virus has attenuated virulence and enhanced safety. The viruses disclosed in Paoletti et al. can be poxviruses, e.g., a vaccinia virus or an avipox virus, such as fowlpox virus and canarypox virus, e.g., NYVAC, ALVAC and TROVAC. ALVAC was deposited under the terms of the Budapest Treaty with the American Type Culture Collection (ATCC), 12301 Parklawn Drive, Rockville, Md., 20852, USA, ATCC accession number VR-2547. TROVAC was likewise deposited under the terms of the Budapest Treaty with the ATCC, accession number 2553. And, NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATC-97913, ATCC-97912, and ATC-97914, respectively.

Like the Paoletti et al. issued U.S. Patent, Falkner et al., WO 95/30018, published Nov. 9, 1995, based on U.S. application Ser. No. 08/235,392, filed Apr. 24, 1994 (both incorporated herein by reference), relates to poxviruses wherein loci for genetic functions associated with virulence (i.e., loci for "essential" functions) are employed for insertion of exogenous DNA.

Further, recombinants can be made from early ($DNA^-$) and late defective mutants (see Condit and Niles, "Orthopoxvirus Genetics," pp 1–39, In: *Poxviruses*, Edited by R. W. Moyer and P. C. Turner (Springer-Verlag, 1990), and documents cited therein, hereby incoporated herein by reference)), or from MVA which is said to be abortive late. Recombinants from defective mutants, abortive late viruses, viruses having essential genetic functions deleted or interrupted, or viruses having expression without productive replication (e.g., ALVAC in mammalian systems) may be said to be attenuated.

Certain vectors, such as attenuated vectors, e.g., NYVAC and ALVAC vectors, are blocked or limited in late gene expression in mammalian cells. Thus, early promoters are routinely employed in such vectors, e.g., NYVAC- or ALVAC-based recombinants, for expression from the foreign gene products.

Vaccinia encodes an open reading frame (ORF) designated H4L which has been shown to be required for early viral transcription (Ahn and Moss 1992, Zhang et al, 1994). The H4L ORF encodes an essential protein of 94 kDa which is expressed after the start of viral DNA replication (late function). The H4L protein has been found to be tightly associated with the viral RNA polymerase complex and is believed to act in conjunction with the vaccinia early transcription factor (VETF) to initiate and transcribe early viral message (Ahn and Moss, 1992).

H4L is expressed late, but required early. This is consistent with the protein being packaged in the viral particles similar to that which is observed with VETF. This suggested that the amount of H4L present at early times post infection is low and perhaps limiting. Hence, one approach to increase foreign gene expression in an abortive, early vector-, e.g., virus-host interaction would be to increase the amount of H4L protein available during the early phase by expressing the H4L ORF using a vaccinia early/late promoter rather than the endogenous late promoter. Early expression from H4L may not only increase the level of foreign gene transcripts, but also increase levels of other vaccinia early genes (e.g. E3L) which may also increase total protein levels.

There are other viral transcription factors; for instance, early and/or late viral transcription factors of poxvirus origin; e.g., from: vaccinia D6, vaccinia A7, vaccinia G8R, vaccinia A1L, vaccinia A2L, or vaccinia H5R (VLTF-1, -2, -3, -4, P3, VLTF-X; see Kovacs et al., J. Virology, October 1996, 70(10):6796–6802, and documents cited therein, incorporated herein by reference). These and other transcription factors, and nucleotide sequences therefor or for homologs thereof, e.g., from another poxvirus, are useful in the practice of the invention.

The selection of a suitable transcription factor is within the ambit of the skilled artisan from this disclosure and knowledge in the art; for instance, the skilled artisan can select a transcription factor based on an abortive phenotype of the vector, e.g., MVA is said to be abortive late, and a late or early or early/late transcription factor may be employed with this vector; ALVAC is abortive early and an early or early/late transcription factor may be employed with this vector; and, the vector can also be a ts (temperature sensitive) mutant (with respect to early ($DNA^-$) and late defective mutants which can be also used in the practice of this invention, reference is made to Condit and Niles, supra). Thus, it is preferred that the transcription and/or translation factor and the at least one nucleotide sequence of interest be expressed early, late (including intermediate), or early/late, relative to the phenotype of the vector.

Another means to increase foreign gene expression involves enhancing the overall efficiency of translation, e.g., mRNA translation, such as viral mRNA translation. Two vaccinia encoded functions (E3L and K3L) have recently been identified as playing a role in the regulation of viral translation (Beattie et al., 1995a, 1995b, 1991; Chang et al., 1992; Davies et al., 1993). Both are capable of inhibiting the action of a cellular protein kinase (PKR) which, when activated by double stranded RNA (dsRNA), phosphorylates the translational initiation factor eIF-2$\alpha$, leading to an inhibition of initiation of mRNA translation (reviewed in Jacobs and Langland, 1996). Vaccinia virus, which produces dsRNA during viral transcription, has thus evolved mechanisms to block the negative action of PKR on eIF-2$\alpha$ and allow for efficient translation of viral mRNA. (Asymetric transcription gives rise to dsRNA; any viral infection or plasmid derived expression gives rise to it; dsRNA activates PKR; PKR becomes autophosphorylated, leading to phosphorylation of eIF-2$\alpha$.)

The vaccinia K3L ORF has been shown to have significant amino acid homology to eIF-2$\alpha$ (Goebel et al., 1990; Beattie et al., 1991; U.S. Pat. No. 5,378,457; see also Beattie et al., 1995a, 1995b). This protein is believed to act as a pseudosubstrate for PKR and competes for the eIF-2$\alpha$ binding site (Carroll et al., 1993; Davies et al., 1992). The K3L gene product can bind to activated PKR and thus prevent phosphorylation of eIF-2$\alpha$ with its resultant negative effect on translation initiation.

The vaccinia E3L gene codes for a protein which is capable of specifically binding to dsRNA (Watson and Jacobs, 1991; Chang et al., 1992). This would tend to lower the amounts of dsRNA in the infected cell, and thus reduce the level of activated PKR. When E3L was deleted from vaccinia, the resulting virus lost this kinase inhibitory function and further allowed activation of the 2' 5' oligoadenylate synthetase/RNase L pathway resulting in increased degradation of rRNA (Beattie et al., 1995a, 1995b). Thus, E3L appears to be critical for efficient mRNA translation in vaccinia infected cells at two levels; mRNA stability and limiting eIF-2$\alpha$ phosphorylation.

The ALVAC genome has been sequenced and searched for any homology to E3L/K3L or to any known dsRNA binding motif. Results have revealed no significant homology of any ALVAC ORFS to these two vaccinia ORFs, nor the presence of any dsRNA binding motifs.

Thus, an approach to improving expression levels in recombinant ALVAC vectors was to express the vaccinia E3L/K3L ORFs in ALVAC under the control of early vaccinia promoters. Through inhibition of PKR in the infected cells, the levels and persistence of foreign gene expression could be enhanced.

Hence, NYVAC and ALVAC recombinants as discussed herein were generated in order to enhance foreign gene expression at the transcriptional or translational or transcriptional and translational levels, as examples of the vectors and methods of the present invention.

Thus, exemplified herein is NYVAC recombinants having an early expressed H4L ORF and ALVAC recombinants having expression from the vaccinia E3L/K3L genes for enhancing or increasing the levels or persistence of expression of an inserted foreign gene. The up-regulation of foreign gene expression can have a profound effect on the induction of a therapeutic or immunological response in a host administered or inoculated with recombinants derived from these new vectors, thereby leading to an enhanced immunological, e.g., protective, response, or an enhanced therapeutic response.

The scope of the invention, i.e., to manipulate expression from any of a transcription and/or translation factor, e.g., H4L, E3L and K3L, to thereby enhance transcriptional or translational or transcriptional and translational and/or expression efficiency, can be extended to other eukaryotic vector systems (i.e. DNA, viruses).

In fact, viruses in other families have also evolved mechanisms to overcome the cellular anti-viral response of translational down-regulation through PKR activation. In adenoviruses, the VAI RNA, transcribed by RNA pol III, has been well characterized and shown to bind directly to PKR, and thus, prevent its activation by dsRNA (Mathews and Shenk, 1991). Deletion of VAI from the adenovirus genome results in a mutant that replicates poorly and is deficient in levels of late gene expression (Thimmappaya et al., 1982). Similarly, Epstein-Barr virus, a herpesvirus, has an analogous RNA, called EBER, which also acts to prevent PKR activation by directly binding to the kinase (Clark et al., 1991; Sharp et al., 1993). The reovirus sigma 3 gene product has been shown to act in a similar manner as vaccinia E3L in binding dsRNA and thus preventing activation of PKR (Imani and Jacobs, 1988; see also Beattie et al. 1995a). Indeed, one study has shown that the reovirus sigma 3 gene can partially compensate a vaccinia recombinant deleted of E3L (Beattie et al., 1995a). Further, a cellular protein activated upon HIV infection (TRBP) has been shown to inhibit the activity of PKR (Park et al., 1994).

Thus, the present invention broadly relates to manipulation of expression, preferably by employing at least one transcription factor, e.g., at least one early and/or late viral transcription factor, or at least one translation factor, e.g., a nucleotide sequence encoding a product for overcoming the cellular anti-viral response of translational down-regulation through PKR activation in any eukaryotic vector system, or at least one trancription factor and at least one translation factor; for instance, to increase or enhance expression. And, the invention can pertain to any vector system, including, plasmid or naked DNA vectors, viral vectors, such as poxvirus, adenovirus, herpesvirus, baculovirus, and the like. Thus, the nucleotide sequences can be RNA or DNA, for instance, as is suitable in view of the vector system.

Accordingly, the invention can relate to a vector modified to comprise at least one nucleotide sequence encoding at least one transcription factor, at least one translation factor, or at least one transcription factor and at least one translation factor; a method for increasing transcription and/or translation and/or expression by a vector or for preparing an inventive vector, e.g., by modifying the vector to comprise the at least one nucleotide sequence.

These methods can include substantially co-temporal expression from: (i) a first nucleotide sequence comprising at least one nucleotide sequence of interest, and (ii) a second nucleotide sequence comprising at least one nucleotide sequence encoding a transcription factor, or at least one nucleotide sequence encoding a translation factor or at least one nucleotide sequence encoding a transcription factor and a translation factor. The vector also can be modified to comprise the at least one nucleotide sequence of interest. The at least one nucleotide sequence of interest can be at least one coding nucleotide sequence. The vector preferably has substantially co-temporal or contemporaneous expression of the first and second nucleotide sequences.

The substantially co-temporal expression can occur by employing promoters for the first and second nucleotide sequences which are functional at approximately the same time or stage of infection. Thus, the nucleotide sequence of interest and the nucleotide sequences encoding the factor(s) can be positioned at different loci in the vector. Alternatively, substantially co-temporal expression can occur by positioning the first and second nucleotide sequences within the same loci. Thus, substantially co-temporal expression can occur by operably linking to the nucleotide sequence of interest and/or to a promoter operably linked to the nucleotide sequence of interest, a nucleotide sequence encoding a transcription factor, a nucleotide sequence encoding a translation factor, or a nucleotide sequence encoding a transcription factor and a translation factor.

The transcription factor can be from any suitable system. Preferably, the transcription factor is of poxvirus origin, e.g., from a vaccinia virus. The transcription factor can be from expression from an open reading frame selected from the group consisting of H4L, D6, A7, G8R, A1L, A2L, H5R, a homolog thereof and combinations thereof. It is also preferred that embodiments including a nucleotide sequence encoding a transcription factor comprise a poxvirus vector system.

The translation factor can likewise be from any suitable system. Preferably the translation factor can effect inhibition of eIF-2α phosphorylation or inhibition of PKR phosphorylation or otherwise decreases cellular dsRNA content which increases the effective concentration of dsRNA. The translation factor can be selected from expression from the group consisting of: a K3L open reading frame, an E3L open reading frame, a VAI RNA, an EBER RNA, a sigma 3 open reading frame, a TRBP open reading frame, a homolog thereof, and combinations thereof. The term "effective" with respect to dsRNA concentration means the amount of dsRNA to activate PKR and/or eIF-2α phosphorylation (the dsRNA being in a form therefor). With respect to RNA-based factors, e.g., VAI RNA, EBER RNA, the skilled artisan can obtain suitable DNA from the RNA for use in a DNA vector system without undue experimentation. And, with respect to DNA-based factors, the skilled artisan can obtain suitable RNA therefrom for use in a RNA vector system, without undue experimentation.

The term "substantially co-temporal expression" or the term "substantially contemporaneous expression" means that the nucleotide sequence(s) encoding the transcription or translation or transcription and translation factor(s) are expressed during approximately the same stage of infection as is the at least one nucleotide sequence of interest.

For instance, poxvirus genes are regulated in a temporal manner (Coupar, et al., Eur. J. Immunol., 1986, 16:1479–1487, at 1479). Thus, immediately after infection, a class of "early" genes is expressed (Id.). "Early genes" cease being expressed (i.e., early promoters cease functioning) at a time after infection prior to the "later" stage of infection (DNA replication commencement). The thymidine kinase ("TK") gene and TK promoter is an example of an immediate "early" gene and promoter (Hruby et al., J. Virol., 1982, 43(2):403–409, at 403). The TK gene is switched "off" about four hours after infection.

"Late genes" are a class of genes not expressed until DNA replication has commenced (Coupar et al., supra). The PL11 promoter employed by Coupar et al. is an example of a "late" promoter. Thus, in Coupar et al., HA gene expression regulated by the PL11 promoter was not until after DNA replication, despite being in the TK region.

In contrast to canonical "early" genes and "late" genes the 7.5 kD gene and 7.5 kD promoter, is an example of an "early and late" gene and promoter. An "apparent exception to regulated transcription" (Davison and Moss, "Structure of Vaccinia Virus Early Promoters" J. Mol. Biol., 210–69, 249–69 (1989) at 749), the 7.5 kD promoter "contains regulatory signal for both early and late transcription" (Coupar et al., supra). Indeed, there are "independent early and late RNA start sites within the promoter region of the 7.5-kD gene" (Cochran et al., J. Virol., 59(1): 30–37 (April, 1985).

Coupar et al. observed "that temporal regulation of HA expression by the promoters PF [early], P7.5 [early and late] and PL11 [late] was maintained when the promoters were transposed to interrupt the TK gene of [vaccinia virus]" (Id., at 1482). That is, Coupar et al. observed that foreign gene expression under the control of an early vaccinia promoter occurred "early", foreign gene expression under control of a late vaccinia promoter occurred "late", and foreign gene expression under the control of the early and late vaccinia 7.5 kD promoter occurred both early and late (See also id. at 1479: "[p]romoter sequences transposed to within the thymidine kinase (TK) gene continue to function in a temporally regulated manner" (citations omitted)).

Thus, the nucleotide sequence(s) encoding the transcription or translation or transcription and translation factor(s) can be under the control of a first type of promoter and the at least one nucleotide sequence of interest or the coding nucleotide sequence can be under the control of a second type of promoter, wherein the first and second promoters are both early, both late (including intermediate), or both early and late; or, the first promoter can be early or late and the second promoter early and late; or the first promoter can be early and late and the second promoter early or late. The nucleotide sequence of interest and the nucleotide sequence (s) encoding the transcription or translation or transcription and translation factor(s) can be at the same locus or at different loci; or under the control of the same promoter.

Accordingly, the invention can relate to a method for preparing a vector having enhanced transcription or translation or transcription and translation and/or expression, or to a method for increasing or enhancing transcription or translation or transcription and translation and/or expression in a vector comprising operably linking to at least one nucleotide sequence of interest, or to a promoter operably linked thereto, at least one nucleotide sequence for at least one transcription and/or at least one translation factor; e.g., at least one nucleotide sequence for a transcription transcription factor, or at least one nucleotide sequence for a translation factor or at least one nucleotide sequence for a transcription factor and a translation factor. Preferably the translation factor effects an inhibition of eIF-2α phosphorylation and/or effects an inhibition of phosphorylation of PKR and/or a cellular kinase responsible for phosphorylation of eIF-2α and/or effects the effective concentration of dsRNA. The invention also can thus relate to vectors from such methods.

Alternatively, the inventive methods can comprise operably linking at least one nucleotide sequence of interest to a first type of promoter and operably linking at least one second nucleotide sequence encoding at least one transcription and/or translation factor to a second type of promoter, within a vector, wherein the first and second promoters are both functional at the same time or same stage of infection, e.g., the first and second promoters are both early, both late (including intermediate), or both early and late; or, the first promoter is early or late and the second promoter is early and late; or the first promoter is early and late and the second promoter is early or late. Of course, the first and second promoters can be the same promoter at two or more different loci, or the same promoter at one locus. And, the invention thus relates to vectors from such methods.

And, the term "nucleotide sequence" as used herein can mean nucleic acid molecule. Thus, a nucleotide sequence can be an isolated nucleic acid molecule, e.g., exogenous DNA.

Accordingly, the present invention can provide vectors modified to contain at least one exogenous nucleotide sequence, preferably encoding at least one epitope of interest, and at least one transcription factor or at least one translation factor or at least one transcription factor and at least one translation factor, wherein there is substantially temporal co-expression (or substantially co-temporal expression or substantially contemporaneous expression) of the exogenous nucleotide sequence and the factor(s); and, methods for making and using such vectors and products therefrom. Enhanced or improved expression is obtained by the vectors and methods of the invention; and, enhanced or improved expression can mean enhanced levels and/or persistence of expression.

The invention can thus provide vectors, for instance, poxvirus vectors, which are abortive early, e.g., NYVAC, ALVAC or TROVAC recombinants, having an early expressed transcription factor, e.g., an early expressed H4L open reading frame (or a homolog thereof, e.g., from another vector system, such as poxviruses other than vaccinia, herpesvirus, such as Epstein-Barr, adenovirus, plasmid or naked DNA, and the like) as a means for enhancing and/or increasing the levels and/or persistence of an inserted nucleotide sequence, e.g., a foreign gene. The invention can also provide vectors, for instance, poxvirus vectors, which are abortive late (which includes abortive intermediate), e.g., MVA recombinants, having a late expressed transcription factor, e.g., an expressed G8R, A1L, A2L, H5R (VLTF-1, -2, -3, -4, P3, VLTF-X) open reading frame (or a homolog thereof, e.g., from another vector system, such as poxviruses other than vaccinia, herpesvirus, such as Epstein-Barr, adenovirus, plasmid or naked DNA, and the like) as a means for enhancing and/or increasing the levels and/or persistence of expression from an inserted nucleotide sequence, e.g., a foreign gene.

The invention can additionally provide vectors, for instance, poxvirus vectors, e.g., NYVAC, ALVAC or TRO- VAC recombinants, having expression from the vaccinia E3L and/or K3L (or a homolog thereof, e.g., from another vector system, such as poxviruses other than vaccinia, herpesvirus, such as Epstein-Barr, adenovirus, plasmid or naked DNA, and the like, note discussion supra of viral mechanisms to overcome the cellular anti-viral response of translational down-regulation through PKR activation) as a means for enhancing and/or increasing the levels and persistence of an inserted nucleotide sequence, e.g., a foreign gene.

Even further still, the invention can provide vectors, for instance, poxvirus vectors, e.g., NYVAC, ALVAC or TROVAC recombinants, having an early expressed transcription factor, e.g., an early expressed H4L open reading frame (or a homolog thereof) and/or a late expressed transcription factor, e.g., an expressed G8R, A1L, A2L, H5R (VLTF-1, -2, -3, -4, P3, VLTF-X) (or a homolog thereof), for instance abortive late (which includes abortive intermediate), e.g., MVA, recombinants, and expression from the vaccinia E3L and/or K3L (or a homolog thereof) as a means for enhancing and/or increasing the levels and persistence of expression from an inserted nucleotide sequence, e.g., a foreign gene.

As shown in the Examples below, ALVAC-HIV recombinant vCP1452 containing the K3L/E3L factors had enhanced expression on human cells in comparison to vCP1433 or vCP300. Indeed, enhanced expression is observed with the E3L/K3L translational factors in human and canine cells.

Enhanced expression by translational factors such as E3L/K3L may be cell type dependent. For instance, while enhanced expression with E3L/K3L is observed in human and canine cells it is not observed in murine and feline cells. From this disclosure and the knowledge in the art, the skilled artisan can select an appropriate translational factor for use with a particular cell type, without undue experimentation. For example, it should go without saying that the skilled artisan knows the differences between cells. Thus it is preferred that the translational factor be expressed in a cell in which enhanced expression is observed, e.g., that the translational factor employed be with respect to the cell.

Further, preliminary immunogenicity studies in mice show no evidence of enhanced immunogenicity by the E3L/K3L translational factor. This corresponds to no observed enhanced expression in murine cells. Accordingly, the skilled artisan from this disclosure and the knowledge in the art can select a translational factor which will provide enhanced immunogenicity in a desired animal, without undue experimentation. If enhanced expression is observed in vitro in a particular cell line by a particular translational factor, e.g., E3L/K3L in human or canine cells, the skilled artisan can thus expect enhanced immunogenicity in vivo in the animal (including human) from which the cells were derived by that particular translational factor, e.g., enhanced immunogenicity in humans and canines from the E3L/K3L translational factor.

Furthermore, in murine cells, the limiting factor of ALVAC expression is at the transcription level. Accordingly, use of an appropriate transcription factor can overcome the inability to observe enhanced expression in the murine system. Thus, the origin of the cell may be a factor in in vitro or in vivo applications of the invention (note H4 data), as may be the nature of the vector, e.g., the phenotype of the vector; but, appropriate selection of a cell and vector phenotype and of time of expression from factor(s) and foreign and/or exogenous DNA are within the ambit of the skilled artisan, from this disclosure and the knowledge in the art, without undue experimentation.

Also, the Examples below show that NYVAC recombinant vP1380 has enhanced expression levels in comparison to vP994. Possibly, part of the enhanced levels in vP1380 are due to enhanced transcription and expression from viral specific products such as E3L, such that there is enhanced transcription and translation involved in expression in vP1380. There is more expression from the exogenous DNA and at more persistent levels in vP1380, in accordance with the invention wherein vectors obtain greater levels of expression and more persistent levels of expression.

Enhanced expression profiles in the murine system provided enhanced immunogenicity in mice, as shown by vP1380 being more immunogenic in mice than vP994. Another observation is that enhancement profiles are seen in restrictive early cells in the abortive early NYVAC recombinants herein, whereas the profiles were not observed in cells where there was productive replication, e.g., VERO or CEF, suggesting that it may be preferred that the factor and the foreign DNA be expressed substantially co-temporally or contemporaneously, i.e., that preferably there be co-expression at substantially the same time or stage, and that the time of expression, e.g., early, late, early and late, should be matched with the phenotype of the vector (e.g., abortive early, abortive late), i.e., that in a system in which viral replication is not impaired (a permissive system) or in a system in which replication is aborted at a time when expression is not matched with the phenotype of the vector may not obtain optimal expression. Thus, in an abortive early system such as ALVAC or NYVAC, one preferably expresses exogenous DNA and the transcriptional or translational or transcriptional and translational factor(s) early; in an abortive late system, one preferably expresses exogenous DNA and the transcriptional or translational or transcriptional and translational factor late or early and late (as expression only early may be akin to expression in a permissive system, i.e., one may not necessarily obtain optimal expression).

The methods for making a vector or recombinant can be by or analogous to the methods disclosed in U.S. Pat. Nos. 4,603,112, 4,769,330, 5,174,993, 5,505,941, 5,338,683, 5,494,807, and 4,722,848, WO 95/30018, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirusbased expression vectors: Strategies and applications," PNAS USA 93:11371–11377, October 1996, Kitson et al., J. Virol. 65, 3068–3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591,639, 5,589,466, and 5,580,859 relating to DNA expression vectors, inter alia. See also U.S. application Ser. Nos. 08/675,566 and 08/675,556, relating to vectors, including adenovirus vectors.

As to the inserted nucleic acid molecule in a vector of the invention, e.g., the foreign gene, the heterologous or exogenous nucleic acid molecule, e.g., DNA, in vectors of the instant invention, preferably encodes an expression product comprising: an epitope of interest, a biological response modulator, a growth factor, a recognition sequence, a therapeutic gene or a fusion protein. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, *Molecular Cloning, A Laboratory Manual*, 2nd Ed., Cold Spring Harbor Laboratory Press, 1982.

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, or from another antigen or toxin which elicits a response with respect to the pathogen, or from another antigen or toxin which elicits a response with respect to the pathogen, such as, for instance: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nudeoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, HSV, Marek's Disease Virus, or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; an poxvirus antigen, e.g., an ectromelia antigen, a canarypox virus antigen or a fowlpox virus antigen; or an infectious bursal disease virus antigen, e.g., VP2, VP3, VP4.

An epitope of interest can be from an antigen of a human pathogen or toxin, or from another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a C. tetani antigen; a mumps antigen; a pneumococcal antigen, e.g., PspA; a Borrelia antigen, e.g., OspA, OspB, OspC of Borrelia associated with Lyme disease such as *Borrelia burgdorferi, Borrelia afzelli* and *Borrelia garinii*; a chicken pox (varicella zoster) antigen; or a Plasmodium antigen.

Of course, the foregoing lists are intended as exemplary, as the epitope of interest can be derived from any antigen of any veterinary or human pathogen; and, to obtain an epitope of interest, one can express an antigen of any veterinary or human pathogen (such that the invention encompasses the exogenous or foreign nucleic acid molecule(s) of interest encoding at least one antigen).

Since the heterologous DNA can be a growth factor or therapeutic gene, the inventive recombinants can be used in gene therapy. Gene therapy involves transferring genetic information; and, with respect to gene therapy and immunotherapy, reference is made to U.S. Pat. No. 5,252,479, which is incorporated herein by reference, together with the documents cited in it and on its face, and to WO 94/16716 and allowed U.S. application Ser. No. 08/184,009, filed Jan. 19, 1994, each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention further relates to an immunogenic, immunological or vaccine composition containing the inventive vector and an acceptable carrier or diluent(e.g., veterinary acceptable or pharmaceutically acceptable). An immunological composition containing the vector (or an expression product thereof) elicits an immunological response—local or systemic. The response can, but need not be protective. An immunogenic composition containing the inventive recombinants (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method for inducing an immunological response in a host vertebrate comprising administering to the host an immunogenic, immunological or vaccine composition comprising the inventive recombinant virus or vector and an acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

For human administration, the inventive recombinants or vectors, can provide the advantage of expression without productive replication. This thus provides the ability to use recombinants of the invention in immunocompromised individuals; and, provides a level of safety to workers in contact with recombinants of the invention. Therefore, the invention comprehends methods for amplifying or expressing a protein by administering or inoculating a host with a recombinant virus or vector, whereby the host is not a natural host of the recombinant virus or vector, and there is expression without productive replication.

The exogenous or heterologous DNA (or DNA foreign to vaccine virus) can be DNA encoding any of the aforementioned epitopes of interest, as listed above. In this regard, with respect to Borrelia DNA, reference is made to U.S. Pat. No. 5,523,089, WO93/08306, PCT/US92/08697, Molecular Microbiology (1989), 3(4), 479–486, and PCT publications WO 93/04175, and WO 96/06165, incorporated herein by reference.

With respect to pneumococcal epitopes of interest, reference is made to Briles et al. WO 92/14488, incorporated herein by reference, with respect to tumor viruses reference is made to *Molecular Biology of Tumor Viruses, RNA TUMOR VIRUSES* (Second Edition, Edited by Weiss et al., Cold Spring Harbor Laboratory 1982) (e.g., page 44 et seq.—Taxonomy of Retroviruses), incorporated herein by reference.

With respect to DNA encoding epitopes of interest, attention is directed to documents cited herein, see, e.g., documents cited supra and documents cited infra, for instance: U.S. Pat. Nos. 5,174,993 and 5,505,941 (e.g., recombinant avipox virus, vaccinia virus; rabies glycoprotein (G), gene, turkey influenza hemagglutinin gene, gp51,30 envelope gene of bovine leukemia virus, Newcastle Disease Virus (NDV) antigen, FelV envelope gene, RAV-1 env gene, NP (nudeoprotein gene of Chicken/Pennsylvania/1/83 influenza virus), matrix and preplomer gene of infectious bronchitis virus; HSV gD), U.S. Pat. No. 5,338,683 (e.g., recombinant vaccinia virus, avipox virus; DNA encoding Herpesvirus glycoproteins, inter alia), U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, C. tetani, avian influenza, mumps, NDV, inter alia), U.S. Pat. No. 5,503,834 (e.g., recombinant vaccinia, avipox, Morbillivirus, e.g., measles F, hemagglutinin, inter alia), U.S. Pat. No. 4,722,848 (e.g., recombinant vaccinia virus; HSV tk, HSV glycoproteins, e.g., gB, gD, influenza HA, Hepatitis B, e.g., HBsAg, inter alia), U.K. Patent GB 2 269 820 B and U.S. Pat. No. 5,514,375 (recombinant poxvirus; flavivirus structural proteins); WO 92/22641 and U.S. application Ser. Nos. 08/417,210 and 08/372,664 (e.g., recombinant poxvirus; immunodeficiency virus, HTLV, inter alia), WO 93/03145 and allowed U.S. application Ser. Nos. 08/204,729 and 08/303,124 (e.g., recombinant poxvirus; IBDV, inter alia), WO 94/16716 and allowed U.S. application Ser. No. 08/184, 009, filed Jan. 19, 1994 (e.g., recombinant poxvirus; cytokine and/or tumor associated antigens, inter alia), U.S. application Ser. No. 08/469,969 (rabies combination compositions), U.S. application Ser. No. 08/746,668 (lentivirus, retrovirus and/or immunodeficiency virus, including feline immunodeficiency virus, inter alia), U.S. Pat. No. 5,529,780 and allowed U.S. application Ser. No. 08/413,118 (canine herpesvirus), U.S. application Ser. No. 08/471,025 (calicivirus), WO 96/3941 and U.S. application Ser. No. 08/658,665 (cytomegalovirus), and PCT/US94/06652 (Plasmodium antigens such as from each stage of the Plasmodium life cycle).

As to antigens for use in vaccine or immunological compositions, reference is made to the documents and discussion set forth in the documents cited herein (see, e.g., documents cited supra); see also Stedman's Medical Dictionary (24th edition, 1982, e.g., definition of vaccine (for a list of antigens used in vaccine formulations; such antigens or epitopes of interest from those antigens can be used in the invention, as either an expression product of an inventive recombinant virus or vector, or in a multivalent composition containing an inventive recombinant virus or vector or an expression product therefrom).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunologv*, 1988.

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD8+ T cell response (which recognizes virus infected cells or cancerous cells). A minimum peptide length of 13 to 25 amino acids is useful to stimulate a CD4+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, (1992) pp. 79–80.

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, (1992) p. 81

Yet another method for determining an epitope of interest is to perform an X-ray crystallographic analysis of the antigen (full length)-antibody complex. Janis Kuby, *Immunology*, (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

Some guidelines in determining whether a protein is an epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, Specific Binding of Leukemia Oncogene Fusion Protein Peptides to HLA Class I Molecules, Blood 85:2680–2684; Englehard, VH, Structure of peptides associated with class I and class II MHC molecules Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing an tibodies are directed. Disclosures of such epitopes are in many of the references cited in the Relevant Literature section.")

With respect to expression of a biological response modulator, reference is made to Wohlstadter, "Selection Methods," WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al *Physiology of the Bacterial Cell* (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant can regulate use or uptake of the molecule by a cell. Likewise, the recombinant can express a molecule which binds to the enzyme necessary for uptake or use of a molecule, thereby similarly regulating its uptake or use.

Localization targeting of proteins carried out through cleavage of signal peptides another type of modulation or regulation. In this case, a specific endoprotease catalytic activity can be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS USA 85:4686–90 (1988)). The proper cleavage of the poly-proteins is crucial for replication of the virus, and virions carrying inactive mutant HIV protease are non-infectious (Id.). This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, *Proteases and Biological Control*, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$–$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant can express peptide sequences containing additional amino acids at one or both termini.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, *Enzyme Structure and Mechanism*, 2d ed; Freeman & Co. Publishers, 1984)). This type of modulation is possible by the recombinant expressing a suitable suicide substrate, to thereby modulate biological responses (e.g., by limiting enzyme activity).

There are also examples of non-covalent steric hindrance including many repressor molecules. The recombinant can express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function, e.g., phosphorylation, is of importance.

From the foregoing, the skilled artisan can use the present invention to express a biological response modulator, without any undue experimentation.

With respect to expression of fusion proteins by inventive recombinants, reference is made to Sambrook, Fritsch, Maniatis, *Molecular Cloning, A LABORATORY MANUAL* (2d Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants or vectors expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. application Ser. No. 08/184,009, filed Jan. 19, 1994, each of which is also incorporated herein by reference, together with the documents cited therein.

A growth factor can be defined as multifunctional, locally acting intercellular signalling peptides which control both ontogeny and maintenance of tissue and function (see Kendrew, supra, especially at page 455 et seq.).

The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and allowed U.S. application Ser. No. 08/184,009, filed Jan. 19, 1994, provide genes for cytokines and tumor associated antigens and immunotherapy methods, including ex vivo methods, and the skilled artisan is directed to those disclosures.

Thus, one skilled in the art can create recombinants or vectors expressing a growth factor or therapeutic gene and use the recombinants or vectors, from this disclosure and the knowledge in the art, without undue experimentation.

Moreover, from the foregoing and the knowledge in the art, no undue experimentation is required for the skilled artisan to construct an inventive recombinant or vector which expresses an epitope of interest, a biological response modulator, a growth factor, a recognition sequence, a therapeutic gene, or a fusion protein; or for the skilled artisan to use such a recombinant or vector.

As the recombinants or vectors of the invention can be used for expression of gene products in vitro, techniques for protein purification can be employed in the practice of the invention, and such techniques, in general, include:

Briefly, the cells are disrupted and the protein of interest is released into an aqueous "extract". There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration.

Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method for cell disintegration based upon the starting material, and the teachings herein and in the art.

Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed.

Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immuno affinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the proteins or epitopes of interest from expression of a recombinant or vector of the invention, using the standard methodologies outlined hereinabove, and in the literature, as well as the teachings in the Examples below.

As the expression products can provide an antigenic, immunological, or protective (vaccine) response, the invention further relates to products therefrom; namely, antibodies and uses thereof. More in particular, the expression products can elicit antibodies by administration of those products or of recombinants or vectors expressing the products. The antibodies can be monoclonal antibodies; and, the antibodies or expression products can be used in kits, assays, tests, and the like involving binding, so that the invention relates to these uses too. Additionally, since the recombinants or vectors of the invention can be used to replicate DNA, the invention relates to the inventive recombinants as vectors and methods for replicating DNA by infecting or transfecting cells with the recombinant and harvesting DNA therefrom. The resultant DNA can be used as probes or primers or for amplification.

The administration procedure for the inventive recombinants or vectors or expression products thereof, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions can be prepared in accordance with standard techniques well known to those skilled in the pharmaceutical, medical or veterinary arts. Such compositions can be administered in dosages and by techniques well known to those skilled in the medical or veterinary arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from expression by an inventive recombinant or vector or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant or vector may be in admixture with a suitable carrier, diluent, or excipient such as sterile water, physiological saline, glucose or the like.

Antigenic, immunological or vaccine compositions typically can contain an adjuvant and an amount of the recombinant or vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if the recombinant is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 μg. The inventive recombinant or vector can be administered in any suitable amount to achieve expression at these dosage levels. The viral recombinants of the invention can be administered in an amount of about $10^{3.5}$ pfu; thus, the inventive viral recombinant is preferably administered in at least this amount; more preferably about $10^4$ pfu to about $10^6$ pfu; however higher dosages such as about $10^4$ pfu to about $10^{10}$ pfu, e.g., about $10^5$ pfu to about $10^9$ pfu, for instance about $10^6$ pfu to about $10^8$ pfu can be employed. Suitable quantities of inventive plasmid or naked DNA in plasmid or naked DNA compositions can be 1 ug to 100 mg, preferably 0.1 to 10 mg, but lower levels such as 0.1 to 2 mg or preferably 1–10 ug may be employed Other suitable carriers or diluents can be water or a buffered saline, with or without a preservative. The expression product or recombinant or vector may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology*, 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Furthermore, the inventive vectors or recombinants can be used in any desired immunization or administration regimen; e.g., as part of periodic vaccinations such as annual vaccinations as in the veterinary arts or as in periodic vaccinations as in the human medical arts, or as in a prime-boost regimen wherein an inventive vector or recombinant is administered either before or after the administration of the same or of a different epitope of interest or recombinant or vector expressing such a same or different epitope of interest (including an inventive recombinant or vector expressing such a same or different epitope of interest), see, e.g., documents cited herein such as U.S. application Ser. No. 08/746,668.

Additionally, the inventive vectors or recombinants and the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen (s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinants or vectors or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinants or vectors of the invention are also useful for generating DNA for probes or for PCR primers which can be used to detect the presence or absence of hybridizable DNA or to amplify DNA, e.g., to detect a pathogen in a sample or for amplifying DNA.

Since viruses require translation of viral mRNAs in order to generate viral proteins required for replication, it is evident that any function which blocks the action of PKR in the infected cell will have a positive effect on viral protein expression. Thus, co-expression, in some fashion, of the vaccinia E3L/K3L gene products, or a homolog of E3L and/or K3L, may provide a general mechanism for enhancing the expression levels of heterologous gene products by vectors in general. The E3L/K3L or homologous functions may enhance or augment native anti-PKR mechanisms, and thus increase protein expression levels and/or persistence. This provides a useful element towards optimizing the efficiency of eukaryotic virus systems as immunization vehicles. This approach could be further extended for improvement of DNA-based immunogens, e.g., naked DNA or plasmid DNA vector systems. Further, employing a nucleotide sequence for a transcription factor, e.g., for an early and/or late viral transcription factor, in conjunction with enhancing translation by employing a nucleotide sequence for a translation factor, can even further enhance or increase expression by increasing or enhancing transcription and translation; and thus, increasing or enhancing levels or persistence of expression can be obtained.

A better understanding of the present invention and of its many advantages will be had from the following non-limiting Examples, given by way of illustration.

EXAMPLES

Example 1—NYVAC Recombinants Containing H4L

The plasmids placZH6H4L and placZH6H4Lreverse (ATCC Deposit No. ATC-97913) were used as donor plasmids for in vivo recombination with the rescue virus vP994 (ATCC Deposit No. VR-2558; U.S. Pat. No. 5,494,807, incorporated herein by reference; vaccinia H6 promoter/HIV1 MN env-noncleavable, secreted gp140, in HA insertion site). The donor plasmids were designed to replace the endogenous promoter and coding sequences of H4L by homologous recombination. The resulting recombinant viruses were designated vP1379 and vP1380; vP1379 contains the H6lacZ/H6H4L cassette in a head-to-head configuration; vP1380 contains the H6lacZ/H6H4L cassette in a head-to-tail configuration (SEQ ID NO: 1; FIG. 1).

The plasmids were constructed as follows:

H4L Expression Cassette

The H4L open reading frame (orf) as delineated in Goebel et al. 1990 corresponds to positions 94830–92446 in the Copenhagen (vaccine) strain vaccinia virus genomic sequence. pSD404VC contains a clone of the 8.6 Kb HindIII H fragment of Copenhagen vaccinia virus inserted into the pUC vector background. pSD404VC was digested with PvuII to isolate a 3860 bp fragment containing the H4L coding sequences and flanking sequences. The 3860 bp fragment was inserted into the blunted BamHI site of pBSecogpt (*E.coli* gpt gene (ATCC No. 37145) under the control of Copenhagen B13R promoter in the pBS SK vector (Stratagene La Jolla, Calif.)) resulting in plasmid pRW935.

pRW935 was linearized with EcoRI and partially digested with DraI to remove a 970 bp fragment containing the 5' end of the H4L coding sequence. Using a series of Polymerase Chain Reactions (PCRs) the H4L coding sequence was reengineered to be under the control of the modified vaccinia H6 promoter (Perkus et al. 1989). Using the plasmid template pRW935 and primer pairs RW500/RW502 and RW501/RW503 in the PCR amplifications, the 5' H4L sequences were regenerated. In addition, the oligonucleotide, RW502, modifies the H4L coding sequences (position 341–348 from the A of the ATG) from TTTTTTTT to TTTTCTTC without altering the predicted amino acid sequence to remove an early transcriptional stop signal (Yuan, L. and Moss, B., 1987). The modified H6 promoter was amplified from the plasmid template pRW936 using oligonucleotides RW504 and RW507. Oligonucleotides RW505 and RW506 having complementary sequences were PCR amplified directly. The four PCR reactions were pooled and further amplified using primer pair RW500 and RW505. The resulting PCR fragment was digested with DraI and EcoRI and cloned into DraI and EcoRI digested pRW935 generating pRW939. A PCR introduced error in the 5' end of the coding region of pRW939 was corrected, resulting in plasmid pRW947. Specifically, the PCR error introduced in pRW939 (H4L codon 155 is AAA—correct codon should be GAA) was corrected by replacement of the 600 bp pRW939 AflIII-EcoRI fragment with the equivalent fragment from pRW935 to generate pRW939. The oligonucleotide sequences for each of the above-identified oligonucleotides (RW500 and RW501 to RW507; SEQ ID NOS: 9 to 16) are:

RW500 5'- GAAATAGTTAGCGTCAAC -3'

RW501 5'- TGTCTAATGTGTTGAAGAAAAGATCATACAAGTTATAC -3'

RW502 5'- AACTTGTATGATCTTTTCTTCAACACATTAGACATGTATTTAC -3'

RW503 5'- TAAGTTTGTATCGTAATGGACTCTAAAGAGACTATTC -3'

RW504 5'- AGTCTCTTTAGAGTCCATTACGATACAAACTTAAC -3'

RW505 5'-CCGACGATTTTAAAACGCCACCGTCAGGGAAAGTTTCATAAGAAGCACCGGAAGAGAAGAGAATTCTCGGGACAATTGGATC -3'

RW506 5'-GTCTAGCTGGTGCTGAGTTTCTACGTGAGTTGATTCGTCTCTTGCGTGCCTCTCGTGATCCAATTGTCCCGAGATATTCTC -3'

RW507 5'-GTAGAAACTCAGCACCAGCTAGACAAGCTTCTTTATTCTATACTTAAAAAGTGAAAATAAATAC-3'

The plasmid pRW947 was digested with XhoI to generate two fragments. The 7036 bp fragment containing the H6 promoted H4L in the pBSSK vector background was purified and self-ligated, resulting in the plasmid pH6H4L. The plasmid pRW973A, containing a LacZ expression cassette under the control of the vaccinia H6 promoter, was digested with HindIII. The 3.3 Kbp fragment was purified and ligated into the HindIII digested pH6H4L, thereby generating pLACZH6H4Lreverse (H6 promoted LacZ gene and H6 promoted H4L gene in head-to-tail configuration), and placZH6H4L (H6 promoted lacZ gene and H6 promoted H4L gene in a head-to-head configuration).

Example 2—ALVAC Recombinants pMPC6H6K3E3 (ATCC No. 97912) was used as a donor plasmid in in vivo recombination (Piccini et al., 1987) with rescuing virus vCP205 (ATCC No. VR-2557; U.S. application Ser. No. 08/417,210, incorporated herein by reference; HIV expression cassette—vaccinia H6 promoter/HIV truncated env MN strain, I3L gag with protease in ALVAC C3 insertion site); and the resulting recombinant virus was designated vCP1431A (vaccinia H6/K3L and E3L cassette in the C6 locus).

pC8H6H4 was used as the donor plasmid in in vivo recombination with vCP205 and the resulting recombinant virus designated vCP1435 (HIV cassette at C3 locus and the vaccinia H6/H4L expression cassette at C8 locus; H6/H4L expression cassette flanked by ALVAC C8 insertion site sequences (SEQ ID NO: 2) shown in FIG. 2).

vCP1431A was also used as a rescuing virus in in vivo recombination using plasmid pC8H6H4, generating the recombinant designated vCP1437A (HIV cassette at the C3 locus, the H6/K3L and E3L cassette at the C6 locus, and the vaccinia H6/H4L cassette at the C8 locus). With respect to the H6/K3L expression cassette and the vaccinia E3L gene with the endogenous promoter flanked by the ALVAC C6 insertion site sequences reference is made to FIG. 3 (SEQ ID NO: 3).

pC3H6FHVB (ATCC No. ATCC-97914; FIG. 5, SEQ ID NO: 5; H6 promoted FHV gB ORF with early transcriptional and translational stop signals at both 5' and 3' ends flanked by the left and right arms of the ALVAC C3 locus) was used in in vivo recombination with the ALVAC (ATCC No. VR-2547) to generate vCP1459 (H6 promoted FHV gB expression cassette in deorfed C3 insertion locus). With respect to the FHV-1 gB coding region in which the two internal $T_5NT$ motifs have been mutated, see FIG. 4 (SEQ ID NO: 4).

pC3H6FHVB was used in in vivo recombination with vCP1431A to generate vCP1460 (H6 promoted FHV gB expression cassette in the deorfed C3 insertion locus and vaccinia E3L/K3L genes in C6 locus).

pC3H6FHVB was used in in vivo recombination with vCP1437 to generate vCP1464 (H6 promoted FHV gB expression cassette in deorfed C3 insertion locus, vaccinia E3L/K3L genes in C6 locus and H6 promoted vaccinia H4L ORF in C8 locus).

pMPC5H6PN (HIV pol/nef "string of beads" cassette in the ALVAC C5 locus) was used in recombination with vCP205 to obtain vCP1433 (ATCC Deposit No. VR-2556). Thus, recombinant ALVAC-MN120TMGNPst (vCP1433) was generated by insertion of an expression cassette encoding a synthetic polypeptide containing all of the known Pol CTL epitopes (Nixon and McMichael; 1991) and all of the known human Nef CTL epitopes into vCP205 at the insertion site known as C5.

pMPC6H6K3E3 (ATCC Deposit No. ATCC-97912; containing vaccinia H6/K3L expression cassette and vaccinia E3L gene with endogenous promoter flanked by the ALVAC C6 insertion site sequences) was used in recombination with vCP1433 to obtain vCP1452. FIGS. 6 and 7 show the nucleotide and amino acid sequences of the vCP1433 and vCP1452 inserts. FIG. 8 shows the K3L E3L in C6 in vCP1452. vCP1452 contains the HIV type 1 gag and protease genes derived from the IIIB isolate, the gp120 envelope sequences derived from the MN isolate, and sequences encoding a polypeptide encompassing the known human CTL epitopes from HIV-1 Nef and Pol (Nef1 and Nef2 CTL epitopes, and Pol1, Pol2 and Pol3 CTL epitopes). The expressed gp120 moiety is linked to the transmembrane (TM) anchor sequence (28 amino acids) of the envelope glycoprotein. In addition to the HIV coding sequences vCP1452 contains the vaccinia virus E3L and K3L coding sequences inserted into the C6 site. The insertion sites and promoter linkages for this construct are shown in the Table below.

| Insert | Insertion Site | Promoter |
|---|---|---|
| HIV1 MN gp120 + TM | C3 | H6 |
| HIV1 IIIB gag (+pro) | C3 | I3L |
| Pol3/Nef C term/Pol2/Nef central/Pol1 | C5 | H6 |
| Vaccinia virus E3L | C6 | endogenous |
| Vaccinia virus K3L | C6 | H6 |

vCP300 is an ALVAC recombinant containing HIV gp120TM (MN), gag/pro (IIIB) (C3 locus), Nef (C6 locus), and Pol (C5 locus), as described in U.S. application Ser. No. 08/417,210, incorporated herein by reference.

Plasmids for preparing these recombinants were prepared as follows:

Vaccinia H4L Expression Cassette Into ALVAC pCPM6LDEL was generated by using primer pair H4A and H4B to amplify a 900 bp fragment from pBAMM11.6 (ALVAC 11.6 kb BamHI M fragment in pBSSK bector background), and primer pair H4C and H4D (SEQ ID NOS: 17 and 18) to amplify a 940 bp fragment from pBAMM11.6 (H4C 5'ACTACTAATTAGCTATAAAAACCCGGGATTAG-TTTTTATTACTAACTAATTACTATACTG3') (H4D 5'ATCATCGGATCCTTTAATAATCTTATGAACTTTT-ATAAATATGAG3'). A fusion PCR reaction using the PCR products from the amplifications and primer pair H4A and H4D obrained an 1840 bp PCR fusion fragment which was then cloned into the T/A Cloning vector for sequence confirmation. The sequence was found to have a PCR deletion at position 8054. The 1840 bp fragment was removed from the T/A vector by digestion with BamHI. The fragment was then cloned into the BamHI digested pBSSK ΔEcoRI-SmaI vector. The deletion was repaired by digesting the construct with HindIII to remove a 250 bp fragment of the right arm and religating to obtain pCPM6LDEL.

placZH6H4Lreverse was digested with PspAI and Asp700 resulting in a 1920 bp fragment containing the H6 promoter and the 5' 1780 bp of the H4L gene. The remaining 590 bp of the H4L gene were generated using PCR amplification from the plasmid template placZH6H4Lreverse using primer pair H4A and H4B. The oligonucleotide sequences for primer pair H4A and H4B (SEQ ID NOS: 19 and 20) are:

Oligonucleotide Sequences

H4A 5'- ATCATCGAAGAGCTTCCGCTATCTGCATT-AAAGTTT-3'

H4B 5'- ATCATCCCCGGGAAGCTTTTAGTTATTG-AAATTAATCATATA-3'

The 590 bp PCR fragment was gel purified and cloned into the TA Cloning vector (Invitrogen San Diego, Calif. 92121) for sequence confirmation. The 590 bp insert containing the 3' H4L sequences was excised from the TA vector by digestion with PspAI and Asp700. The 1920 bp and the 590 bp fragments were directionally cloned into the PspAI digested pCPM6LDEL plasmid vector (containing the deorfed ALVAC M6L insertion site) to generate the plasmid pM6LDELH6H4 containing the H6/H4L expression cassette flanked by ALVAC sequences at the M6L insertion site.

ALVAC pC8 insertion vector was generated as follows: PCR J36, containing the C8 ORF and flanking sequences, was generated using JP121 (CAT-CAT-GAG-CTC-ACT-TAT-TAC-ATC-CTA-CT) and JP122 (TAC-TAC-GGT-ACC-TTT-AAT-AAG-CAA-TCA-CT) (SEQ ID NOS: 21 and 22) on ALVAC DNA. The resulting approximately 1.7 kb band was digested with Asp718/SacI and ligated into Asp718/SacI digested pBSSK+. After confirmation by sequence analysis, the resulting plasmid was designated pCPF85S3L. To remove most of the C8 ORF and introduce transcriptional and translational stops along with a MCS into pCPF85S3L, the plasmid was digested with SnaBI/HindIII and ligated to ~115 bp PCR J618I SnaBI/HindIII fragment, yielding pC8. PCR J618I is a fusion PCR product of PCRs J616 and J617 using primers JP516 (TAG-GAA-GAT-ACG-TAT-TAT-TTT-ATA-C) and JP519 (ATC-CCA-TTA-TGA-AAG-CTT-ATA-G) (SEQ ID NOS: 39 and 40). PCR J616 was generated using primers JP516 and JP517 (CTC-GAG-CTG-CAG-GAT-ATC-ATC-GAT-GGA-TCC-TTT-TTA-TAG-CTA-ATT-AGT-CAC-GTA-CCT-TTA-TCA-TTA-GTA-ACA-AAT) (SEQ ID NO: 41) on plasmid pCPF85S3L. PCR J617 was generated using primers JP518 (GGA-TCC-ATC-GAT-GAT-ATC-CTG-CAG-CTC-GAG-TTT-TTA-TGA-CTA-GTT-AAT-CAC-GGC-CGC-TCA-ATA-TTG-TAT-TGG-ATG-GTT-AG) (SEQ ID NO: 42) and JP519 on plasmid pCPF85S3L. Plasmid pC8, the C8 insertion plasmid, was confirmed by sequence analysis and contains a ~440 bp left arm, a ~1162 bp right arm, a MCS with unique BamHI, ClaI, EcoRV, PstI, and XhoI sites, flanked by both transcriptional and translational stop sequences.

From the plasmid pM6LDELH6H4, the 2.5 Kbp H6/H4 expression cassette was excised with SmaI, and the resulting 2.5 Kbp SmaI fragment was purified and inserted into the ALVAC pC8 insertion vector at the EcoRV site generating pC8H6H4.

K3L Expression Cassette

The K3L coding sequences were synthesized by PCR amplification using pSD407VC containing Copenhagen vaccinia HindIII K fragment as template, as described in U.S. Pat. No. 5,378,457. The oligonucleotides MPSYN 763 and MPSYN 764 (SEQ ID NOS: 23 and 24) were used as primers for the PCR reaction.

MPSYN 763

5'- CCCTCTAGATCGCGATATCCGTTAAGTTTGTAT-CGTAATGCTTGCATTTTGTTATTCGT-3'

MPSYN 764 5'-CCCGAATTCATAAAAATTATTGATG-TCTACA-3'

The approximately 325 bp PCR fragment was digested with XbaI and EcoRI yielding a 315 bp fragment. This 315 bp fragment was purified by isolation from an agarose gel and ligated with XbaI and EcoRI digested PBSSK+ vector (from Stratagene LA Jolla, Calif.). The nucleic acid sequence was confirmed directly from alkali denatured plasmid template as described in Hattori, M. and Sakaki, Y., 1986, using the modified T7 polymerase (Tabor, S. and Richardson, C.C. 1987) and Sequenase (from U.S. Biochemicals Cleveland, Ohio). This plasmid was designated pBS 763/764. Digesting pBS 763/764 with NruI and XhoI, a 340 bp fragment was isolated for cloning into the plasmid vector pMM154 containing a cassette with the vaccinia H6 promoter controlling an irrelevant gene in the NYVAC $tk^-$ insertion vector background, which was prepared by digestion with NruI (partially) and XhoI, such that the 340 bp fragment from pBS 763/764 containing the K3L gene could be directionally oriented next to the H6 promoter generating pMPTKH6K3L. The plasmid pMP42GPT containing the dominant selectable marker Eco gpt gene (Pratt D. and Subramani S. 1983) under the control of the Entomopox 42k promoter, was digested with SmaI and BamHI to yield a 0.7 Kbp 42k-Eco gpt expression cassette. This 0.7 Kbp fragment was purified and ligated into SmaI and DanHI cut pMPTKH6K3L generating the plasmid pMPTKH6K3Lgpt.

This plasmid was digested with XhoI, generating a 1.2 Kbp fragment containing the H6/K3L and the 42k/Ecogpt expression cassette, which was then gel purified. The 1.2 Kbp XhoI fragment was inserted into the XhoI site of the ALVAC C6 insertion plasmid pC6L (described in U.S. Pat. No. 5,494, 807), generating pMPC6H6K3Lgpt.

E3L/K3L ALVAC Expression Cassette

The entire E3L gene is contained within a 2.3 Kbp EcoRI fragment isolated from pSD401VC, which contained a clone of the HindIII E fragment from Copenhagen vaccinia. The 2.3 Kbp EcoRI fragment was inserted into pMPC6H6K3Lgpt that had been partially digested with EcoRI, generating the plasmid pMPC6H6K3E3gpt. The plasmid pMPC6H6K3E3gpt was digested with XhoI and the resulting 6.8 Kbp vector fragment was purified and self-ligated, resulting in the plasmid pMPC6E3. The plasmid pMPTKH6K3L was digested with PspAI and the resulting 560 bp fragment containing the H6/K3L expression cassette was ligated into PspAI digested pMPC6E3 resulting in the plasmid construct pMPC6H6K3E3.

Construction of the H6-promoted FHV gB donor plasmid

The entire coding region of the Feline Herpesvirus 1 glycoprotein gB (FHV-1 gB) was obtained by digestion of pJCA079 (FHV gB coding region in which 5' and 3' $T_5NT$ sequences were mutated to change the early transcriptional stop signal without affecting amino acid sequences; the I3L vaccinia promoter has been coupled to the 5' end of the gB ORF; see FIG. 4, SEQ ID NO: 4) with PstI and isolating a 3 Kbp fragment from an agarose gel. The purified PstI fragment was cloned into an ALVAC C3 insertion plasmid (pVQH6CP3LSA) also digested with PstI (the unique BamHI site in pVQH6CP3LSA was previously inactivated by digestion with BamHI, blunting the ends with Klenow polymerase and religation; pVQH6CP3LSA was obtained by digesting pVQH6CP3L, discussed in U.S. Pat. No. 5,494, 807, with NotI and NsiI, from which a 6623 bp fragment was isolated and ligated to annealed oligonucleotides CP34 (5'GGCCGCGTCGACATGCA3') and CP35 (5'TGTCGACGC3') (SEQ ID NOS: 25 and 26). The resulting plasmid, pRAC5, was screened for proper orientation of the gB coding region with respect to the H6 promoter. To properly link the H6 promoter to the FHV gB initiation codon, an 800 bp PCR fragment was amplified from pJCA079 using oligonucleotides RG789 (SEQ ID NO: 27)(5'-TTTCATTATCGCGATATCCGTTAA-GTTTGTATCGTAATGTCCACTCGTGGCGATC-3') and RG787 (SEQ ID NO: 28)(5'-GGAGGGTTT-CAGAGGCAG-3'). This purified fragment was digested with NruI/BamHI and ligated into pRAC5 also digested with NruI/BamHI. The resulting plasmid was the FHV gB donor plasmid, pC3H6FHVB.

"String of Beads" Cassette

The "string of beads" expression cassette for the nef and pol CTL epitopes (H6/Pol 3/Nef C term/Pol 2/Nef central/Pol 1) was generated by PCR (polymerase chain reaction) as detailed below, using template pHXBD2 for pol epitopes and template 2-60-HIV.3 for Nef epitopes. Initial assembly was in two parts: (1) H6(partial promoter)/Pol 3/Nef C term(Nef 2); (2) Pol 2/Nef central (Nef 1)/Pol 1 in pBSSK. These were combined, then moved to pBSH6-11 for the assembly of the entire H6 promoter, then the H6/HIV cassette was moved to a CS insertion plasmid.

(1) H6/Pol 3/Nef C term(Nef 2)

A 230 bp fragment (A) was derived by PCR to obtain the H6 linkage and Pol3 using synthetic oligonucleotides MPSYN783 and MPSYN784 (SEQ ID NOS: 29 and 30) and template pHXBD2. pHXBD2 was derived at the NIH/NCI (Dr. Nancy Miller) from a recombinant phage library of XbaI digested DNA from HTLV-III infected H9 cells cloned in lambda-J1 (Shaw et al., 1994). This plasmid contains the entire proviral DNA sequence of the HIV IIIB isolate.

A 110 bp fragment (B) was derived by PCR to obtain Nef2 using oligonucleotides MPSYN785/MPSYN786 (SEQ ID NOS: 31 and 32) and template p2-60-HIV.3 (described in U.S. application Ser. No. 417,210).

PCR fragments A and B were combined in a PCR as template to obtain a 300 bp fragment containing H6 linkage/Pol3/Nef2 using external primers MPSYN783/MPSYN786 (SEQ ID NOS: 29 and 32). The 300 bp fragment was digested with XhoI/HindIII and a 290 bp fragment was isolated and ligated with similarly digested pBSSK to generate pBS783/786. The sequence was confirmed.

(2)Pol 2/Nef central (Nef 1)/Pol 1

A 210 bp fragment (C) containing Pol2 was derived by PCR using synthetic oligonucleotides MPSYN787/MPSYN788 (SEQ ID NOS: 33 and 34) and template pHXBD2.

A 270 bp fragment (D) containing Nef1 was derived by PCR using synthetic oligonucleotides MPSYN789/MPSYN790 (SEQ ID NOS: 35 and 36) and template p2-60-HIV.3 (described in U.S. application Ser. No. 08/417,210).

A 170 bp fragment (E) containing Pol1 was derived by PCR using primers MPSYN791/MPSYN792 (SEQ ID NOS: 37 and 38) and template pHXBD2.

Fragments C and D were combined as template in a PCR for Pol 2/Nef 1 using external primers MPSYN787/MPSYN790 (SEQ ID NOS: 33 and 36) resulting in a 460 bp PCR product (C+D).

Fragments D and E were combined as template in a PCR for Nef 1/Pol 1 using external primers MPSYN789/MPSYN792 (SEQ ID NOS: 35 and 38), resulting in isolation of a 420 bp fragment (D+E).

Fragments (C+D) and (D+E) were combined as template in a PCR with external primers MPSYN787/MPSYN792 (SEQ ID NOS: 33 and 38) to obtain a 610 bp fragment containing Pol 2/Nef 1/Pol 1. This 610 bp fragment was digested with HindIII/PstI. The resulting 590 bp fragment was ligated with pBSSK cut with HindIII/PstI to generate pBS787/792. The sequence was confirmed.

```
MPSYN783: 5' CCC CTC GAG TCG CGA TAT CCG TTA AGT TTG TAT CGT AAT (58 mer)(SEQ ID NOS:29 to 38)
          GCC ACT AAC AGA AGA AGC A 3'

MPSYN784: 5' AAA TCT CCA CTC CAT CCT TGT TTT CAG ATT TTT AAA 3'  (36 mer)

MPSYN785: 5' AAT CTG AAA ACA GGA ATG GAG TGG AGA TTT GAT TCT 3'  (36 mer)

MPSYN786: 5' CCC AAG CTT ACA ATT TTT AAA ATA TTC AGG 3'          (30 mer)

MPSYN787: 5' CCC AAG CTT ATG GCA ATA TTC CAA AGT AGC 3'          (30 mer)

MPSYN788: 5' TGG AAA ACC TAC CAT GGT TGT AAG TCC CCA CCT CAA 3'  (36 mer)
```

-continued

```
MPSYN789: 5' TGG GGA CTT ACA ACC ATG GTA GGT TTT CCA GTA ACA 3'  (36 mer)

MPSYN790: 5' TAC AGT CTC AAT CAT TGG TAC TAG CTT GTA GCA CCA 3'  (36 mer)

MPSYN791: 5' TAC AAG CTA GTA CCA ATG ATT GAG ACT GTA CCA GTA 3'  (36 mer)

MPSYN792: 5' CCC CCT GCA GAA AAA TTA AGG CCC AAT TTT TGA AAT 3'  (36 mer)
```

Assembly of entire cassette:

A 590 bp HindIII/PstI fragment was isolated from pBS787/792 and ligated with vector pBS783/786 cut with HindIII/PstI to generate pBS783/792. pBS783/792 was cut with EcoRV and PstI, to generate an 880 bp fragment which was then ligated with similarly digested vector pBSH6-1 to generate pBSH6PN. Plasmid pBSH6PN was digested with BamHI and a 1060 bp fragment was isolated. pVQC5LSP1, a generic C5 donor plasmid, was digested with BamHI and ligated with the 1060 bp fragment from pBSH6PN. The resulting plasmid, pMPC5H6PN, contains the HIV pol/nef "string of beads" cassette in the ALVAC C5 locus.

Example 3—Expression studies

Example 3.1—NYVAC Expression Results

Dishes containing confluent monolayers of cells were infected at a multiplicity of infection (moi) of 2. After incubation for specified time periods, cells were incubated in labeling medium for 1 hour. At the end of the incubation, cells were harvested for immunoprecipitation analysis as described (Harlow, E and Lane, D (1988); Langone, J. (1982)).

Cells were infected at an moi of 2 pfu/cell and incubated for specified time periods. At the appropriate time post-infection, cell lysates were prepared for RNA analysis. The medium was aspirated and cells were harvested. RNA was isolated and prepared using the TRI-Reagent (Molecular Research Center Inc. Cincinnati, Ohio 45212) as per manufacture instructions and analyzed by slot blot. Radiolabelled DNA probes were used to detect specific RNA species.

The effect of vP1379 and vP1380 compared to the parental virus vP994 on the expression of HIV env truncated MN strain was studied by radiolabeling at specific times post-infection on CEF cells. IP analysis with monoclonal antibody against HIV env truncated MN strain (mAb K3A) revealed a significant increase in de novo synthesis for vP1380 infected cells at early times post infection compared to either vP994 parental virus or vP1379. A similar trend is observed at late times post infection. IP analysis with rabbit anti H4L antiserum (provided by Dr. S. Shuman, Sloan-Kettering Institute, N.Y.) show that only vP1380 infected cells expressed H4L product early in infection. Neither vP994 nor vP1379 infected cells expressed H4L early in infection. All samples show de novo synthesis of H4L late in infection, but expression rates are higher for vP1380 infected cells than for either vP994 or vP1379 infected cells. IP analysis of E3L product, a constitutive vaccinia protein, show that de novo synthesis occurs at a higher rate at all times post infection in vP1380 infected cells than in either vP994 or vP1379 infected cells.

These results indicate that vP1379 is a defective recombinant with a pattern of expression identical to the parental virus unlike vP1380 recombinant which expresses H4L at early and late times post-infection. This early H4 expression clearly correlates with the enhanced expression of the proteins under study (HIV env and E3L) at early times post-infection.

The following studies were conducted with vP1380 and vP994 since vP1379 does not express H4L product at early times post-infection. The rate of expression at different times post infection in HeLa cells (non permissive system) was studied by IP analysis. IP analysis with anti-H4L shows that vP1380 infected cells expressed H4L product at all times post-infection (3, 6, 24 and 48 Hrs.). No product was detected in vP994 infected cells at any time post infection. Sustained de novo synthesis is observed that increases with time. Analysis of HIV Env product shows that, although product expression levels are higher at all times for vP1380 infected cells vs. vP994's, the most significant difference is seen at late times, 24 and 48 Hrs., suggesting that expression of H4L must have an impact at some level on expression of HIV Env product. Expression of E3L product is also increased in vP1380 infected cells compared to vP994.

Experiments performed on L929 cells gave similar results. The most significant difference was that expression rates of the H4L product at all times post infection was very low, however there was a dramatic difference in the de novo synthesis rate of HIV Env component. Differences in the rates of Env synthesis peaked at 24 hours with a 5 to 10 fold increase in vP1380 infected cells compared to vP994.

Since H4L product is an early transcription factor, it is of interest to determine if the results obtained at the expression level correlate with an increase in H4L message in vP1380 infected cells. RNA analysis by slot blots indicate that H4L message is detectable at all times post infection in vP1380 infected cells and achieved a steady state at 6 Hrs. post infection.

HIV Env message levels increase rapidly to steady state levels at 3 Hrs post infection and remained at those levels for all time points in vP1380 infected cells. On the other hand, vP994 infected cells show a peak of HIV env message at 6 hours post infection and a decline starting at 12 hours. E3L message in vP1380 infected cells is present at higher levels for all times post infection compared to vP994 infected cells. This pattern of RNA levels is consistent with the pattern of de novo synthesis rate at the protein level.

Mice were immunized by the intraperitoneal route on day 0 and 28. Starting prior to the first immunization and at two week intervals following the immunization, mice were bled from the retroorbital plexus. Sera were prepared from the collected blood by standard clotting techniques and stored frozen at −20° C. until use in kinetics ELISA for antibodies reactive to the HIV envelope glycoprotein.

High doses of vP994 or vP1380 elicited similar levels of antibodies (Table below). However, at the lowest dose, $5\times10^6$ pfu, only vP1380 was capable of generating HIV antibodies. Moreover, the level of antibodies induced by the low dose was comparable to the levels of antibodies elicited by the highest dose, $5\times10^7$ pfu.

At a dose too low for vP994, lacking vaccinia H4 but identical in all other respects to vP1380, to elicit an antibody response, vP1380 induced antibody responses equivalent to those elicited by the highest doses tested. Thus, the overexpression of vaccinia H4L in NYVAC may result in increased potency for inducing humoral responses.

TABLE

Antibody responses to recombinant HIV-1 MN/BRU gp160.

| VIRUS | DOSE | MOUSE | KINETICS (mOD/min) WEEKS 0 | 2 | 4 | 6 | 8 | 10 | 12 | 14 |
|---|---|---|---|---|---|---|---|---|---|---|
| NYVAC | HI | a | 0 | 1 | 0 | 1 | 2 | 2 | 1 | 2 |
| | | b | 0 | 0 | 0 | 2 | 2 | 2 | 2 | 2 |
| | | c | 0 | 0 | 0 | 2 | 1 | 1 | 1 | 1 |
| vP994 | HI | a | 0 | 6 | 8 | 42 | 45 | 44 | 44 | 45 |
| | | b | 0 | 1 | 1 | 34 | 42 | 35 | 24 | 23 |
| | | c | 3 | 1 | 3 | 34 | 40 | 31 | 33 | 34 |
| vP994 | LO | a | 0 | 1 | 2 | 4 | 3 | 3 | 5 | 6 |
| | | b | 1 | 1 | 0 | 2 | 2 | 3 | 3 | 3 |
| | | c | 1 | 0 | 1 | 14 | 16 | 17 | 12 | 13 |
| vP1380 | HI | a | 2 | 8 | 39 | 41 | 49 | 47 | 52 | 50 |
| | | b | 3 | 12 | 45 | 49 | 46 | 51 | 54 | 49 |
| | | c | 1 | 7 | 35 | 42 | 41 | 43 | 40 | 39 |
| vP1380 | LO | a | 1 | 2 | 3 | 49 | 45 | 47 | 46 | 44 |
| | | b | 0 | 1 | 2 | 30 | 30 | 34 | 36 | 40 |
| | | c | 0 | 3 | 14 | 54 | 48 | 51 | 51 | 54 |

Mice were inoculated during weeks 0 and 4.
vP994, HIV 1 MN gp140, noncleavable, secreted envelope glycoprotein.
vP1380, HIV 1 MN gp140 + vaccinia H4L transcription factor.
vCP125, HIV 1 MN gp160.
HI dose, $5 \times 10^7$ pfu.
LO dose, $5 \times 10^6$ pfu.

As discussed above, possibly, part of the enhanced levels in vP1380 are due to enhanced transcription and expression of viral specific products such as E3L, such that there is enhanced transcription and translation involved in expression in vP1380. There was more expression of the exogenous DNA and at more persistent levels in vP1380, in accordance with the invention wherein vectors obtain greater levels of expression and more persistent levels of expression. Enhanced expression profiles in the murine system provided enhanced immunogenicity in mice, as shown by vP1380 being more immunogenic in mice than vP994. Another observation is that enhancement profiles are seen in restrictive early cells in the abortive early ALVAC recombinants herein, whereas the profiles were not observed in cells where there was productive replication, e.g., VERO or CEF, suggesting that the factor and the foreign DNA preferably should be expressed substantially co-temporally or contemporaneously, i.e., that preferably there should be co-expression at substantially the same time or stage, and that the time of expression, e.g., early, late, early and late, should be matched with the phenotype of the vector (e.g., abortive early, abortive late), i.e., that in a system in which viral replication is not impaired (a permissive system) or in a system in which replication is aborted at a time when expression is not matched with the phenotype of the vector may not obtain optimal expression. Thus, in an abortive early system such as ALVAC or NYVAC, one preferably expresses exogenous DNA and a transcriptional or transcriptional and translational factor early; in an abortive late system, one preferably expresses exogenous DNA and a transcriptional or transcriptional and translational factor late or early and late (as expression only early may be akin to expression in a permissive system, i.e., one may not necessarily obtain optimal expression).

Example 3.2—ALVAC Expression Results

ALVAC-HIV Recombinants

Immunoprecipitation (IP) was used to provide a semi-quantitative comparison of the temporal expression of the HIV-I cassette contained in the ALVAC recombinants in MRC-5 infected cells. Heat inactivated sera from HIV patients was obtained and used for the IP as described in the methods. The antiserum will precipitate the 120 KDa env protein and the various cleavage products from the gag protein precursor. In the analysis of the IP data it is apparent that the ALVAC recombinants vCP1431A and vCP1437A containing the E3L/K3L cassette had a significant increase in the level of expression at all times post infection when compared to the ALVAC recombinant vCP205 without the E3L/K3L cassette.

Interestingly vCP1431A and vCP1437A had similar expression profiles; insertion of H6/H4L into an ALVAC E3L/K3L background did not enhance expression above E3L/K3L, suggesting that vaccinia H4L is not necessarily functional in ALVAC; but, manipulation of ALVAC transcriptional factors would lead to enhanced expression. Although there are homologs of vaccinia transcriptional factors in canarypox, the requirements in canarypox may be biochemically different; but, these differences can be ascertained by the skilled artisan without undue experimentation from this disclosure and the knowledge in the art. Furthermore, the present invention provides in vitro systems for transcriptional analysis in canarypox or fowlpox using vaccinia virus.

RNA slot blots were used to evaluate temporal transcriptional expression in MRC-5 cells infected with the ALVAC recombinants vCP205 and vCP1431A and vCP1437A. In this analysis comparisons were made to the levels of mRNA transcribed from the HIV-I cassette encoding the env and gag proteins. ALVAC recombinants containing the E3L/K3L cassette (vCP1431A and vCP1437A) did not exhibit a significant increase in the level of mRNA for the env and gag genes above that of the ALVAC recombinant vCP205.

The previously discussed role E3L/K3L plays in the down regulation of PKR in vaccinia infected cells thereby modulating translation seems to be operative in the ALVAC recombinants containing the vaccinia E3L/K3L functions. The data has shown that translation is significantly enhanced in cells infected with ALVAC recombinants containing the E3L/K3L genes, while no significant increase in the level of transcription has been detected. This exemplifies the impact of E3L/K3L expression on translation efficiency in poxvirus infected cells.

Immunoprecipitation analyses were also performed using radiolabeled lysates derived from CEF cells infected with ALVAC parental virus, ALVAC-MN120TMG (vCP205), ALVAC-MN120TMGNPst (vCP1433), vCP1452 and vCP300, as described previously (Taylor et al., 1990), with human serum derived from HIV-seropositive individuals (anti-HIV). The analysis confirmed the expression of the envelope sequences with a molecular weight of 120 kDa and the Gag precursor protein with a molecular weight of 55 kDa in the recombinants but not in the parental virus. However, vCP300 exhibits diminished expression in comparison to vCP1452, i.e., vCP1452 surprisingly demonstrates enhanced expression due to expression of transcription and/or translation factors, in accordance with the invention.

FAC scan analysis with the Human anti-HIV antibody demonstrated expression of gp120 on the surface of HeLa cells infected with ALVAC-MN120TMGNPst (vCP1433). No fluorescence was detected on cells infected with ALVAC parental virus.

Appropriate expression of the inserted HIV genes was further confirmed by immunoprecipitation analysis (using polyclonal serum pool from HIV infected individuals) performed on a radiolabelled lysate of MRC5 cells infected with vCP1433 or vCP1452. The analysis confirmed the expression of the envelope sequences with a molecular weight of 120 KDa and the Gag precursor protein with a molecular weight of 55 KDa in vCP1452.

vCP1452 had enhanced expression on human cells in comparison to vCP1433 and vCP300. Indeed, enhanced expression was observed with the E3L/K3L translational factor in human and canine cells.

Preliminary immunogenicity studies in mice showed no evidence of enhanced immunogenicity by the E3L/K3L translational factor. This corresponds to no observed enhanced expression in murine cells.

Furthermore, in murine cells, the limiting factor of ALVAC expression is at the transcription level. Accordingly, use of an appropriate transcription factor can overcome the inability to observe enhanced expression in the murine system. Thus, the origin of the cell may be an important factor in in vitro or in vivo applications of the invention (note H4 data above), as may be the nature of the vector, e.g., the phenotype of the vector (e.g., abortive, and when abortive such as abortive early, abortive late); but, appropriate selection of a cell and vector phenotype and of time of expression of factor(s) and foreign and/or exogenous DNA are within the ambit of the skilled artisan, from this disclosure and the knowledge in the art, without undue experimentation.

ALVAC-FHV gB Recombinants

Analysis of the expression for vCP1459, vCP1460 and vCP1464 was accomplished by immunoprecipitation analysis using a sheep anti-FHV gB polyclonal sera. Human MRC-5 cells were inoculated at an moi=5 at time 0, and then pulsed for 1 hour with $^{35}S$ labelled methionine at times 3, 6, 24, 48 and 72 h p.i. The precipitated protein was separated on SDS-PAGE gels. Autoradiographs of these IPs were scanned using a densitometer. The methods used provide a semi-quantitative analysis of FHV gB expression at the specific time points.

Results show that all recombinants express the proper sized full-length, glycosylated FHV gB polypeptide (apparent MW of approximately 115 kDa). However, recombinants vCP1460 and vCP1464 show significant increase in the amount of gB protein (about 5 times) compared to vCP1459. In addition, these expression levels persist even at 72 hr p.i. Thus, it appears that the expression of vaccinia E3L/K3L in ALVAC has a significant effect on the level and persistence of FHV gB expression.

Example 4—Additional Vectors

Using the documents cited herein and the teaching herein, including in the foregoing Examples, plasmid and naked DNA vectors, and additional viral vectors, including poxvirus, e.g., NYVAC, TROVAC, ALVAC, MVA, ts (temperature sensitive) mutants, or early ($DNA^-$) and late defective mutants, adenovirus, e.g., CAV such as CAV2, herpesvirus, e.g., Epstein Barr, are generated with enhanced transcription or translation or transcription and translation, e.g., by using H4L, vaccinia D6, vaccinia A7, vaccinia G8R, vaccinia A1L, vaccinia A2L, vaccinia H5R (VLTF-1, -2, -3, -4, P3, VLTF-X) E3L, K3L, VAI, EBER, sigma 3, TRBP, or combinations thereof to modify the vector to contain at least one transcription factor or at least one translation factor or at least one transcription factor and at least one translation factor; and accordingly, enhanced expression, of exogenous coding nucleic acid molecules (such exogenous coding nucleic acid molecules including from documents cited herein or as otherwise known in the art, or from applying those teachings in conjunction with teachings herein) is obtained.

Having thus described in detail preferred embodiments of the present invention, it is to be understood that the invention defined by the appended claims is not to be limited to particular details set forth in the above description as many apparent variations thereof are possible without departing from the spirit or scope of the present invention.

References

Ahn, B-Y. and Moss, B. 1992. RNA polymerase-associated transcription specificity factor encoded by vaccinia virus. Proc. Natl. Acad. Sci. 89: 3536–3540.

Beattie, E., Denzler, K., Tartaglia, J., Paoletti, E. and Jacobs, B. L. 1995. Reversal of the interferon-sensitive phenotype of and E3L-minus vaccinia virus by expression of the reovirus S4 gene. J. Virol. 69: 499–505 ("Beattie et al. 1995a").

Beattie, E., Paoletti, E., and Tartaglia, J. 1995. Distinct Patterns of IFN Sensitivity Observed in Cells Infected with Vaccinia $K3L^-$ and $E3L^-$ Mutant Viruses. Virology 210:254–263 ("Beattie et al 1995b")

Beattie, E., Tartaglia, J. and Paoletti, E. 1991. Vaccinia virus-encoded eIF-2a homologue abrogates the antiviral effect of interferon. Virology 183: 419–422.

Carroll, K., Elroy Stein, O., Moss, B. and Jagus, R. 1993. Recombinant vaccinia virus K3L gene product prevents activation of double-stranded RNA-dependent, initiation factor 2 alpha-specific protein kinase. J. Biol. Chem. 268: 12837–12842.

Chang, H-W., Watson, J. and Jacobs, B. L. 1992. The vaccinia virus E3L gene encodes a double-stranded RNA-binding protein with inhibitory activity for the interferon-induced protein kinase. Proc. Natl. Acad. Sci. USA 89: 4825–4829.

Clark, P. A., Schwemmle, M., Schickinger, J., Hilse, K., and Clemens, M. J. 1991. Binding of Epstein-Barr virus small RNA EBER-1 to double-stranded RNA-activated protein kinase DAI. Nucleic Acids Res. 19:243–248.

Davies, M. V., Chang, H. W., Jacobs, B. L. and Kaufman, R. J. 1993. The E3L and K3L vaccinia virus gene products stimulate translation through inhibition of the double-stranded RNA-dependent protein kinase by different mechanisms. J. Virol. 67: 1688–1692.

Davies, M. V., Elroy Stein, O., Jagus, R., Moss, B. and Kaufman, R. J. 1992. The vaccinia K3L gene product potentiates translation by inhibiting double-stranded-RNA-activated protein kinase and phosphorylation of the alpha subunit of eukaryotic initiation factor 2. J. Virol. 66: 1943–1950.

Goebel, S. J., Johnson, G. P., Perkus, M. E., Davis, S. W., Winslow, J. P. and Paoletti, E. 1990. The complete DNA sequence of vaccinia virus. Virology 179: 247–266.

Harlow, E. and Lane, D. (1988). Antibodies, A Laboratory Manual. Cold Spring Harbor Laboratory. 421–470.

Hattori, M., and Sakaki, Y. (1986). Dideoxy sequencing method using denatured plasmid templates. Anal. Biochem. 152, 232–237.

Imani, F. and Jacobs, B. L. 1988. Inhibitory activity for the interferon induced protein kinase is associated with the reovirus serotype 1 s3 protein. Proc. Natl. Acad. Sci. USA 85: 7887–7891.

Jacobs, B. L. and Langland, J. O. 1996. When two strands are better than one: the mediators and modulators of the cellular responses to double-stranded RNA. Virology 219: 339–349.

Langone, J. (1982). Applications of immobilized protein A in immunochemical techniques. J. Immunol. Methods. 55. 277–296.

Mathews, M. B. and Shenk, T. 1991. Adenovirus virus-associated RNA and translation control. J. Virol. 65: 5657–5662.

Moss, B. 1990. Regulation of vaccinia virus transcription. Annu. Rev. Biochem. 59: 661–688.

Moss, B. 1992. Molecular biology of poxviruses. In Recombinant Poxviruses. Binns M. M., Smith, G. L. (eds). Boca Raton, Fla.: CRC Press; pg. 45–80.

Park, H., Davies, M. V., Langland, L. O., Chang, H-W., Nam, Y. S., Tartaglia, J., Paoletti, E., Jacobs, B. L., Kaufman, R. J. and Venkatesan, S. 1994. A cellular protein that binds several structured viral RNAs is an inhibitor of the interferon induced PKR protein kinase in vitro and in vivo. Proc. Natl. Acad. Sci. USA 91: 4713–4717.

Perkus, M., Limbach, K., Paoletti, E. (1989). Cloning and expression of foreign genes in vaccinia virus, using a host range selection system. J. Virology 63. 3829–3836.

Perkus, M. E., Tartaglia, J., and Paoletti, E. 1995. Poxvirus-based vaccine candidates for cancer, AIDS and other infectious diseases. J. of Leukocyte Biology 58: 1–13.

Sharp, T. V., Schwemmle, M., Jeffrey, I., Laing, K., Mellor, H., Proud, C. G., Hilse, K. and Clemens, M. J. 1993. Comparative analysis of the regulation of the interferon-inducible protein kinase PKR by Epstein-Barr virus RNAs EBER-1 and EBER-2 and adenovirus VAI RNA. Nucleic Acids Res. 21: 4483–4490.

Tabor, S., and Richardson, C. C. (1987). DNA sequence analysis with a modified bacteriophage T7 polymerase. Proc. Natl. Acad. Sci. USA 84, 4767–4771.

Tartaglia, J., Perkus, M. E., Taylor, J. et al. 1992. NYVAC: A highly attenuated strain of vaccinia virus. Virology 188: 217–32.

Thimmappaya, B. C., Weinberger, C., Schneider, R. J. and Shenk, T. 1982. Adenovirus VAI RNA is required for efficient translation of viral mRNAs at late times after infection. Cell 31: 543–551.

Watson, J., Chang, H-W. and Jacobs, B. L. 1991. Characterization of a vaccinia virus-induced dsRNA-binding protein that may be the inhibitor of the dsRNA-dependent protein kinase. Virology 185: 206–216.

Yuen, L, and Moss, B. (1987). Oligonucleotide sequence signaling transcriptional termination of vaccinia virus early genes. Proc. Natl. Acad. Sci. USA 84, 6417–6421.

Zhang, Y., Ahn, B-Y. and Moss, B. 1994. Targeting of a multicomponent transcription apparatus into assembling vaccinia virus particles requires RAP94, an RNA polymerase-associated protein. J. Virol. 68: 1360–1370.

What is claimed is:

1. A vector for enhanced expression of at least one first nucleic acid molecule in a cell having a particular phenotype, said vector modified to comprise the first nucleic acid molecule and at least one second nucleic acid molecule encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation.

2. The vector of claim 1 wherein the first nucleic acid molecule is operably linked to a first promoter and the second nucleic acid molecule is operably linked to a second promoter, and the first and second promoters function substantially co-temporally.

3. The vector of claim 2 wherein the first and second nucleic acid molecules are at different loci within the vector.

4. The vector of claim 2 wherein the first and second nucleic acid molecules are at the same locus within the vector.

5. The vector of claim 1 wherein the first nucleic acid molecule and the second nucleic acid molecule are operably linked to the same promoter.

6. The vector of claim 1 wherein transcription factor is of poxvirus origin.

7. The vector of claim 6 wherein the transcription factor is from a vaccinia virus.

8. The vector of claim 7 wherein the transcription factor is from an open reading frame selected from the group consisting of H4L, D6, A7, G8R, A1L, A2L, H5R, and combinations thereof.

9. The vector of claim 1 wherein the vector has a particular phenotype and the time of expression is matched with the phenotype of the vector.

10. The vector of claim 1 wherein the translation factor effects inhibition of eIF-2α phosphorylation or inhibition of PKR phosphorylation or otherwise sequesters dsRNA, decreasing the cellular dsRNA content which increases the effective concentration of dsRNA.

11. The vector of claim 10 wherein said at least one second molecule is selected from the group consisting of: a K3L open reading frame, an E3L open reading frame, a VAI RNA open reading frame, an EBER RNA open reading frame, a sigma 3 open reading frame, a TRBP open reading frame, and combinations thereof.

12. The vector of claim 1 wherein said first nucleic acid molecule encodes a molecule selected from the group consisting of an epitope of interest, a biological response modulator, a growth factor, a recognition sequence, and a fusion protein.

13. The vector of claim 1 which is a recombinant virus.

14. The vector of claim 13 which is a recombinant poxvirus.

15. The vector of claim 1 wherein the transcription factor is a viral transcription factor.

16. The vector of claim 1 wherein the translation factor is a viral translation factor.

17. The vector of claim 16 wherein the transcription factor is a viral transcription factor.

18. A vector which is vCP1452 or vCP1433.

19. A method for preparing a vector as claimed in claim 1 comprising modifying the vector to comprise the at least one second nucleic acid molecule, and optionally also modifying the vector to comprise the first nucleic acid molecule, so that there is substantially co-temporal expression of the first and second nucleic acid molecules with respect to the phenotype of the cell.

20. The method for claim 19 comprising operably linking the first nucleic acid molecule to a first promoter and the second nucleic acid molecule to a second promoter, wherein the first and second promoters are functional substantially co-temporally.

21. The method for claim 19 comprising operably linking the first and second nucleic acid molecules to a promoter.

22. An immunological, immunogenic or vaccine composition comprising the vector of claim 1 and a pharmaceutically acceptable carrier or diluent.

23. A method for generating an immunological or immunogenic response in a host comprising administering to the host the composition of claim 22.

24. A method for increasing expression of at least one first nucleic acid molecule by a vector comprising the first nucleic acid molecule, wherein the expression is in a cell having a particular phenotype, and the method comprises modifying the vector to comprise at least one second nucleic acid molecule encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation.

25. A method for expressing a gene product in vitro comprising infecting, or transfecting, a suitable cell with a vector as claimed in claim 1.

26. A method for expressing the first nucleic acid molecule in vivo comprising administering the vector of claim 1 to a host.

27. A vector for enhanced expression of at least one first nucleic acid molecule in a cell having a particular phenotype, said vector having a particular phenotype and is modified to comprise the first nucleic acid molecule and at least one second nucleic acid molecule encoding a transcription factor or encoding a transcription factor and a translation factor, wherein there is substantially co-temporal expression of the first and second nucleic acid molecules with respect to the phenotype of the cell and the time of expression is matched with the phenotype of the vector, whereby expression of the second nucleic acid molecule enhances expression of the first nucleic acid molecule by enhancing transcription or transcription and translation.

28. The vector of claim 27 wherein the first nucleic acid molecule is operably linked to a first promoter and the second nucleic acid molecule is operably linked to a second promoter, and the first and second promoters function substantially co-temporally and the time of expression is matched with the phenotype of the vector.

29. The vector of claim 28 wherein the first and second nucleic acid molecules are at different loci within the vector.

30. The vector of claim 28 wherein the first and second nucleic acid molecules are at the same locus within the vector.

31. The vector of claim 27 wherein the first nucleic acid molecule and the second nucleic acid molecule are operably linked to the same promoter.

32. The vector of claim 27 wherein transcription factor is of poxvirus origin.

33. The vector of claim 32 wherein the transcription factor is from a vaccinia virus.

34. The vector of claim 33 wherein the transcription factor is from an open reading frame selected from the group consisting of H4L, D6, A7, G8R, A1L, A2L, H5R, and combinations thereof.

35. The vector of claim 27 wherein the second nucleic acid molecule is comprised of at least one transcription factor and at least one translation factor.

36. The vector of claim 27 wherein the translation factor effects inhibition of eIF-2α phosphorylation or inhibition of PKR phosphorylation or otherwise sequesters dsRNA, decreasing the cellular dsRNA content which increases the effective concentration of dsRNA.

37. The vector of claim 36 wherein said at least one second molecule is selected from the group consisting of: a K3L open reading frame, an E3L open reading frame, a VAI RNA open reading frame, an EBER RNA open reading frame, a sigma 3 open reading frame, a TRBP open reading frame, and combinations thereof.

38. The vector of claim 27 wherein said first nucleic acid molecule encodes a molecule selected from the group consisting of an epitope of interest, a biological response modulator, a growth factor, a recognition sequence, and a fusion protein.

39. The vector of claim 27 which is a recombinant virus.

40. The vector of claim 39 which is a recombinant poxvirus.

41. A method for preparing a vector as claimed in claim 27 comprising modifying the vector to comprise the at least one second nucleic acid molecule, and optionally also modifying the vector to comprise the first nucleic acid molecule, so that there is substantially co-temporal expression of the first and second nucleic acid molecules with respect to the phenotype or the cell, and the time of expression is matched to the phenotype of the vector.

42. The method for claim 41 comprising operably linking the first nucleic acid molecule to a first promoter and the second nucleic acid molecule to a second promoter, wherein the first and second promoters are functional substantially co-temporally and the time of expression is matched to the phenotype of the vector.

43. The method for claim 41 comprising operably linking the first and second nucleic acid molecules to a promoter, wherein the first and second promoters are functional substantially co-temporally and the time of expression is matched to the phenotype of the vector.

44. An immunological, immunogenic or vaccine composition comprising the vector of claim 27 and a pharmaceutically acceptable carrier or diluent.

45. A method for generating an immunological or immunogenic response in a host comprising administering to the host the composition of claim 44.

46. A method for increasing expression of at least one first nucleic acid molecule by a vector comprising the first nucleic acid molecule, wherein the expression is in a cell having a particular phenotype and the vector has a particular phenotype, and the method comprises modifying the vector to comprise at least one second nucleic acid molecule encoding a transcription factor or encoding a transcription factor and a translation factor, wherein there is substantially co-temporal expression of the first and second nucleic acid molecules with respect to the phenotype of the cell and the time of expression is matched to the phenotype of the vector, whereby expression of the second nucleic acid molecule enhances expression of the first nucleic acid molecule by enhancing transcription or transcription and translation.

47. A method for expressing a gene product in vitro comprising infecting, or transfecting, a suitable cell with a vector as claimed in claim 27.

48. A method for expressing the first nucleic acid molecule in vivo comprising administering the vector of claim 27 to a host.

49. The vector of claim 27 wherein the transcription factor is a viral transcription factor.

50. The vector of claim 27 wherein the translation factor is a viral translation factor.

51. The vector of claim 50 wherein the transcription factor is a viral transcription factor.

* * * * *

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
(A) LENGTH: 10281 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
GCTCTTCTAG TTAGAACTTC AACTTCTTAG TATCACCTTC TATCACACCC AGCTTTCATC    60

AACATTAAAT GTGAGCGAGT AACAACCCGT CGGATTCTCC GTGGGAACAA ACGGCGGATT   120

GACCGTAATG GGATAGGTTA CGTTGGTGTA GATGGGCGCA TCGTAACCGT GCATCTGCCA   180

GTTTGAGGGG ACGACGACAG TATCGGCCTC AGGAAGATCG CACTCCAGCC AGCTTTCCGG   240

CACCGCTTCT GGTGCCGGAA ACCAGGCAAA GCGCCATTCG CCATTCAGGC TGCGCAACTG   300

TTGGGAAGGG CGATCGGTGC GGGCCTCTTC GCTATTACGC CAGCTGGCGA AAGGGGGATG   360

TGCTGCAAGG CGATTAAGTT GGGTAACGCC AGGGTTTTCC CAGTCACGAC GTTGTAAAAC   420

CATTACGATA CAAACTTAAC GGATATCGCG ATAATGAAAT AATTTATGAT TATTTCTCGC   480

TTTCAATTTA ACACAACCCT CAAGAACCTT TGTATTTATT TTCACTTTTT AAGTATAGAA   540

TAAAGAACCC GGGAAGCTTC TTTATTCTAT ACTTAAAAAG TGAAAATAAA TACAAAGGTT   600

CTTGAGGGTT GTGTTAAATT GAAAGCGAGA AATAATCATA AATTATTTCA TTATCGCGAT   660

ATCCGTTAAG TTTGTATCGT AATGGACTCT AAAGAGACTA TTCTAATTGA GATCATTCCA   720

AAAATAAAAG CATATCTACT AGACGCGAAT ATAAGTCCAA AATCCTACGA TGACTTTATT   780

TCACGAAATA AAAATATTTT CGTTATCAAC CTTTATAACG TATCGACTAT CACAGAAGAA   840

GATATACGAT TGTTATACAC TACGATAGAA CAGAATATTG ACGCGGATGA TCAAACACTG   900

GTTGCTATTT TTTCGTATAT AGGATATAAA TTTGAACAGG CTGTTAAAGA AGAGATTAGT   960
```

-continued

```
ACGAGTTTAT CCTTCAATGA CAAGAATACC ACAGATGAAA TGACGTATAA CTTGTATGAT   1020
CTTTTCTTCA ACACATTAGA CATGTATTTA CGACAAAAGA AGATCAGTAT TCTGGTAAAT   1080
GATGATGTTA GAGGTGATGT AATCGTTAGT TATAAAAATA GTGACTTAGT TTCATCATTT   1140
AATGCGGAAC TAGAACCAGA GATTAAGAAG ATACCGTTCA ATATGAAAAA TCTATTACCG   1200
TACTTGGAAA AGAATTTGGA CCAACTAAGA TTCTCTAAAA AATATTTAGA CTTTGCATAT   1260
TTATGTAGAC ACATCGGTAT TCCCATTTCC AAAAAAAAGT ATAATGTGCG ATATGTATTT   1320
CTTTATAAAA TAGACGGATT ATCCATTCCT ATTATCATTA AGGATTTTTT AGATGTTAAG   1380
TACGTATATT TGGAAAATAC TGGAAAAATT TATAAAAATT CTTTTTCCGA AGACCATAAC   1440
AACAGTCTAT CTGATTGGGG TAAAGTTATT ATACCTCTCT TAAAGGATCG TCATCTATAT   1500
AGCTACATCT TTCTATCTAG TTATCATTTA CATAGTTACT ATACAGATCT CATCGCGAGA   1560
GACGAGCCTG TGTTTGTGAA ACGCAAAAAA CTAGATATTA TAGAGATCGA TGAACCTGAG   1620
GCATGGAAAA GGGATGTTAG AGTAGAATTC GCACCGTGTG AGCATCAAAT TAGATTGAAG   1680
GAAGCTATGA AAGTTGACGC TAACTATTTC ACTAAAATTA ATAATTTTGC TAACGAATTT   1740
ATTTATTATG AAGATGGTGT GGCATATTGT AGAGTGTGTG GAATAAATAT ACCTATATTT   1800
AATTTAGATG CCGCTGACGT GATTAAAAAT ACAGTTATCG TTTCCACGTT TAACAAGACT   1860
ATATTTTTGA GCGAACCATA TAGCTATTTC GTTCATAGTC AGCGCTTTAT CTTTAATATT   1920
ATCATGTCTT TTGATAATAT TATGAAATCT CAAACTTGGG TAATGAAATA CAACATTAAC   1980
CGACTAATTC TTAACTTTCT TATTGATATA AACTCTAGAC GTCAGGAATA CGAAAAAAAG   2040
TTTTCTTCTG AAATTAAGAG AGGTCTGTTC TTTCTTCGTT TGTCTGCAAA CTTATTCGAA   2100
AGTCAAGTAT CGTCTACAGA GTTATTTTAT GTTTCCAAAA TGCTTAATTT GAACTATATA   2160
GTTGCGTTAG TAATCATTCT TAACAGTAGT GCGGACTTTA TAGTTTCCTA TATGACATCC   2220
AAGAACAAAA CGGTAGAAGA ATCCACTCTT AAATACGCCA TCTCCGTGGT TATATACGAT   2280
TTTTTGGTTA AGACTAGAAT TTGCGAGAAG GGATCGTTGG ATACTATAGT TTTATTTACC   2340
GATGTATACA CATCTATAAT GCCGGAGGAA TTGGATTTAC ATTTTCAGAG AATCACATTA   2400
GAACTTAGAA AACTAGTATC CATTCAGAGA TCGGCGTTAG AACCCAATTA CGATGTAGAA   2460
AGTCGCGGCG AAGAGCTTCC GCTATCTGCA TTAAAGTTTT TCGATACAAG CACCATTATA   2520
GTTAAAACAA TGGCTCCAGT ACATACATGT GTAGAACAAA AAATTGTTGC ACCTACTCCA   2580
TCTGTAGAAC CAACTGATGC ATCTCTTAAA AACTTCAAAG AGCTAACGTG TGACGAAGAT   2640
ATTAAGATTT TGATTAGAGT TCATGATACT AATGCTACAA AATTAGTCAT TTTTCCATCA   2700
CATCTAAAAA TAGAAATTGA GAGAAAAAAA CTAATTATAC CGCTAAAGAG TTTATATATT   2760
ACCAATACTC TCAAATATTA TTATTCTAAC TCCTATTTAT ACGTTTTCAG ATTCGGAGAT   2820
CCTATGCCAT TCGAAGAAGA ACTCATAGAT CACGAACATG TGCAATACAA AATAAATTGT   2880
TACAATATTC TAAGATATCA TTTATTGCCA GACAGTGACG TGTTTGTATA TTTTAGTAAT   2940
TCATTAAACA GAGAAGCATT GGAATACGCA TTTTATATCT TTTTGTCGAA ATATGTAAAT   3000
GTGAAACAAT GGATAGACGA AAATATAACT CGTATTAAAG AGTTGTATAT GATTAATTTC   3060
AATAACTAAA TGGCGGCGGT GAAAACTCCT GTTATTGTTG TGCCAGTTAT TGATAGACCT   3120
CCATCAGAAA CATTTCCTAA TGTTCATGAG CATATTAATG ATCAGAAGTT CGATGATGTA   3180
AAGGACAACG AAGTTATGCC AGAAAAAAGA AATGTTGTGG TAGTCAAGGA TGATCCAGAT   3240
CATTACAAGG ATTATGCGTT TATACAGTGG ACTGGAGGAA ACATTAGAAA TGATGACAAG   3300
TATACTCACT TCTTTTCAGG GTTTTGTAAC ACTATGTGTA CAGAGGAAAC GAAAAGAAAT   3360
```

-continued

```
ATCGCTAGAC ATTTAGCCCT ATGGGATTCT AATTTTTTTA CCGAGTTAGA AAATAAAAAG   3420
GTAGAATATG TAGTTATTGT AGAAAACGAT AACGTTATTG AGGATATTAC GTTTCTTCGT   3480
CCCGTCTTGA AGGCAATGCA TGACAAAAAA ATAGATATCC TACAGATGAG AGAAATTATT   3540
ACAGGCAATA AAGTTAAAAC CGAGCTTGTA ATGGACAAAA ATCATACCAT ATTCACATAT   3600
ACAGGAGGGT ATGATGTTAG CTTATCAGCC TATATTATTA GAGTTACTAC GGCGCTGAAC   3660
ATCGTAGATG AAATTATAAA GTCTGGAGGT CTATCATCGG GATTTTATTT TGAAATAGCC   3720
AGAATCGAAA ACGAAATGAA GATCAATAGG CAGATACTGG ATAATGCCGC CAAATATGTA   3780
GAACACGATC CCCGACTTGT TGCAGAACAC CGCTTCGAAA ACATGAAACC GAATTTTTGG   3840
TCTAGAATAG GAACGGCAGG ATCCACTAGT TCTAGAGCGG CCGCCACCGC GGTGGAGCTC   3900
CAGCTTTTGT TCCCTTTAGT GAGGGTTAAT TCCGAGCTTG GCGTAATCAT GGTCATAGCT   3960
GTTTCCTGTG TGAAATTGTT ATCCGCTCAC AATTCCACAC AACATACGAG CCGGAAGCAT   4020
AAAGTGTAAA GCCTGGGGTG CCTAATGAGT GAGCTAACTC ACATTAATTG CGTTGCGCTC   4080
ACTGCCCGCT TTCCAGTCGG GAAACCTGTC GTGCCAGCTG CATTAATGAA TCGGCCAACG   4140
CGCGGGGAGA GGCGGTTTGC GTATTGGGCG CTCTTCCGCT TCCTCGCTCA CTGACTCGCT   4200
GCGCTCGGTC GTTCGGCTGC GGCGAGCGGT ATCAGCTCAC TCAAAGGCGG TAATACGGTT   4260
ATCCACAGAA TCAGGGGATA ACGCAGGAAA GAACATGTGA GCAAAAGGCC AGCAAAAGGC   4320
CAGGAACCGT AAAAAGGCCG CGTTGCTGGC GTTTTTCCAT AGGCTCCGCC CCCCTGACGA   4380
GCATCACAAA AATCGACGCT CAAGTCAGAG GTGGCGAAAC CCGACAGGAC TATAAAGATA   4440
CCAGGCGTTT CCCCCTGGAA GCTCCCTCGT GCGCTCTCCT GTTCCGACCC TGCCGCTTAC   4500
CGGATACCTG TCCGCCTTTC TCCCTTCGGG AAGCGTGGCG CTTTCTCATA GCTCACGCTG   4560
TAGGTATCTC AGTTCGGTGT AGGTCGTTCG CTCCAAGCTG GGCTGTGTGC ACGAACCCCC   4620
CGTTCAGCCC GACCGCTGCG CCTTATCCGG TAACTATCGT CTTGAGTCCA ACCCGGTAAG   4680
ACACGACTTA TCGCCACTGG CAGCAGCCAC TGGTAACAGG ATTAGCAGAG CGAGGTATGT   4740
AGGCGGTGCT ACAGAGTTCT TGAAGTGGTG GCCTAACTAC GGCTACACTA GAAGGACAGT   4800
ATTTGGTATC TGCGCTCTGC TGAAGCCAGT TACCTTCGGA AAAAGAGTTG GTAGCTCTTG   4860
ATCCGGCAAA CAAACCACCG CTGGTAGCGG TGGTTTTTTT GTTTGCAAGC AGCAGATTAC   4920
GCGCAGAAAA AAAGGATCTC AAGAAGATCC TTTGATCTTT TCTACGGGGT CTGACGCTCA   4980
GTGGAACGAA AACTCACGTT AAGGGATTTT GGTCATGAGA TTATCAAAAA GGATCTTCAC   5040
CTAGATCCTT TTAAATTAAA AATGAAGTTT TAAATCAATC TAAAGTATAT ATGAGTAAAC   5100
TTGGTCTGAC AGTTACCAAT GCTTAATCAG TGAGGCACCT ATCTCAGCGA TCTGTCTATT   5160
TCGTTCATCC ATAGTTGCCT GACTCCCCGT CGTGTAGATA ACTACGATAC GGGAGGGCTT   5220
ACCATCTGGC CCCAGTGCTG CAATGATACC GCGAGACCCA CGCTCACCGG CTCCAGATTT   5280
ATCAGCAATA AACCAGCCAG CCGGAAGGGC CGAGCGCAGA AGTGGTCCTG CAACTTTATC   5340
CGCCTCCATC CAGTCTATTA ATTGTTGCCG GGAAGCTAGA GTAAGTAGTT CGCCAGTTAA   5400
TAGTTTGCGC AACGTTGTTG CCATTGCTAC AGGCATCGTG GTGTCACGCT CGTCGTTTGG   5460
TATGGCTTCA TTCAGCTCCG GTTCCCAACG ATCAAGGCGA GTTACATGAT CCCCCATGTT   5520
GTGCAAAAAA GCGGTTAGCT CCTTCGGTCC TCCGATCGTT GTCAGAAGTA AGTTGGCCGC   5580
AGTGTTATCA CTCATGGTTA TGGCAGCACT GCATAATTCT CTTACTGTCA TGCCATCCGT   5640
AAGATGCTTT TCTGTGACTG GTGAGTACTC AACCAAGTCA TTCTGAGAAT AGTGTATGCG   5700
GCGACCGAGT TGCTCTTGCC CGGCGTCAAT ACGGGATAAT ACCGCGCCAC ATAGCAGAAC   5760
```

-continued

```
TTTAAAAGTG CTCATCATTG GAAAACGTTC TTCGGGGCGA AAACTCTCAA GGATCTTACC   5820
GCTGTTGAGA TCCAGTTCGA TGTAACCCAC TCGTGCACCC AACTGATCTT CAGCATCTTT   5880
TACTTTCACC AGCGTTTCTG GGTGAGCAAA AACAGGAAGG CAAAATGCCG CAAAAAAGGG   5940
AATAAGGGCG ACACGGAAAT GTTGAATACT CATACTCTTC CTTTTTCAAT ATTATTGAAG   6000
CATTTATCAG GGTTATTGTC TCATGAGCGG ATACATATTT GAATGTATTT AGAAAAATAA   6060
ACAAATAGGG GTTCCGCGCA CATTTCCCCG AAAAGTGCCA CCTGGGACGC GCCCTGTAGC   6120
GGCGCATTAA GCGCGGCGGG TGTGGTGGTT ACGCGCAGCG TGACCGCTAC ACTTGCCAGC   6180
GCCCTAGCGC CCGCTCCTTT CGCTTTCTTC CCTTCCTTTC TCGCCACGTT CGCCGGCTTT   6240
CCCCGTCAAG CTCTAAATCG GGGGCTCCCT TTAGGGTTCC GATTTAGTGC TTTACGGCAC   6300
CTCGACCCCA AAAAACTTGA TTAGGGTGAT GGTTCACGTA GTGGGCCATC GCCCTGATAG   6360
ACGGTTTTTC GCCCTTTGAC GTTGGAGTCC ACGTTCTTTA ATAGTGGACT CTTGTTCCAA   6420
ACTGGAACAA CACTCAACCC TATCTCGGTC TATTCTTTTG ATTTATAAGG GATTTTGCCG   6480
ATTTCGGCCT ATTGGTTAAA AAATGAGCTG ATTTAACAAA AATTTAACGC GAATTTTAAC   6540
AAAATATTAA CGTTTACAAT TTCGCGCCAT TCGCCATTCA GGCTGCGCAA CTGTTGGGAA   6600
GGGCGATCGG TGCGGGCCTC TTCGCTATTA CGCCAGCTGG CGAAAGGGGG ATGTGCTGCA   6660
AGGCGATTAA GTTGGGTAAC GCCAGGGTTT TCCCAGTCAC GACGTTGTAA AACGACGGCC   6720
AGTGAATTGT AATACGACTC ACTATAGGGC GAATTGGGTA CCGGGCCCCC CCTCGAGGGA   6780
TCCTGCTTGA ACATCCTCTA GAACCGTCGA TACTGCAGAG ATTCTAGTAA TAATTTTCTT   6840
AAGATCTTTA ACGATATTGT CGGTAGCCAC CTTTAGGTCA GAAAGATCGC TTCTAGCACT   6900
ATGATTTACT TTACCAGCTT CAACTTGTAC CATAGGTTCA TCATCCCCGT CGCTATCATC   6960
GAGCTCTACA GCAGCCACGC TTTCTACAAT GTCGCCGACT CCAGGAGATG GAGAATTTTT   7020
TTCAGTTGTT TGATGATATT CCTCTATAAC TACTTCTTCT TCCACTTCCT CCTTTTTGGT   7080
TGATCTTTTA GTAGCCGCTG GTTTACGAGG AGTAGTGGCT CGTTTGGTTT TGGGCTTAGT   7140
AGATGGAATT ATTACATCTT CCGGGAAAAT ATCCTCGTTT TTATCTTTAT TTTCAGCGCT   7200
ATTTTTTAGA TGAGCTCTGA TTTCAGCCAT CTTTGTGAAG CTACTAGTAT CCGCTTTATT   7260
TGTAATTGAC CACGCCATTA CGATACAAAC TTAACGGATA TCGCGATAAT GAAATAATTT   7320
ATGATTATTT CTCGCTTTCA ATTTAACACA ACCCTCAAGA ACCTTTGTAT TTATTTTCAT   7380
TTTTTAAGTA TAGAATAAAG AATCTATAAA AACTAAAAAA ATTATACATC ATAAACCAAT   7440
TTCCTAGTTG TTTGTAACTT TAAAACGCCA CCGTCAGGGA AAGTTTCATA AGAAGCACCG   7500
GAAGAGAAGA GAATATCTCG GGACAATTGG ATCACGAGAG GCACGCAAGA GACGAATCAA   7560
CTCACGTAGA AACTCAGCAC CAGCTAGACA AGCTTCCCGG GGGATCCTTA TTTTTGACAC   7620
CAGACCAACT GGTAATGGTA GCGACCGGCG CTCAGCTGGA ATTCCGCCGA TACTGACGGG   7680
CTCCAGGAGT CGTCGCCACC AATCCCCATA TGGAAACCGT CGATATTCAG CCATGTGCCT   7740
TCTTCCGCGT GCAGCAGATG GCGATGGCTG GTTTCCATCA GTTGCTGTTG ACTGTAGCGG   7800
CTGATGTTGA ACTGGAAGTC GCCGCGCCAC TGGTGTGGGC CATAATTCAA TTCGCGCGTC   7860
CCGCAGCGCA GACCGTTTTC GCTCGGGAAG ACGTACGGGG TATACATGTC TGACAATGGC   7920
AGATCCCAGC GGTCAAAACA GGCGGCAGTA AGGCGGTCGG GATAGTTTTC TTGCGGCCCT   7980
AATCCGAGCC AGTTTACCCG CTCTGCTACC TGCGCCAGCT GGCAGTTCAG GCCAATCCGC   8040
GCCGGATGCG GTGTATCGCT CGCCACTTCA ACATCAACGG TAATCGCCAT TTGACCACTA   8100
CCATCAATCC GGTAGGTTTT CCGGCTGATA AATAAGGTTT TCCCCTGATG CTGCCACGCG   8160
```

-continued

```
TGAGCGGTCG TAATCAGCAC CGCATCAGCA AGTGTATCTG CCGTGCACTG CAACAACGCT   8220
GCTTCGGCCT GGTAATGGCC CGCCGCCTTC CAGCGTTCGA CCCAGGCGTT AGGGTCAATG   8280
CGGGTCGCTT CACTTACGCC AATGTCGTTA TCCAGCGGTG CACGGGTGAA CTGATCGCGC   8340
AGCGGCGTCA GCAGTTGTTT TTTATCGCCA ATCCACATCT GTGAAAGAAA GCCTGACTGG   8400
CGGTTAAATT GCCAACGCTT ATTACCCAGC TCGATGCAAA AATCCATTTC GCTGGTGGTC   8460
AGATGCGGGA TGGCGTGGGA CGCGGCGGGG AGCGTCACAC TGAGGTTTTC CGCCAGACGC   8520
CACTGCTGCC AGGCGCTGAT GTGCCCGGCT TCTGACCATG CGGTCGCGTT CGGTTGCACT   8580
ACGCGTACTG TGAGCCAGAG TTGCCCGGCG CTCTCCGGCT GCGGTAGTTC AGGCAGTTCA   8640
ATCAACTGTT TACCTTGTGG AGCGACATCC AGAGGCACTT CACCGCTTGC CAGCGGCTTA   8700
CCATCCAGCG CCACCATCCA GTGCAGGAGC TCGTTATCGC TATGACGGAA CAGGTATTCG   8760
CTGGTCACTT CGATGGTTTG CCCGGATAAA CGGAACTGGA AAAACTGCTG CTGGTGTTTT   8820
GCTTCCGTCA GCGCTGGATG CGGCGTGCGG TCGGCAAAGA CCAGACCGTT CATACAGAAC   8880
TGGCGATCGT TCGGCGTATC GCCAAAATCA CCGCCGTAAG CCGACCACGG GTTGCCGTTT   8940
TCATCATATT TAATCAGCGA CTGATCCACC CAGTCCCAGA CGAAGCCGCC CTGTAAACGG   9000
GGATACTGAC GAAACGCCTG CCAGTATTTA GCGAAACCGC CAAGACTGTT ACCCATCGCG   9060
TGGGCGTATT CGCAAAGGAT CAGCGGGCGC GTCTCTCCAG GTAGCGAAAG CCATTTTTTG   9120
ATGGACCATT TCGGCACAGC CGGGAAGGGC TGGTCTTCAT CCACGCGCGC GTACATCGGG   9180
CAAATAATAT CGGTGGCCGT GGTGTCGGCT CCGCCGCCTT CATACTGCAC CGGGCGGGAA   9240
GGATCGACAG ATTTGATCCA GCGATACAGC GCGTCGTGAT TAGCGCCGTG GCCTGATTCA   9300
TTCCCCAGCG ACCAGATGAT CACACTCGGG TGATTACGAT CGCGCTGCAC CATTCGCGTT   9360
ACGCGTTCGC TCATCGCCGG TAGCCAGCGC GGATCATCGG TCAGACGATT CATTGGCACC   9420
ATGCCGTGGG TTTCAATATT GGCTTCATCC ACCACATACA GGCCGTAGCG GTCGCACAGC   9480
GTGTACCACA GCGGATGGTT CGGATAATGC GAACAGCGCA CGGCGTTAAA GTTGTTCTGC   9540
TTCATCAGCA GGATATCCTG CACCATCGTC TGCTCATCCA TGACCTGACC ATGCAGAGGA   9600
TGATGCTCGT GACGGTTAAC GCCTCGAATC AGCAACGGCT TGCCGTTCAG CAGCAGCAGA   9660
CCATTTTCAA TCCGCACCTC GCGGAAACCG ACATCGCAGG CTTCTGCTTC AATCAGCGTG   9720
CCGTCGGCGG TGTGCAGTTC AACCACCGCA CGATAGAGAT TCGGGATTTC GGCGCTCCAC   9780
AGTTTCGGGT TTTCGACGTT CAGACGTAGT GTGACGCGAT CGGCATAACC ACCACGCTCA   9840
TCGATAATTT CACCGCCGAA AGGCGCGGTG CCGCTGGCGA CCTGCGTTTC ACCCTGCCAT   9900
AAAGAAACTG TTACCCGTAG GTAGTCACGC AACTCGCCGC ACATCTGAAC TTCAGCCTCC   9960
AGTACAGCGC GGCTGAAATC ATCATTAAAG CGAGTGGCAA CATGGAAATC GCTGATTTGT  10020
GTAGTCGGTT TATGCAGCAA CGAGACGTCA CGGAAAATGC CGCTCATCCG CCACATATCC  10080
TGATCTTCCA GATAACTGCC GTCACTCCAA CGCAGCACCA TCACCGCGAG GCGGTTTTCT  10140
CCGGCGCGTA AAAATGCGCT CAGGTCAAAT TCAGACGGCA AACGACTGTC CTGGCCGTAA  10200
CCGACCCAGC GCCCGTTGCA CCACAGATGA AACGCCGAGT TAACGCCATC AAAAATAATT  10260
CGCGTCTGGC CTTCCTGTAG C                                            10281
```

(2) INFORMATION FOR SEQ ID NO:2:

(i) SEQUENCE CHARACTERISTICS:
(A) LENGTH: 4259 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:2:

GCTCTAACCT TCTAGTCATT CAACTTCTTA GTATGAGCTC ACTTATTACA TCCTACTGAC 60

TATATACAGC GAATTAACCA TAGGCGTAAT TGTACAGAAA CCAGGAAATT ATTACCGCCT 120

TTTATAAGAA GTATTAATAA AACATGTAGC GTATGTCTAG AAAGAATATA CGAAAAAGAA 180

ATAAATAAAC AATATTTCGG TATTTTACCA AATTGTAAAC ACGTGTTTTG TTTTTACTGT 240

ATACAACGTT GGATGTCTAT AATAAAAGGT ACGGATACCG AAGGTACATG TCCTGTATGT 300

AGAACAGTTT CTGTATTTAT AGTGCCTAAT AGGTACTGGA TAGACGATAA ATATGAAAAG 360

AGATTAATTA TAAATAAATA TAAGAATGAC AGAAAGACTT ATAAAGCGTT TAAACATTAT 420

ATAGGAAGAT ACGTATTATT TTATACAGTA AACAACAGTT TATTTGTTAC TAATGATTAA 480

GGTACGTGAC TAATTAGCTA TAAAAAGGAT CCATCGATGA TGGGAAGCTT CTTTATTCTA 540

TACTTAAAAA GTGAAAATAA ATACAAAGGT TCTTGAGGGT TGTGTTAAAT TGAAAGCGAG 600

AAATAATCAT AAATTATTTC ATTATCGCGA TATCCGTTAA GTTTGTATCG TAATGGACTC 660

TAAAGAGACT ATTCTAATTG AGATCATTCC AAAAATAAAA GCATATCTAC TAGACGCGAA 720

TATAAGTCCA AAATCCTACG ATGACTTTAT TTCACGAAAT AAAAATATTT TCGTTATCAA 780

CCTTTATAAC GTATCGACTA TCACAGAAGA AGATATACGA TTGTTATACA CTACGATAGA 840

ACAGAATATT GACGCGGATG ATCAAACACT GGTTGCTATT TTTTCGTATA TAGGATATAA 900

ATTTGAACAG GCTGTTAAAG AAGAGATTAG TACGAGTTTA TCCTTCAATG ACAAGAATAC 960

CACAGATGAA ATGACGTATA ACTTGTATGA TCTTTTCTTC AACACATTAG ACATGTATTT 1020

ACGACAAAAG AAGATCAGTA TTCTGGTAAA TGATGATGTT AGAGGTGATG TAATCGTTAG 1080

TTATAAAAAT AGTGACTTAG TTTCATCATT TAATGCGGAA CTAGAACCAG AGATTAAGAA 1140

GATACCGTTC AATATGAAAA ATCTATTACC GTACTTGGAA AAGAATTTGG ACCAACTAAG 1200

ATTCTCTAAA AAATATTTAG ACTTTGCATA TTTATGTAGA CACATCGGTA TTCCCATTTC 1260

CAAAAAAAAG TATAATGTGC GATATGTATT TCTTTATAAA ATAGACGGAT TATCCATTCC 1320

TATTATCATT AAGGATTTTT TAGATGTTAA GTACGTATAT TTGGAAAATA CTGGAAAAAT 1380

TTATAAAAAT TCTTTTTCCG AAGACCATAA CAACAGTCTA TCTGATTGGG GTAAAGTTAT 1440

TATACCTCTC TTAAAGGATC GTCATCTATA TAGCTACATC TTTCTATCTA GTTATCATTT 1500

ACATAGTTAC TATACAGATC TCATCGCGAG AGACGAGCCT GTGTTTGTGA AACGCAAAAA 1560

ACTAGATATT ATAGAGATCG ATGAACCTGA GGCATGGAAA AGGGATGTTA GAGTAGAATT 1620

CGCACCGTGT GAGCATCAAA TTAGATTGAA GGAAGCTATG AAAGTTGACG CTAACTATTT 1680

CACTAAAATT AATAATTTTG CTAACGAATT TATTTATTAT GAAGATGGTG TGGCATATTG 1740

TAGAGTGTGT GGAATAAATA TACCTATATT TAATTTAGAT GCCGCTGACG TGATTAAAAA 1800

TACAGTTATC GTTTCCACGT TTAACAAGAC TATATTTTTG AGCGAACCAT ATAGCTATTT 1860

CGTTCATAGT CAGCGCTTTA TCTTTAATAT TATCATGTCT TTTGATAATA TTATGAAATC 1920

TCAAACTTGG GTAATGAAAT ACAACATTAA CCGACTAATT CTTAACTTTC TTATTGATAT 1980

AAACTCTAGA CGTCAGGAAT ACGAAAAAAA GTTTTCTTCT GAAATTAAGA GAGGTCTGTT 2040

CTTTCTTCGT TTGTCTGCAA ACTTATTCGA AAGTCAAGTA TCGTCTACAG AGTTATTTTA 2100

TGTTTCCAAA ATGCTTAATT TGAACTATAT AGTTGCGTTA GTAATCATTC TTAACAGTAG 2160

TGCGGACTTT ATAGTTTCCT ATATGACATC CAAGAACAAA ACGGTAGAAG AATCCACTCT 2220

TAAATACGCC ATCTCCGTGG TTATATACGA TTTTTTGGTT AAGACTAGAA TTTGCGAGAA 2280

```
GGGATCGTTG GATACTATAG TTTTATTTAC CGATGTATAC ACATCTATAA TGCCGGAGGA   2340

ATTGGATTTA CATTTTCAGA GAATCACATT AGAACTTAGA AAACTAGTAT CCATTCAGAG   2400

ATCGGCGTTA GAACCCAATT ACGATGTAGA AAGTCGCGGC GAAGAGCTTC CGCTATCTGC   2460

ATTAAAGTTT TTCGATACAA GCACCATTAT AGTTAAAACA ATGGCTCCAG TACATACATG   2520

TGTAGAACAA AAAATTGTTG CACCTACTCC ATCTGTAGAA CCAACTGATG CATCTCTTAA   2580

AAACTTCAAA GAGCTAACGT GTGACGAAGA TATTAAGATT TTGATTAGAG TTCATGATAC   2640

TAATGCTACA AAATTAGTCA TTTTTCCATC ACATCTAAAA ATAGAAATTG AGAGAAAAAA   2700

ACTAATTATA CCGCTAAAGA GTTTATATAT TACCAATACT CTCAAATATT ATTATTCTAA   2760

CTCCTATTTA TACGTTTTCA GATTCGGAGA TCCTATGCCA TTCGAAGAAG AACTCATAGA   2820

TCACGAACAT GTGCAATACA AAATAAATTG TTACAATATT CTAAGATATC ATTTATTGCC   2880

AGACAGTGAC GTGTTTGTAT ATTTTAGTAA TTCATTAAAC AGAGAAGCAT TGGAATACGC   2940

ATTTTATATC TTTTTGTCGA AATATGTAAA TGTGAAACAA TGGATAGACG AAAATATAAC   3000

TCGTATTAAA GAGTTGTATA TGATTAATTT CAATAACTAA AAGCTTCCCA TCCTGCAGCT   3060

CGAGTTTTTA TGACTAGTTA ATCACGGCCG CTCAATATTG TATTGGATGG TTAGAGATCA   3120

AAGGATACAA GATAACTGGG CTCATTTCAG CTTTACATTC ATCCCTATAA GCTTTCATAA   3180

TGGGATTTTT CTCCATAATG TCAAAATCAC TTTGGATATA TTCAAAATTT TCTACAAAAT   3240

GTTTTGGTTG TTCTGAGCTA AACACGATGT TAGATATTAA TAACTTTGCT ATCTCAAGAC   3300

CTTCTGAAGT ATCAACTTTG ATATTGGAAA GAGGTGTAAA ATAAGGTGAT GAAGCGATTG   3360

TTGTATCTGC ACAGAATGTT AACAGTATAT CTACTAATTC TACATTTCCA TCTGTCACAG   3420

CATGCCATAG AGGAGTATTC CAGTACCTGT CCTTAGCATT TATATCAGCA CCGAATTCCA   3480

AAAGCATAAT AGTTATCTTT ACAGATCCTA TACACACAGC ATAATGCAAA GGAGTCATCC   3540

TATGGCTATC TTTAACGTTA GTATATGCTC CAGCTAGAAG TAATTGCTCT ATTATCTCCA   3600

TGTTTTCAGA TTTAACAGCA TAATGCAATG GATACATATA TCCTCTGTAA CCATAATTTA   3660

TACTCGATCC AGCTTTTAGT AACATACTCA CAATTTCCAA ATTTTCTCTC TTTATAGCCT   3720

CGATTATGGG ATGATTTTCC CTGTACTCAT TGTCAACATC AGCGTTATAC TCCAGAAGTA   3780

ACTTTACAAT TTCCACATTC TCTATAGAGA CAGCATACTG GAGTGGAGTC TTTACTTTGT   3840

AGTCCTCATA TGTATCCACA TTAGCGCCAT GATCCAACAA GAGTTTCACC AGATCTATGT   3900

TCTGAACTTT GACAGCTCTA TGCAACGGAG AAGATACTTG TTCGCTAGAT ATATCAGGAT   3960

CAGCTCCTGC TAACAATAGA GCTTTGGCTA TTTCAAATTT TTCATTTTCT ACAGCACAAT   4020

GAAGGGGTGA GCAGCCATAA TCGTTGAATA CGTCCAGGTT AATGCCGGTT TTCACAATAT   4080

CTAGCACGCT AGACAGAGAT CCAGATTCAA TAGCTTCGAA TAAGTATGCC TCCATTTTGT   4140

GTAATAGTAG TAAGTAATAA TTTTCTGAAG AAACTACTAA CTTACCGAGC TATAGTAGAT   4200

AGTTATAATT TCATTTTTTT ACAAGTAGTA TCACATAGTG ATTGCTTATT AAAGGTACC    4259
```

(2) INFORMATION FOR SEQ ID NO:3:

(i) SEQUENCE CHARACTERISTICS:
(A) LENGTH: 4472 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

-continued

```
GCTCTAACCT TCTAGTACAT TCAACTTCTT AGTACTCCGA GCTCGCGGCC GCCTATCAAA     60
AGTCTTAATG AGTTAGGTGT AGATAGTATA GATATTACTA CAAAGGTATT CATATTTCCT    120
ATCAATTCTA AAGTAGATGA TATTAATAAC TCAAAGATGA TGATAGTAGA TAATAGATAC    180
GCTCATATAA TGACTGCAAA TTTGGACGGT TCACATTTTA ATCATCACGC GTTCATAAGT    240
TTCAACTGCA TAGATCAAAA TCTCACTAAA AAGATAGCCG ATGTATTTGA GAGAGATTGG    300
ACATCTAACT ACGCTAAAGA AATTACAGTT ATAAATAATA CATAATGGAT TTTGTTATCA    360
TCAGTTATAT TTAACATAAG TACAATAAAA AGTATTAAAT AAAAATACTT ACTTACGAAA    420
AAATGACTAA TTAGCTATAA AAACCCAGAT CTCTCGAGGT CGACGGTATC GATAAGCTTG    480
ATATCGAATT CATAAAAATT ATTGATGTCT ACACATCCTT TTGTAATTGA CATCTATATA    540
TCCTTTTGTA TAATCAACTC TAATCACTTT AACTTTTACA GTTTTCCCTA CCAGTTTATC    600
CCTATATTCA ACATATCTAT CCATATGCAT CTTAACACTC TCTGCCAAGA TAGCTTCAGA    660
GTGAGGATAG TCAAAAAGAT AAATGTATAG AGCATAATCC TTCTCGTATA CTCTGCCCTT    720
TATTACATCG CCCGCATTGG GCAACGAATA ACAAAATGCA AGCATACGAT ACAAACTTAA    780
CGGATATCGC GATAATGAAA TAATTTATGA TTATTTCTCG CTTTCAATTT AACACAACCC    840
TCAAGAACCT TTGTATTTAT TTTCACTTTT TAAGTATAGA ATAAAGAAAG CTCTAATTAA    900
TTAATGAACA GATTGTTTCG TTTTCCCCTT GGCGTATCAC TAATTAATTA ACCCGGGCTG    960
CAGCTCGAGG AATTCAACTA TATCGACATA TTTCATTTGT ATACACATAA CCATTACTAA   1020
CGTAGAATGT ATAGGAAGAG ATGTAACGGG AACAGGGTTT GTTGATTCGC AAACTATTCT   1080
AATACATAAT TCTTCTGTTA ATACGTCTTG CACGTAATCT ATTATAGATG CCAAGATATC   1140
TATATAATTA TTTTGTAAGA TGATGTTAAC TATGTGATCT ATATAAGTAG TGTAATAATT   1200
CATGTATTTC GATATATGTT CCAACTCTGT CTTTGTGATG TCTAGTTTCG TAATATCTAT   1260
AGCATCCTCA AAAAATATAT TCGCATATAT TCCCAAGTCT TCAGTTCTAT CTTCTAAAAA   1320
ATCTTCAACG TATGGAATAT AATAATCTAT TTTACCTCTT CTGATATCAT TAATGATATA   1380
GTTTTTGACA CTATCTTCTG TCAATTGATT CTTATTCACT ATATCTAAGA AACGGATAGC   1440
GTCCCTAGGA CGAACTACTG CCATTAATAT CTCTATTATA GCTTCTGGAC ATAATTCATC   1500
TATTATACCA GAATTAATGG GAACTATTCC GTATCTATCT AACATAGTTT TAAGAAAGTC   1560
AGAATCTAAG ACCTGATGTT CATATATTGG TTCATACATG AAATGATCTC TATTGATGAT   1620
AGTGACTATT TCATTCTCTG AAAATTGGTA ACTCATTCTA TATATGCTTT CCTTGTTGAT   1680
GAAGGATAGA ATATACTCAA TAGAATTTGT ACCAACAAAC TGTTCTCTTA TGAATCGTAT   1740
ATCATCATCT GAAATAATCA TGTAAGGCAT ACATTTAACA ATTAGAGACT TGTCTCCTGT   1800
TATCAATATA CTATTCTTGT GATAATTTAT GTGTGAGGCA AATTTGTCCA CGTTCTTTAA   1860
TTTTGTTATA GTAGATATCA AATCCAATGG AGCTACAGTT CTTGGCTTAA ACAGATATAG   1920
TTTTTCTGGA ACAAATTCTA CAACATTATT ATAAAGGACT TTGGGTAGAT AAGTGGGATG   1980
AAATCCTATT TTAATTAATG CTATCGCATT GTCCTCGTGC AAATATCCAA ACGCTTTTGT   2040
GATAGTATGG CATTCATTGT CTAGAAACGC TCTACGAATA TCTGTGACAG ATATCATCTT   2100
TAGAGAATAT ACTAGTCGCG TTAATAGTAC TACAATTTGT ATTTTTTAAT CTATCTCAAT   2160
AAAAAAATTA ATATGTATGA TTCAATGTAT AACTAAACTA CTAACTGTTA TTGATAACTA   2220
GAATCAGAAT CTAATGATGA CGTAACCAAG AAGTTTATCT ACTGCCAATT TAGCTGCATT   2280
ATTTTTAGCA TCTCGTTTAG ATTTTCCATC TGCCTTATCG AATACTCTTC CGTCGATGTC   2340
TACACAGGCA TAAAATGTAG GAGAGTTACT AGGCCCAACT GATTCAATAC GAAAAGACCA   2400
```

-continued

```
ATCTCTCTTA GTTATTTGGC AGTACTCATT AATAATGGTG ACAGGGTTAG CATCTTTCCA   2460

ATCAATAATT TTTTTAGCCG GAATAACATC ATCAAAAGAC TTATGATCCT CTCTCATTGA   2520

TTTTTCGCGG GATACATCAT CTATTATGAC GTCAGCCATA GCATCAGCAT CCGGCTTATC   2580

CGCCTCCGTT GTCATAAACC AACGAGGAGG AATATCGTCG GAGCTGTACA CCATAGCACT   2640

ACGTTGAAGA TCGTACAGAG CTTTATTAAC TTCTCGCTTC TCCATATTAA GTTGTCTAGT   2700

TAGTTGTGCA GCAGTAGCTC CTTCGATTCC AATGTTTTTA ATAGCCGCAC ACACAATCTC   2760

TGCGTCAGAA CGCTCGTCAA TATAGATCTT AGACATTTTT AGAGAGAACT AACACAACCA   2820

GCAATAAAAC TGAACCTACT TTATCATTTT TTTATTCATC ATCCTCTGGT GGTTCGTCGT   2880

TTCTATCGAA TGTAGCTCTG ATTAACCCGT CATCTATAGG TGATGCTGGT TCTGGAGATT   2940

CTGGAGGAGA TGGATTATTA TCTGGAAGAA TCTCTGTTAT TTCCTTGTTT TCATGTATCG   3000

ATTGCGTTGT AACATTAAGA TTGCGAAATG CTCTAAATTT GGGAGGCTTA AAGTGTTGTT   3060

TGCAATCTCT ACACGCGTGT CTAACTAGTG GAGGTTCGTC AGCTGCTCTA GTTTGAATCA   3120

TCATCGGCGT AGTATTCCTA CTTTTACAGT TAGGACACGG TGTATTGTAT TTCTCGTCGA   3180

GAACGTTAAA ATAATCGTTG TAACTCACAT CCTTTATTTT ATCTATATTG TATTCTACTC   3240

CTTTCTTAAT GCATTTTATA CCGAATAAGA GATAGCGAAG GAATTCTTTT TATTGATTAA   3300

CTAGTCAAAT GAGTATATAT AATTGAAAAA GTAAAATATA AATCATATAA TAATGAAACG   3360

AAATATCAGT AATAGACAGG AACTGGCAGA TTCTTCTTCT AATGAAGTAA GTACTGCTAA   3420

ATCTCCAAAA TTAGATAAAA ATGATACAGC AAATACAGCT TCATTCAACG AATTACCTTT   3480

TAATTTTTTC AGACACACCT TATTACAAAC TAACTAAGTC AGATGATGAG AAAGTAAATA   3540

TAAATTTAAC TTATGGGTAT AATATAATAA AGATTCATGA TATTAATAAT TTACTTAACG   3600

ATGTTAATAG ACTTATTCCA TCAACCCCTT CAAACCTTTC TGGATATTAT AAAATACCAG   3660

TTAATGATAT TAAAATAGAT TGTTTAAGAG ATGTAAATAA TTATTTGGAG GTAAAGGATA   3720

TAAAATTAGT CTATCTTTCA CATGGAAATG AATTACCTAA TATTAATAAT TATGATAGGA   3780

ATTTTTTAGG ATTTACAGCT GTTATATGTA TCAACAATAC AGGCAGATCT ATGGTTATGG   3840

TAAAACACTG TAACGGGAAG CAGCATTCTA TGGTAACTGG CCTATGTTTA ATAGCCAGAT   3900

CATTTTACTC TATAAACATT TTACCACAAA TAATAGGATC CTCTAGATAT TTAATATTAT   3960

ATCTAACAAC AACAAAAAAA TTTAACGATG TATGGCCAGA AGTATTTTCT ACTAATAAAG   4020

ATAAAGATAG TCTATCTTAT CTACAAGATA TGAAAGAAGA TAATCATTTA GTAGTAGCTA   4080

CTAATATGGA AAGAAATGTA TACAAAAACG TGGAAGCTTT TATATTAAAT AGCATATTAC   4140

TAGAAGATTT AAAATCTAGA CTTAGTATAA CAAAACAGTT AAATGCCAAT ATCGATTCTA   4200

TATTTCATCA TAACAGTAGT ACATTAATCA GTGATATACT GAAACGATCT ACAGACTCAA   4260

CTATGCAAGG AATAAGCAAT ATGCCAATTA TGTCTAATAT TTTAACTTTA GAACTAAAAC   4320

GTTCTACCAA TACTAAAAAT AGGATACGTG ATAGGCTGTT AAAAGCTGCA ATAAATAGTA   4380

AGGATGTAGA AGAAATACTT TGTTCTATAC CTTCGGAGGA AAGAACTTTA GAACAACTTA   4440

AGTTTAATCA AACTTGTATT TATGAAGGTA CC                                 4472
```

(2) INFORMATION FOR SEQ ID NO:4:

(i) SEQUENCE CHARACTERISTICS:
(A) LENGTH: 2856 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

GACTCGGGTT TTATGTCCAC TCGTGGCGAT CTTGGGAAGC GGCGACGAGG GAGTCGTTGG 60

CAGGGACACA GTGGCTATTT TCGACAGAGA TGTTTTTTCC CTTCTCTACT CGGTATTGCA 120

GCGACTGGCT CCAGACATGG TAACGGATCG TCGGGATTAA CCAGACTAGC TAGATATGTT 180

TCATTTATCT GGATCGTACT ATTCTTAGTC GGTCCCCGTC CAGTAGAGGG TCAATCTGGA 240

AGCACATCGG AACAACCCCG GCGGACTGTA GCTACCCCTG AGGTAGGGGG TACACCACCA 300

AAACCAACTA CAGATCCCAC CGATATGTCG GATATGAGGG AAGCTCTCCG TGCGTCCCAA 360

ATAGAGGCTA ACGGACCATC GACTTTCTAT ATGTGTCCAC CACCTTCAGG ATCTACTGTC 420

GTGCGTTTAG AGCCACCACG GGCCTGTCCA GATTATAAAC TAGGGAAAAA TTTTACCGAG 480

GGTATAGCTG TAATATTTAA AGAAAATATA GCGCCATATA AATTCAAGGC AAATATATAC 540

TATAAAAACA TTATTATGAC AACGGTATGG TCTGGGAGTT CCTATGCCGT TACAACCAAC 600

CGATATACAG ACAGGGTTCC CGTGAAAGTT CAAGAGATTA CAGATCTCAT AGATAGACGG 660

GGTATGTGCC TCTCGAAAGC TGATTACGTT CGTAACAATT ATCAATTTAC GGCCTTTGAT 720

CGAGACGAGG ATCCCAGAGA ACTGCCTCTG AAACCCTCCA AGTTCAACAC TCCAGAGTCC 780

CGTGGATGGC ACACCACCAA TGAAACATAC ACAAAGATCG GTGCTGCTGG ATTTCACCAC 840

TCTGGGACCT CTGTAAATTG CATCGTAGAG GAAGTGGATG CAAGATCTGT ATATCCATAT 900

GACTCATTTG CTATCTCCAC TGGTGACGTG ATTCACATGT CTCCATTCTT TGGGCTGAGG 960

GATGGAGCCC ATGTAGAACA TACTAGTTAT TCTTCAGACA GATTTCAACA AATCGAGGGA 1020

TACTATCCAA TAGACTTGGA TACGCGATTA CAACTGGGGG CACCAGTTTC TCGCAATTTT 1080

TTGGAAACTC CGCATGTGAC AGTGGCCTGG AACTGGACCC CAAAGTCTGG TCGGGTATGT 1140

ACCTTAGCCA AATGGAGGGA AATAGATGAA ATGCTACGCG ATGAATATCA GGGCTCCTAT 1200

AGATTTACAG CCAAGACCAT ATCCGCTACT TTCATCTCCA ATACTTCACA ATTTGAAATC 1260

AATCGTATCC GTTTGGGGGA CTGTGCCACC AAGGAGGCAG CCGAAGCCAT AGACCGGATT 1320

TATAAGAGTA AATATAGTAA AACTCATATT CAGACTGGAA CCCTGGAGAC CTACCTAGCC 1380

CGTGGGGGAT TTCTAATAGC TTTCCGTCCC ATGATCAGCA ACGAACTAGC AAAGTTATAT 1440

ATCAATGAAT TAGCACGTTC CAATCGCACG GTAGATCTCA GTGCACTCCT CAATCCATCT 1500

GGGGAAACAG TACAACGAAC TAGAAGATCG GTCCCATCTA ATCAACATCA TAGGTCGCGG 1560

CGCAGCACAA TAGAGGGGGG TATAGAAACC GTGAACAATG CATCACTCCT CAAGACCACC 1620

TCATCTGTGG AATTCGCAAT GCTACAATTT GCCTATGACT ACATACAAGC CCATGTAAAT 1680

GAAATGTTGA GTCGGATAGC CACTGCCTGG TGTACACTTC AGAACCGCGA ACATGTGCTG 1740

TGGACAGAGA CCCTAAAACT CAATCCCGGT GGGGTGGTCT CGATGGCCCT AGAACGTCGT 1800

GTATCCGCGC GCCTACTTGG AGATGCCGTC GCCGTAACAC AATGTGTTAA CATTTCTAGC 1860

GGACATGTCT ATATCCAAAA TTCTATGCGG GTGACGGGTT CATCAACGAC ATGTTACAGC 1920

CGCCCTCTTG TTTCCTTCCG TGCCCTCAAT GACTCCGAAT ACATAGAAGG ACAACTAGGG 1980

GAAAACAATG AACTTCTCGT GGAACGAAAA CTAATTGAGC CTTGCACTGT CAATAATAAG 2040

CGGTATTTTA AGTTTGGGGC AGATTATGTA TATTTTGAGG ATTATGCGTA TGTCCGTAAA 2100

GTCCCGCTAT CGGAGATAGA ACTGATAAGT GCGTATGTGA ATTTAAATCT TACTCTCCTA 2160

GAGGATCGTG AATTTCTCCC ACTCGAAGTT TATACACGAG CTGAGCTGGA AGATACCGGC 2220

CTTTTGGACT ACAGCGAGAT TCAACGCCGC AACCAACTCC ACGCCTTAAA ATTTTATGAT 2280

ATAGACAGCA TAGTCAGAGT GGATAATAAT CTTGTCATCA TGCGTGGTAT GGCAAATTTC 2340

-continued

```
TTTCAGGGAC TCGGGGATGT GGGGGCTGGT TTCGGCAAGG TGGTCTTAGG GGCTGCGAGT   2400

GCGGTAATCT CAACAGTATC AGGCGTATCA TCATTTCTAA ACAACCCATT TGGAGCATTG   2460

GCCGTGGGAC TGTTAATATT AGCTGGCATC GTCGCAGCAT TCCTGGCATA TCGCTATATA   2520

TCTAGATTAC GTGCAAATCC AATGAAAGCC TTATATCCTG TGACGACTAG GAATTTGAAA   2580

CAGACGCTAA GAGCCCGCTC AACGGCTGGT GGGGATAGCG ACCCGGGAGT CGATGACTTC   2640

GATGAGGAAA AGCTAATGCA GGCAAGGGAG ATGATAAAAT ATATGTCCCT CGTATCGGCT   2700

ATGGAGCAAC AAGAACATAA GGCGATGAAA AAGAATAAGG GCCCAGCGAT CCTAACGAGT   2760

CATCTCACTA ACATGGCCCT CCGTCGCCGT GGACCTAAAT ACCAACGCCT CAATAATCTT   2820

GATAGCGGTG ATGATACTGA AACAAATCTT GTCTAA                             2856
```

(2) INFORMATION FOR SEQ ID NO:5:

(i) SEQUENCE CHARACTERISTICS:
(A) LENGTH: 6649 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

```
GACTTTGACT GCGGCTACGT AGCGGCCGCG TCGACATGCA TTGTTAGTTC TGTAGATCAG     60

TAACGTATAG CATACGAGTA TAATTATCGT AGGTAGTAGG TATCCTAAAA TAAATCTGAT    120

ACAGATAATA ACTTTGTAAA TCAATTCAGC AATTTCTCTA TTATCATGAT AATGATTAAT    180

ACACAGCGTG TCGTTATTTT TTGTTACGAT AGTATTTCTA AAGTAAAGAG CAGGAATCCC    240

TAGTATAATA GAAATAATCC ATATGAAAAA TATAGTAATG TACATATTTC TAATGTTAAC    300

ATATTTATAG GTAAATCCAG GAAGGGTAAT TTTTACATAT CTATATACGC TTATTACAGT    360

TATTAAAAAT ATACTTGCAA ACATGTTAGA AGTAAAAAAG AAAGAACTAA TTTTACAAAG    420

TGCTTTACCA AAATGCCAAT GGAAATTACT TAGTATGTAT ATAATGTATA AAGGTATGAA    480

TATCACAAAC AGCAAATCGG CTATTCCCAA GTTGAGAAAC GGTATAATAG ATATATTTCT    540

AGATACCATT AATAACCTTA TAAGCTTGAC GTTTCCTATA ATGCCTACTA AGAAAACTAG    600

AAGATACATA CATACTAACG CCATACGAGA GTAACTACTC ATCGTATAAC TACTGTTGCT    660

AACAGTGACA CTGATGTTAT AACTCATCTT TGATGTGGTA TAAATGTATA ATAACTATAT    720

TACACTGGTA TTTTATTTCA GTTATATACT ATATAGTATT AAAAATTATA TTTGTATAAT    780

TATATTATTA TATTCAGTGT AGAAAGTAAA ATACTATAAA TATGTATCTC TTATTTATAA    840

CTTATTAGTA AAGTATGTAC TATTCAGTTA TATTGTTTTA TAAAAGCTAA ATGCTACTAG    900

ATTGATATAA ATGAATATGT AATAAATTAG TAATGTAGTA TACTAATATT AACTCACATT    960

TGACTAATTA GCTATAAAAA CCCGGGCTGC AGCCCGGGAA GCTTACAAAA ATTAGACAAG   1020

ATTTGTTTCA GTATCATCAC CGCTATCAAG ATTATTGAGG CGTTGGTATT TAGGTCCACG   1080

GCGACGGAGG GCCATGTTAG TGAGATGACT CGTTAGGATC GCTGGGCCCT TATTCTTTTT   1140

CATCGCCTTA TGTTCTTGTT GCTCCATAGC CGATACGAGG GACATATATT TTATCATCTC   1200

CCTTGCCTGC ATTAGCTTTT CCTCATCGAA GTCATCGACT CCCGGGTCGC TATCCCCACC   1260

AGCCGTTGAG CGGGCTCTTA GCGTCTGTTT CAAATTCCTA GTCGTCACAG GATATAAGGC   1320

TTTCATTGGA TTTGCACGTA ATCTAGATAT ATAGCGATAT GCCAGGAATG CTGCGACGAT   1380

GCCAGCTAAT ATTAACAGTC CCACGGCCAA TGCTCCAAAT GGGTTGTTTA GAAATGATGA   1440
```

-continued

```
TACGCCTGAT ACTGTTGAGA TTACCGCACT CGCAGCCCCT AAGACCACCT TGCCGAAACC   1500
AGCCCCCACA TCCCCGAGTC CCTGAAAGAA ATTTGCCATA CCACGCATGA TGACAAGATT   1560
ATTATCCACT CTGACTATGC TGTCTATATC ATAAAATTTT AAGGCGTGGA GTTGGTTGCG   1620
GCGTTGAATC TCGCTGTAGT CCAAAAGGCC GGTATCTTCC AGCTCAGCTC GTGTATAAAC   1680
TTCGAGTGGG AGAAATTCAC GATCCTCTAG GAGAGTAAGA TTTAAATTCA CATACGCACT   1740
TATCAGTTCT ATCTCCGATA GCGGGACTTT ACGGACATAC GCATAATCCT CAAAATATAC   1800
ATAATCTGCC CCAAACTTAA AATACCGCTT ATTATTGACA GTGCAAGGCT CAATTAGTTT   1860
TCGTTCCACG AGAAGTTCAT TGTTTTCCCC TAGTTGTCCT TCTATGTATT CGGAGTCATT   1920
GAGGGCACGG AAGGAAACAA GAGGGCGGCT GTAACATGTC GTTGATGAAC CCGTCACCCG   1980
CATAGAATTT TGGATATAGA CATGTCCGCT AGAAATGTTA ACACATTGTG TTACGGCGAC   2040
GGCATCTCCA AGTAGGCGCG CGGATACACG ACGTTCTAGG GCCATCGAGA CCACCCCACC   2100
GGGATTGAGT TTTAGGGTCT CTGTCCACAG CACATGTTCG CGGTTCTGAA GTGTACACCA   2160
GGCAGTGGCT ATCCGACTCA ACATTTCATT TACATGGGCT TGTATGTAGT CATAGGCAAA   2220
TTGTAGCATT GCGAATTCCA CAGATGAGGT GGTCTTGAGG AGTGATGCAT TGTTCACGGT   2280
TTCTATACCC CCCTCTATTG TGCTGCGCCG CGACCTATGA TGTTGATTAG ATGGGACCGA   2340
TCTTCTAGTT CGTTGTACTG TTTCCCCAGA TGGATTGAGG AGTGCACTGA GATCTACCGT   2400
GCGATTGGAA CGTGCTAATT CATTGATATA TAACTTTGCT AGTTCGTTGC TGATCATGGG   2460
ACGGAAAGCT ATTAGAAATC CCCCACGGGC TAGGTAGGTC TCCAGGGTTC CAGTCTGAAT   2520
ATGAGTTTTA CTATATTTAC TCTTATAAAT CCGGTCTATG GCTTCGGCTG CCTCCTTGGT   2580
GGCACAGTCC CCCAAACGGA TACGATTGAT TTCAAATTGT GAAGTATTGG AGATGAAAGT   2640
AGCGGATATG GTCTTGGCTG TAAATCTATA GGAGCCCTGA TATTCATCGC GTAGCATTTC   2700
ATCTATTTCC CTCCATTTGG CTAAGGTACA TACCCGACCA GACTTTGGGG TCCAGTTCCA   2760
GGCCACTGTC ACATGCGGAG TTTCCAAAAA ATTGCGAGAA ACTGGTGCCC CCAGTTGTAA   2820
TCGCGTATCC AAGTCTATTG GATAGTATCC CTCGATTTGT TGAAATCTGT CTGAAGAATA   2880
ACTAGTATGT TCTACATGGG CTCCATCCCT CAGCCCAAAG AATGGAGACA TGTGAATCAC   2940
GTCACCAGTG GAGATAGCAA ATGAGTCATA TGGATATACA GATCTTGCAT CCACTTCCTC   3000
TACGATGCAA TTTACAGAGG TCCCAGAGTG GTGAAATCCA GCAGCACCGA TCTTTGTGTA   3060
TGTTTCATTG GTGGTGTGCC ATCCACGGGA CTCTGGAGTG TTGAACTTGG AGGGTTTCAG   3120
AGGCAGTTCT CTGGGATCCT CGTCTCGATC AAAGGCCGTA AATTGATAAT TGTTACGAAC   3180
GTAATCAGCT TTCGAGAGGC ACATACCCCG TCTATCTATG AGATCTGTAA TCTCTTGAAC   3240
TTTCACGGGA ACCCTGTCTG TATATCGGTT GGTTGTAACG GCATAGGAAC TCCCAGACCA   3300
TACCGTTGTC ATAATAATGT TTTTATAGTA TATATTTGCC TTGAATTTAT ATGGCGCTAT   3360
ATTTTCTTTA AATATTACAG CTATACCCTC GGTAAAATTT TTCCCTAGTT TATAATCTGG   3420
ACAGGCCCGT GGTGGCTCTA AACGCACGAC AGTAGATCCT GAAGGTGGTG GACACATATA   3480
GAAAGTCGAT GGTCCGTTAG CCTCTATTTG GGACGCACGG AGAGCTTCCC TCATATCCGA   3540
CATATCGGTG GGATCTGTAG TTGGTTTTGG TGGTGTACCC CCTACCTCAG GGGTAGCTAC   3600
AGTCCGCCGG GGTTGTTCCG ATGTGCTTCC AGATTGACCC TCTACTGGAC GGGGACCGAC   3660
TAAGAATAGT ACGATCCAGA TAAATGAAAC ATATCTAGCT AGTCTGGTTA ATCCCGACGA   3720
TCCGTTACCA TGTCTGGAGC CAGTCGCTGC AATACCGAGT AGAGAAGGGA AAAAACATCT   3780
CTGTCGAAAA TAGCCACTGT GTCCCTGCCA ACGACTCCCT CGTCGCCGCT TCCCAAGATC   3840
```

-continued

```
GCCACGAGTG GACATTACGA TACAAACTTA ACGGATATCG CGATAATGAA ATAATTTATG   3900
ATTATTTCTC GCTTTCAATT TAACACAACC CTCAAGAACC TTTGTATTTA TTTTCACTTT   3960
TTAAGTATAG AATAAAGAAG CTCTAATTAA TTAAGCTACA AATAGTTTCG TTTTCACCTT   4020
GTCTAATAAC TAATTAATTA ACCCGGATCG ATCCCGATTT TTATGACTAG TTAATCAAAT   4080
AAAAAGCATA CAAGCTATTG CTTCGCTATC GTTACAAAAT GGCAGGAATT TTGTGTAAAC   4140
TAAGCCACAT ACTTGCCAAT GAAAAAAATA GTAGAAAGGA TACTATTTTA ATGGGATTAG   4200
ATGTTAAGGT TCCTTGGGAT TATAGTAACT GGGCATCTGT TAACTTTTAC GACGTTAGGT   4260
TAGATACTGA TGTTACAGAT TATAATAATG TTACAATAAA ATACATGACA GGATGTGATA   4320
TTTTTCCTCA TATAACTCTT GGAATAGCAA ATATGGATCA ATGTGATAGA TTTGAAAATT   4380
TCAAAAAGCA AATAACTGAT CAAGATTTAC AGACTATTTC TATAGTCTGT AAAGAAGAGA   4440
TGTGTTTTCC TCAGAGTAAC GCCTCTAAAC AGTTGGGAGC GAAAGGATGC GCTGTAGTTA   4500
TGAAACTGGA GGTATCTGAT GAACTTAGAG CCCTAAGAAA TGTTCTGCTG AATGCGGTAC   4560
CCTGTTCGAA GGACGTGTTT GGTGATATCA CAGTAGATAA TCCGTGGAAT CCTCACATAA   4620
CAGTAGGATA TGTTAAGGAG GACGATGTCG AAAACAAGAA ACGCCTAATG GAGTGCATGT   4680
CCAAGTTTAG GGGGCAAGAA ATACAAGTTC TAGGATGGTA TTAATAAGTA TCTAAGTATT   4740
TGGTATAATT TATTAAATAG TATAATTATA ACAAATAATA AATAACATGA TAACGGTTTT   4800
TATTAGAATA AAATAGAGAT AATATCATAA TGATATATAA TACTTCATTA CCAGAAATGA   4860
GTAATGGAAG ACTTATAAAT GAACTGCATA AAGCTATAAG GTATAGAGAT ATAAATTTAG   4920
TAAGGTATAT ACTTAAAAAA TGCAAATACA ATAACGTAAA TATACTATCA ACGTCTTTGT   4980
ATTTAGCCGT AAGTATTTCT GATATAGAAA TGGTAAAATT ATTACTAGAA CACGGTGCCG   5040
ATATTTTAAA ATGTAAAAAT CCTCCTCTTC ATAAAGCTGC TAGTTTAGAT AATACAGAAA   5100
TTGCTAAACT ACTAATAGAT TCTGGCGCTG ACATAGAACA GATACATTCT GGAAATAGTC   5160
CGTTATATAT TTCTGTATAT AGAAACAATA AGTCATTAAC TAGATATTTA TTAAAAAAAG   5220
GTGTTAATTG TAATAGATTC TTTCTAAATT ATTACGATGT ACTGTATGAT AAGATATCTG   5280
ATGATATGTA TAAAATATTT ATAGATTTTA ATATTGATCT TAATATACAA ACTAGAAATT   5340
TTGAAACTCC GTTACATTAC GCTATAAAGT ATAAGAATAT AGATTTAATT AGGATATTGT   5400
TAGATAATAG TATTAAAATA GATAAAAGTT TATTTTTGCA TAAACAGTAT CTCATAAAGG   5460
CACTTAAAAA TAATTGTAGT TACGATATAA TAGCGTTACT TATAAATCAC GGAGTGCCTA   5520
TAAACGAACA AGATGATTTA GGTAAAACCC CATTACATCA TTCGGTAATT AATAGAAGAA   5580
AAGATGTAAC AGCACTTCTG TTAAATCTAG GAGCTGATAT AAACGTAATA GATGACTGTA   5640
TGGGCAGTCC CTTACATTAC GCTGTTTCAC GTAACGATAT CGAAACAACA AAGACACTTT   5700
TAGAAAGAGG ATCTAATGTT AATGTGGTTA ATAATCATAT AGATACCGTT CTAAATATAG   5760
CTGTTGCATC TAAAAACAAA ACTATAGTAA ACTTATTACT GAAGTACGGT ACTGATACAA   5820
AGTTGGTAGG ATTAGATAAA CATGTTATTC ACATAGCTAT AGAAATGAAA GATATTAATA   5880
TACTGAATGC GATCTTATTA TATGGTTGCT ATGTAAACGT CTATAATCAT AAAGGTTTCA   5940
CTCCTCTATA CATGGCAGTT AGTTCTATGA AAACAGAATT TGTTAAACTC TTACTTGACC   6000
ACGGTGCTTA CGTAAATGCT AAAGCTAAGT TATCTGGAAA TACTCCTTTA CATAAAGCTA   6060
TGTTATCTAA TAGTTTTAAT AATATAAAAT TACTTTTATC TTATAACGCC GACTATAATT   6120
CTCTAAATAA TCACGGTAAT ACGCCTCTAA CTTGTGTTAG CTTTTTAGAT GACAAGATAG   6180
CTATTATGAT AATATCTAAA ATGATGTTAG AAATATCTAA AAATCCTGAA ATAGCTAATT   6240
```

-continued

CAGAAGGTTT TATAGTAAAC ATGGAACATA TAAACAGTAA TAAAAGACTA CTATCTATAA 6300

AAGAATCATG CGAAAAAGAA CTAGATGTTA TAACACATAT AAAGTTAAAT TCTATATATT 6360

CTTTTAATAT CTTTCTTGAC AATAACATAG ATCTTATGGT AAAGTTCGTA ACTAATCCTA 6420

GAGTTAATAA GATACCTGCA TGTATACGTA TATATAGGGA ATTAATACGG AAAAATAAAT 6480

CATTAGCTTT TCATAGACAT CAGCTAATAG TTAAAGCTGT AAAAGAGAGT AAGAATCTAG 6540

GAATAATAGG TAGGTTACCT ATAGATATCA AACATATAAT AATGGAACTA TTAAGTAATA 6600

ATGATTTACA TTCTGTTATC ACCAGCTGTT GTAACCCAGT AGTATAAAG 6649

(2) INFORMATION FOR SEQ ID NO:6:

(i) SEQUENCE CHARACTERISTICS:
(A) LENGTH: 10962 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

CCTTTTTTTT TCATTATTTA GAAATTATGC ATTTTAGATC TTTATAAGCG GCCGTGATTA 60

ACTAGTCATA AAAACCCGGG ATCGATTCTA GACTCGAGGG TACCGGATCT TAATAAAAAA 120

AGTAATAAAT CTTTAATACG TAAAATCTAG AAATATTCGC CGGCACTAAT TGATCAGTAT 180

TTTTGGGCCC TAGCTAAGAT CTGAGCTCCC ATGGCCTAGA ATTATAATTA GTCATCAGGC 240

AGGGCGAGAA CGAGACTATC TGCTCGTTAA TTAATTAGGT CGACGGATCC CCCAACAAAA 300

ACTAATCAGC TATCGGGGTT AATTAATTAG TTATATTAAT CAGTAGTCCG TCCCGCTCTT 360

GCTCTGATAG ACGAGCAATT AATTAATCCA GCTGCCTAGG GGGTTGTTTT TGATTAGTCG 420

ATAGCCCCAA TTAATTAATC AATATAGACA AGGTGAAAAC GAAACTATTT GTAGCTTAAT 480

TAATTAGAGC TTCTTTATTC TATACTTAAA AAGTGAAAAT AAATACAAAG GTTCTTGAGG 540

GTTGTGTTAA ATTGATCTGT TCCACTTTTG CTTTGATAAA CATCGAATTA ATTAATCTCG 600

AAGAAATAAG ATATGAATTT TTCACTTTTA TTTATGTTTC CAAGAACTCC CAACACAATT 660

TAACTAAAGC GAGAAATAAT CATAAATTAT TTCATTATCG CGATATCCGT TAAGTTTGTA 720

TCGTAATGCC ACTAACAGAA GAAGCAGAGC TAGAACTGGC AGAAAACTTT CGCTCTTTAT 780

TAGTATTTAA TAAAGTAATA GCGCTATAGG CAATTCAAAC ATAGCATTAC GGTGATTGTC 840

TTCTTCGTCT CGATCTTGAC CGTCTTTTGT TTGGAAGGAA GATAGAGAGA TTCTAAAAGA 900

ACCAGTACAT GGAGTGTATT ATGACCCATC AAAAGACTTA ATAGCAGAAA TACAGAAGCA 960

GGGGCAAGGC CAATCTCTCT AAGATTTTCT TGGTCATGTA CCTCACATAA TACTGGGTAG 1020

TTTTCTGAAT TATCGTCTTT ATGTCTTCGT CCCCGTTCCG GTTAGGGAGA TTAAAAGGGG 1080

GGGTTGGACA TATCAAATTT ATCAAGAGCC ATTTAAAAAT CTGAAAACAG GAATGGAGTG 1140

GAGATTTGAT TCTAGATTAG CATTTCATCA CGTAACCTGT ATAGTTTAAA TAGTTCTCGG 1200

TAAATTTTTA GACTTTTGTC CTTACCTCAC CTCTAAACTA AGATCTAATC GTAAAGTAGT 1260

GCATTTTGTG GATGTGTAGA AGAAATGCTA GAGAATTACA TCCTGAATAT TTTAAAAATT 1320

GTAAGCTTAT GGCAATATTC CAAAGTAGCA TGACAAAAAT CTTAGAGCCT TTTAGACGAT 1380

CTCTTAATGT AGGACTTATA AAATTTTTAA CATTCGAATA CCGTTATAAG GTTTCATCGT 1440

ACTGTTTTTA GAATCTCGGA AAATCTAAAG GGTACTAAGT TGAGTAAACA AAATCCAGAC 1500

ATAGTTATCT ATCAATACAT GGATGATTTG TATGTAGGAT CTGACTTAGA AATAGGGCAG 1560

CATAGAACAA AAATATTTGT TTTAGGTCTG TATCAATAGA TAGTTATGTA CCTACTAAAC 1620

-continued

```
ATACATCCTA GACTGAATCT TTATCCCGTC GTATCTTGTT TTTATGAAAT GTTAATAGAG   1680
GGAGTTGAGG AGCTGAGACA ACATCTGTTG AGGTGGGGAC TTACAACCAT GGTAGGTTTT   1740
CCAGTAACAC CTCAAGTACC TTTAAGACCA ATGACTCTCC TCGACTCTGT TGTAGACAAC   1800
TCCACCCCTG AATGTTGGTA CCATCCAAAA GGTCATTGTG GAGTTCATGG AAATTCTGGT   1860
TACTGAGGAG GAGTGTTTAG ATGAAGTTTT ACAAAGCAGC TGTAGATCTT TCTCACTTTT   1920
TAAAAGAAAA AGGAGGTTTA GAAGGGCTAA TTCATTCTCA ACGAAGACAA GATATTCTTA   1980
TGTTTCGTCG ACATCTAGAA AGAGTGAAAA ATTTTCTTTT TCCTCCAAAT CTTCCCGATT   2040
AAGTAAGAGT TGCTTCTGTT CTATAAGAAT AAAAAAGGGG GGAGAGGATG ATTTGTGGAT   2100
TTATCATACA CAAGGATATT TTCCTGATTG GCAGAATTAC ACACCAGGAC CAGGAGTCAG   2160
ATACCCATTA ACCTTTGGTC TAAACACCTA AATAGTATGT GTTCCTATAA AAGGACTAAC   2220
CGTCTTAATG TGTGGTCCTG GTCCTCAGTC TATGGGTAAT TGGAAACCAA TTTGGTATGA   2280
TTGGAAGTTG TTGGTGCTAC AAGCTAGTAC CAATGATTGA GACTGTACCA GTAAAATTAA   2340
AGCCAGGAAT GGATGGCCCA AAAGTTAAAC AATGGCCATT GACCACGATG TTCGATCATG   2400
GTTACTAACT CTGACATGGT CATTTTAATT TCGGTCCTTA CCTACCGGGT TTTCAATTTG   2460
TTACCGGTAA CTCTATGTAA GTAGAGTTAC AGAAGAAAAA ATAAAAGCAT TAGTAGAAAT   2520
TTGTACAGAG ATGGAAAAGG AAGGGAAAAT TTCAAAAATT GGGCCTTAAT TTTTCTTGTC   2580
TTCTTTTTTA TTTTCGTAAT CATCTTTAAA CATGTCTCTA CCTTTTCCTT CCCTTTTAAA   2640
GTTTTTAACC CGGAATTAAA AAGATGGAAA GCTGTGGGGT GCAGCCCGGG GGATCCTTTT   2700
TATAGCTAAT TAGTCACGTA CCTTTGAGAG TACCACTTCA GCTACCTCTT TTGTGTCTCA   2760
GAGTAACTTT CTTTAATCAA TTCCAAAACA CGTCGGGCCC CCTAGGAAAA ATATCGATTA   2820
ATCAGTGCAT GGAAACTCTC ATGGTGAAGT CGATGGAGAA AACACAGAGT CTCATTGAAA   2880
GAAATTAGTT AAGGTTTTGT GAGAGTAAAT TACTAGCAGA AGCTAAGAGC GGAGCACCAT   2940
AGACCATAGG AGGAGCAGAT AATGTAGTAT ACTAATATTA ACTCACATTT GACTAATTAG   3000
CTATAAAAAC CCGGGATCGA TTCTAGAATA AAAATTATCC CTGCCTAACT CTATTCACTA   3060
CAGAGAGTAC AGCAAAAACA TTACATCATA TGATTATAAT TGAGTGTAAA CTGATTAATC   3120
GATATTTTTG GGCCCTAGCT AAGATCTTAT TTTTAATAGG GACGGATTGA GATAAGTGAT   3180
GTCTCTCATG TCGTTTTTGC AGAGATAAGT ATTCTTAAAC CTACCAAGCC TCCTACTATC   3240
ATTATGAATA ATCTTTTTTC TCTCTGCACC ACTCTTCTCT TTGCCTTGGT GGGTGCTACT   3300
CCTAATGGTT CAATTGTTAC TACTTTATAA TAAGAATTTG GATGGTTCGG AGGATGATAG   3360
TAATACTTAT TAGAAAAAAG AGAGACGTGG TGAGAAGAGA AACGGAACCA CCCACGATGA   3420
GGATTACCAA GTTAACAATG ATGAAATATG GGATAGTTAA GGGTTTATAT AATTCACTTC   3480
TCCAATTGTC CCTCATATCT CCTCCTCCAG GTCTGAAGAT CTCGGTGTCG TTCGTGTCCG   3540
TGTCCTTACC ACCATCTCTT GTTAATAGTA GCCCTGTAAT ATTAAATATA TTAAGTGAAG   3600
AGGTTAACAG GGAGTATAGA GGAGGAGGTC CAGACTTCTA GAGCCACAGC AAGCACAGGC   3660
ACAGGAATGG TGGTAGAGAA CAATTATCAT CGGGACATTA TAAGGGTTTG GTGTGGTGAT   3720
GAACATCTAA TTTGTCCTTC AATGGGAGGG GCATATATTG CTTTTCCTAC TTCCTGCCAC   3780
ATGTTTATAA TTTGTTTTAT TTTGCATTGA AGTGTGATAT TGTTATTTGA CCCTGTACTA   3840
CTTGTAGATT AAACAGGAAG TTACCCTCCC CGTATATAAC GAAAAGGATG AAGGACGGTG   3900
TACAAATATT AAACAAAATA AAACGTAACT TCACACTATA ACAATAAACT GGGACACGAA   3960
GCTGTGGAGT ATTATTCCAA GTATTATTAC CATTCCAAGT ACTATTAAAC AGTGGTGATG   4020
```

-continued

```
AATTACAGTA GAAGAATTCC CCTCCACAAT TAAAACTGTG CATTACAATT TCTGGGTCCC   4080
CTCCTGATCA TAATAAGGTT CATAATAATG GTAAGGTTCA TGATAATTTG TCACCACTAC   4140
TTAATGTCAT CTTCTTAAGG GGAGGTGTTA ATTTTGACAC GTAATGTTAA AGACCCAGGG   4200
GAGGACTTTG TCGGCGGGGG GATTGATTAA AGACTATTGT TTTATTCTTA AATTGTTCTT   4260
TTAATTTGCT AACTATCTGT CTTAAAGTGT CATTCCATTT TGCTCTACTA ATGTTACAAT   4320
GTGCTTGTCT TATAGTTCCC CTAACTAATT TCTGATAACA AAATAAGAAT TTAACAAGAA   4380
AATTAAACGA TTGATAGACA GAATTTCACA GTAAGGTAAA ACGAGATGAT TACAATGTTA   4440
CACGAACAGA ATATCAAGGT TACATGGGTA TTATATTTTT TGTTGTATAA AATGCTCTCC   4500
CTGGTCCTAT ATGTATCCTT TTTCTTTTAT TGTAGTTGGG TCTTGTACAA TTAATTTGTA   4560
CAGATTCATT CAGATGTACT ATGATGGTAT AATATAAAAA ACAACATATT TTACGAGAGG   4620
GACCAGGATA TACATAGGAA AAAGAAAATA ACATCAACCC AGAACATGTT AATTAAACAT   4680
GTCTAAGTAA GTCTACATGA TACTACCATT AGGTCTGGTT TAGCATTATC ATTGAAATTC   4740
TCAGATCTAA TTACTACCTC TTCTTCTGCT AGACTGCCAT TTAACAGCAG TTGAGTTGAT   4800
ACTACTGGCC TAATTCCATG TGTACATTGT ACTGTGCTAA ATCGTAATAG TAACTTTAAG   4860
AGTCTAGATT AATGATGGAG AAGAAGACGA TCTGACGGTA AATTGTCGTC AACTCAACTA   4920
TGATGACCGG ATTAAGGTAC ACATGTAACA TGACACGAAA GTGTCTGGGA CATTTTTACA   4980
TGATCCTTTT CCACTGAACT TTTTATCGTT ACACTTTAGA ATCGCAAAAC CAGCCGGGGC   5040
ACAATAGTGT ATGGGAATTG GCTCAAAGGA TATCTTTGGA CAAGCTTGCT GTAAAAATGT   5100
ACTAGGAAAA GGTGACTTGA AAAATAGCAA TGTGAAATCT TAGCGTTTTG GTCGGCCCCG   5160
TGTTATCACA TACCCTTAAC CGAGTTTCCT ATAGAAACCT GTTCGAACCG GCAGAACCAG   5220
GTGTAATGAC TGAGGTATTA CAACTTATCA ACCTATAGCT GGTACTATCA TTATTTATTG   5280
ATACTATATC AAGTTTATAA AGAAGTGCAT ATTCTTTCTG CATCTTATCT CTTATGCTTG   5340
TACATTACTG ACTCCATAAT GTTGAATAGT TGGATATCGA CCATGATAGT AATAAATAAC   5400
TATGATATAG TTCAAATATT TCTTCACGTA TAAGAAAGAC GTAGAATAGA GAATACGAAC   5460
ATTCTATGGG GTGATATTGA AAGAGCAGTT TTTCATTTCT CCTCCCTTTA TTGTTCCCTC   5520
GCTATTACTA TTGTTATTAG CAGTACTATT ATTGGTATTA GTAGTATTCC TCAAATCAGT   5580
GCAATTTAAC CACTATAACT TTCTCGTCAA AAAGTAAAGA GGAGGGAAAT AACAAGGGAG   5640
CGATAATGAT AACAATAATC GTCATGATAA TAACCATAAT CATCATAAGG AGTTTAGTCA   5700
CGTTAAATTT CGGTGATTTT TCGGAGTAAC ACAGAGTGGG GTTAATTTTA CACATGGCTT   5760
TAGGCTTTGA TCCCATAAAC TGATTATATC CTCATGCATC TGTTCTACCA TGTTATTTTT   5820
CCACATGTTA AAATTTTCTG TCACTCATTG TGTCTCACCC CAATTAAAAT GTGTACCGAA   5880
ATCCGAAACT AGGGTATTTG ACTAATATAG GAGTACGTAG ACAAGATGGT ACAATAAAAA   5940
GGTGTACAAT TTTAAAAGAC AGTGTCTCTG GATTTACCAA TTCTACTTCT TGTGGGTTGG   6000
GGTCTGTGGG TACACAGGCA TGTGTGGCCC AAACATTATG TACCTCTGTA TCATATGCTT   6060
TAGCATCTGA TGCACAAAAT AGAGTGGTGG TTAAATGGTT AAGATGAAGA ACACCCAACC   6120
CCAGACACCC ATGTGTCCGT ACACACCGGG TTTGTAATAC ATGGAGACAT AGTATACGAA   6180
ATCGTAGACT ACGTGTTTTA TCTCACCACC ATCATATAAA CTTTGGTGCT TCTTTCCACA   6240
CAGGTACCCC ATAATAGACT GTGACCCACA ATTTTTCTGT AGCACTACAG ATCATCAACA   6300
TCCCAAGGAG CATGGTGCCC CATCTCCACC CCCATCTCCA CAAGTGACGA AGAAAGGTGT   6360
GTCCATGGGG TATTATCTGA CACTGGGTGT TAAAAAGACA TCGTGATGTC TAGTAGTTGT   6420
```

-continued

```
AGGGTTCCTC GTACCACGGG GTAGAGGTGG GGGTAGAGGT GTTCACAGTT ACGTGGGGCT   6480
GATATTTCTC CTTCACTCTC ATTGCCACTG TCTTCTGCTC TTTCATATAC GATACAAACT   6540
TAACGCATAT CGCGATAATG AAATAATTTA TGATTATTTC TCGCTTTCAA TTTAACACGA   6600
CTATAAAGAG GAAGTGAGAG TAACGGTGAC AGAAGACGAG AAAGTATATG CTATGTTTGA   6660
ATTGCGTATA GCGCTATTAC TTTATTAAAT ACTAATAAAG AGCGAAAGTT AAATTGTGAT   6720
GGACCATAAC CCTCAAGAAC CTTTGTATTT ATTTTCACTT TTTAAGTATA GAATAAAGAA   6780
GCTCTAATTA ATTAAGCTAC AAATAGTTTC GTTTTCACCT TGTCTAATAA CTAATTAATT   6840
AACCCGGTTG GGAGTTCTTG GAAACATAAA TAAAAGTGAA AAATTCATAT CTTATTTCTT   6900
CGAGATTAAT TAATTCGATG TTTATCAAAG CAAAAGTGGA ACAGATTATT GATTAATTAA   6960
TTGGGCCACC ATATCTTGAG ATAAAGTGAA AATATATATC ATTATATTAC AAAGTACAAT   7020
TATTTAGGTT TAATCATGGG TGCGAGAGCG TCAGTATTAA GCGGGGGAGA ATTAGATCGA   7080
TGGGAAAAAA TTTAGAACTC TATTTCACTT TTATATATAG TAATATAATG TTTCATGTTA   7140
ATAAATCCAA ATTAGTACCC ACGCTCTCGC AGTCATAATT CGCCCCCTCT TAATCTAGCT   7200
ACCCTTTTTT AAACCATGAA GGGAGGCGGT TAAGGCCAGG GGGAAAGAAA AAATATAAAT   7260
TAAAACATAT AGTATGGGCA AGCAGGGAGC TAGAACGATT CGCAGTTAAT CCTGGCCTGT   7320
TAGAAACATC AGAAGGCTGT AGACAAGCCA ATTCCGGTCC CCCTTTCTTT TTTATATTTA   7380
ATTTTGTATA TCATACCCGT TCGTCCCTCG ATCTTGCTAA GCGTCAATTA GGACCGGACA   7440
ATCTTTGTAG TCTTCCGACA TCTGTTGGAA GTGCGAGGAT ACTGGGACAG CTACAACCAT   7500
CCCTTCAGAC AGGATCAGAA GAACTTAGAT CATTATATAA TACAGTAGCA ACCCTCTATT   7560
GTGTGCATCA AAGGATAGAG ATAAAAGACA CCAAGGAATA TGACCCTGTC GATGTTGGTA   7620
GGGAAGTCTG TCCTAGTCTT CTTGAATCTA GTAATATATT ATGTCATCGT TGGGAGATAA   7680
CACACGTAGT TTCCTATCTC TATTTTCTGT GGTTCCTTGT GTATCTGAGG GCTTTAGACA   7740
AGATAGAGGA AGAGCAAAAC AAAAGTAAGA AAAAAGCACA GCAAGCAGCA GCTGACACAG   7800
GACACAGCAA TCAGGTCAGC CAAAATTACC CTATAGTGCA GAACATCCAG CGAAATCTGT   7860
TCTATCTCCT TCTCGTTTTG TTTTCATTCT TTTTTCGTGT CGTTCGTCGT CGACTGTGTC   7920
CTGTGTCGTT AGTCCAGTCG GTTTTAATGG GATATCACGT CTTGTAGGTC AAAAATGGAG   7980
GGGGCAAATG GTACATCAGG CCATATCACC TAGAACTTTA AATGCATGGG TAAAAGTAGT   8040
AGAAGAGAAG GCTTTCAGCC CAGAAGTGAT ACCCATGTTT TCAGCATTAT CAGAAGGAGC   8100
CCCCGTTTAC CATGTAGTCC GGTATAGTGG ATCTTGAAAT TTACGTACCC ATTTTCATCA   8160
TCTTCTCTTC CGAAAGTCGG GTCTTCACTA TGGGTACAAA AGTCGTAATA GTCTTCCTCG   8220
GGATAAAGAG AGGACCCCAC AAGATTTAAA CACCATGCTA AACACAGTGG GGGGACATCA   8280
AGCAGCCATG CAAATGTTAA AAGAGACCAT CAATGAGGAA GCTGCAGAAT GGGATAGAGT   8340
GCATCCAGTG CATTGGGGTG TTCTAAATTT GTGGTACGAT TTGTGTCACC CCCCTGTAGT   8400
TCGTCGGTAC GTTTACAATT TTCTCTGGTA GTTACTCCTT CGACGTCTTA CCCTATCTCA   8460
CGTAGGTCAC GTATTTGGAA TAAGAGGGCA GGGCCTATTG CACCAGGCCA GATGAGAGAA   8520
CCAAGGGGAA GTGACATAGC AGGAACTACT AGTACCCTTC AGGAACAAAT AGGATGGATG   8580
ACAAATAATC CACCTATCCC AGTAGGACGT CCCGGATAAC GTGGTCCGGT CTACTCTCTT   8640
GGTTCCCCTT CACTGTATCG TCCTTGATGA TCATGGGAAG TCCTTGTTTA TCCTACCTAC   8700
TGTTTATTAG GTGGATAGGG TCATCCTAGA GGAGTTTGTG GAGGGAAATT TATAAAAGAT   8760
GGATAATCCT GGGATTAAAT AAAATAGTAA GAATGTATAG CCCTACCAGC ATTCTGGACA   8820
```

-continued

```
TAAGACAAGG ACCAAAAGAA CCCTTTAGAG ACTATGTAGA CCGGCTTTAA ATATTTTCTA   8880
CCTATTAGGA CCCTAATTTA TTTTATCATT CTTACATATC GGGATGGTCG TAAGACCTGT   8940
ATTCTGTTCC TGGTTTTCTT GGGAAATCTC TGATACATCT GGCCGTGGAG GTTCTATAAA   9000
ACTCTAAGAG CCGAGCAAGC TTCACAGGAG GTAAAAAATT GGATGACAGA AACCTTGTTG   9060
GTCCAAAATG CGAACCCAGA TTGTAAGACT ATTTTAAAAG CATTGGGACC AAAGATATTT   9120
TGAGATTCTC GGCTCGTTCG AAGTGTCCTC CATTTTTTAA CCTACTGTCT TTGGAACAAC   9180
CAGGTTTTAC GCTTGGGTCT AACATTCTGA TAAAATTTTC GTAACCCTGG TTAATTACTA   9240
GGAGGGCGGC TACACTAGAA GAAATGATGA CAGCATGTCA GGGAGTAGGA GGACCCGGCC   9300
ATAAGGCAAG AGTTTTGGCT GAAGCAATGA GCCAAGTAAC AAATTCAGCT ACCATAATGA   9360
TGCAGCGCCG ATGTGATCTT CTTTACTACT GTCGTACAGT CCCTCATCCT CCTGGGCCGG   9420
TATTCCGTTC TCAAAACCGA CTTCGTTACT CGGTTCATTG TTTAAGTCGA TGGTATTACT   9480
ACGTCAATTA CGGGGAAATA TGAGGAGAGG CAATTTTAGG AACCAAAGAA AGATTGTTAA   9540
GTGTTTCAAT TGTGGCAAAG AAGGGCACAC AGCCAGAAAT TGCAGGGCCC CTAGGAAAAA   9600
GGGCTGTTGG AAATGTGGAA AGGAATCTCC GTTAAAATCC TTGGTTTCTT TCTAACAATT   9660
CACAAAGTTA ACACCGTTTC TTCCCGTGTG TCGGTCTTTA ACGTCCCGGG GATCCTTTTT   9720
CCCGACAACC TTTACACCTT TCCTTGCCGG TACAGCCGGA GGGGACACCA AATGAAAGAT   9780
TGTACTGAGA GACAGGCTAA TTTTTTAGGG AAGATCTGGC CTTCCTACAA GGGAAGGCCA   9840
GGGAATTTTC TTCAGAGCAG ACCAGAGCCA ACAGCCCCAC CACCTGTGGT TTACTTTCTA   9900
ACATGACTCT CTGTCCGATT AAAAAATCCC TTCTAGACCG GAAGGATGTT CCCTTCCGGT   9960
CCCTTAAAAG AAGTCTCGTC TGGTCTCGGT TGTCGGGGTG GTGCTAGGGT AGAGGGAAGA  10020
GAGCTTCAGG TCTGGGGTAG AGACAACAAC TCCCCCTCAG AAGCAGGAGC CGATAGACAA  10080
GGAACTGTAT CCTTTAACTT CCCTCAGATC ACTCTTTGGC AACGACCCCT CGTCACTTCT  10140
CTCGAAGTCC AGACCCCATC TCTGTTGTTG AGGGGGAGTC TTCGTCCTCG GCTATCTGTT  10200
CCTTGACATA GGAAATTGAA GGGAGTCTAG TGAGAAACCG TTGCTGGGGA GCAGTGTTTT  10260
GTGAGGCAAT AAAGATAGGG GGGCAACTAA AGGAAGCTCT ATTAGATACA GGAGCAGATG  10320
ATACAGTATT AGAAGAAATG AGTTTGCCAG GAAGATGGAA ACCAAAAATG ATAGGGGGAA  10380
TTGGAGGTTA TTTCTATCCC CCCGTTGATT TCCTTCGAGA TAATCTATGT CCTCGTCTAC  10440
TATGTCATAA TCTTCTTTAC TCAAACGGTC CTTCTACCTT TGGTTTTTAC TATCCCCCTT  10500
AACCTCTGGA TGATGGGGGA GGGTTTTATC AAAGTAAGAC AGTATGATCA GATACTCATA  10560
GAAATCTGTG GACATAAAGC TATAGGTACA GTATTAGTAG GACCTACACC TGTCAACATA  10620
ATTGGAAGAA ATCTGTTGAC TCCAAAATAG TTTCATTCTG TCATACTAGT CTATGAGTAT  10680
CTTTAGACAC CTGTATTTCG ATATCCATGT CATAATCATC CTGGATGTGG ACAGTTGTAT  10740
TAACCTTCTT TAGACAACTG AGGCGAGTGT GTGAGGAGAT TGGTTGCACT TTAAATTTTT  10800
AACCCGGGGG ATCCCGATTT TTATGACTAG TTAATCAAAT AAAAAGCATA CAAGCTATTG  10860
CTTCTCTAAC CAACGTGAAA TTTAAAAATT GGGCCCCCTA GGGCTAAAAA TACTGATCAA  10920
TTAGTTTATT TTTCGTATGT TCGATAACGA AGGCTCAGAG AG                     10962
```

(2) INFORMATION FOR SEQ ID NO:7:

(i) SEQUENCE CHARACTERISTICS:
(A) LENGTH: 7797 base pairs
(B) TYPE: nucleic acid
(C) STRANDEDNESS: single -continued (D) TOPOLOGY: linear (ii) MOLECULE TYPE: DNA (genomic)

(xi) SEQUENCE DESCRIPTION: SEQ ID NO:7:

GAGAGTAAAT TACTAGCAGA AGCTAAGAGC GGAGCACCAT AGACCATAGG AGGAGCAGAT 60

AATGTAGTAT ACTAATATTA ACTCACATTT GACTAATTAG CTATAAAAAC CCGGGATCGA 120

TTCTAGAATA AAAATTATCC CTGCCTAACT CTATTCACTA CAGAGAGTAC AGCAAAAACA 180

TTACATCATA TGATTATAAT TGAGTGTAAA CTGATTAATC GATATTTTTG GGCCCTAGCT 240

AAGATCTTAT TTTTAATAGG GACGGATTGA GATAAGTGAT GTCTCTCATG TCGTTTTTGC 300

AGATAAGTAT TCTTAAACCT ACCAAGCCTC CTACTATCAT TATGAATAAT CTTTTTTCTC 360

TCTGCACCAC TCTTCTCTTT GCCTTGGTGG GTGCTACTCC TAATGGTTCA ATTGTTACTA 420

CTTTATAATA AGAATTTGGA TGGTTCGGAG GATGATAGTA ATACTTATTA GAAAAAAGAG 480

AGACGTGGTG AGAAGAGAAA CGGAACCACC CACGATGAGG ATTACCAAGT TAACAATGAT 540

GAAATATTAA GGGTTTATAT AATTCACTTC TCCAATTGTC CCTCATATCT CCTCCTCCAG 600

GTCTGAAGAT CTCGGTGTCG TTCGTGTCCG TGTCCTTACC ACCATCTCTT GTTAATAGTA 660

GCCCTGTAAT ATTAAATATA TTAAGTGAAG AGGTTAACAG GGAGTATAGA GGAGGAGGTC 720

CAGACTTCTA GAGCCACAGC AAGCACAGGC ACAGGAATGG TGGTAGAGAA CAATTATCAT 780

CGGGACATTA TAAGGTGATG AACATCTAAT TTGTCCTTCA ATGGGAGGGG CATATATTGC 840

TTTTCCTACT TCCTGCCACA TGTTTATAAT TTGTTTTATT TTGCATTGAA GTGTGATATT 900

GTTATTTGAC CCTGTACTAC TTGTAGATTA AACAGGAAGT TACCCTCCCC GTATATAACG 960

AAAAGGATGA AGGACGGTGT ACAAATATTA AACAAAATAA AACGTAACTT CACACTATAA 1020

CAATAAACTG GGACAGGAGT ATTATTCCAA GTATTATTAC CATTCCAAGT ACTATTAAAC 1080

AGTGGTGATG AATTACAGTA GAAGAATTCC CCTCCACAAT TAAAACTGTG CATTACAATT 1140

TCTGGGTCCC CTCCTGATCA TAATAAGGTT CATAATAATG GTAAGGTTCA TGATAATTTG 1200

TCACCACTAC TTAATGTCAT CTTCTTAAGG GGAGGTGTTA ATTTTGACAC GTAATGTTAA 1260

AGACCCAGGG GAGGACTGGG GATTGATTAA AGACTATTGT TTTATTCTTA AATTGTTCTT 1320

TTAATTTGCT AACTATCTGT CTTAAAGTGT CATTCCATTT TGCTCTACTA ATGTTACAAT 1380

GTGCTTGTCT TATAGTTCCC CTAACTAATT TCTGATAACA AAATAAGAAT TTAACAAGAA 1440

AATTAAACGA TTGATAGACA GAATTTCACA GTAAGGTAAA ACGAGATGAT TACAATGTTA 1500

CACGAACAGA ATATCAAGGG GTATTATATT TTTTGTTGTA TAAAATGCTC TCCCTGGTCC 1560

TATATGTATC CTTTTTCTTT TATTGTAGTT GGGTCTTGTA CAATTAATTT GTACAGATTC 1620

ATTCAGATGT ACTATGATGG TATAATATAA AAAACAACAT ATTTTACGAG AGGGACCAGG 1680

ATATACATAG GAAAAAGAAA ATAACATCAA CCCAGAACAT GTTAATTAAA CATGTCTAAG 1740

TAAGTCTACA TGATACTACC AGGTTTAGCA TTATCATTGA AATTCTCAGA TCTAATTACT 1800

ACCTCTTCTT CTGCTAGACT GCCATTTAAC AGCAGTTGAG TTGATACTAC TGGCCTAATT 1860

CCATGTGTAC ATTGTACTGT GCTAAATCGT AATAGTAACT TTAAGAGTCT AGATTAATGA 1920

TGGAGAAGAA GACGATCTGA CGGTAAATTG TCGTCAACTC AACTATGATG ACCGGATTAA 1980

GGTACACATG TAACATGACA CGAGGGACAT TTTTACATGA TCCTTTTCCA CTGAACTTTT 2040

TATCGTTACA CTTTAGAATC GCAAAACCAG CCGGGGCACA ATAGTGTATG GGAATTGGCT 2100

CAAAGGATAT CTTTGGACAA GCTTGCTGTA AAAATGTACT AGGAAAAGGT GACTTGAAAA 2160

ATAGCAATGT GAAATCTTAG CGTTTTGGTC GGCCCCGTGT TATCACATAC CCTTAACCGA 2220

-continued

```
GTTTCCTATA GAAACCTGTT CGAACGGTGT AATGACTGAG GTATTACAAC TTATCAACCT   2280
ATAGCTGGTA CTATCATTAT TTATTGATAC TATATCAAGT TTATAAAGAA GTGCATATTC   2340
TTTCTGCATC TTATCTCTTA TGCTTGTACA TTACTGACTC CATAATGTTG AATAGTTGGA   2400
TATCGACCAT GATAGTAATA AATAACTATG ATATAGTTCA AATATTTCTT CACGTATAAG   2460
AAAGACGTAG AATAGAGAAT ACGAACAGGG GTGATATTGA AAGAGCAGTT TTTCATTTCT   2520
CCTCCCTTTA TTGTTCCCTC GCTATTACTA TTGTTATTAG CAGTACTATT ATTGGTATTA   2580
GTAGTATTCC TCAAATCAGT GCAATTTAAC CACTATAACT TTCTCGTCAA AAAGTAAAGA   2640
GGAGGGAAAT AACAAGGGAG CGATAATGAT AACAATAATC GTCATGATAA TAACCATAAT   2700
CATCATAAGG AGTTTAGTCA CGTTAAATTG GAGTAACACA GAGTGGGGTT AATTTTACAC   2760
ATGGCTTTAG GCTTTGATCC CATAAACTGA TTATATCCTC ATGCATCTGT TCTACCATGT   2820
TATTTTTCCA CATGTTAAAA TTTTCTGTCA CTCATTGTGT CTCACCCCAA TTAAAATGTG   2880
TACCGAAATC CGAAACTAGG GTATTTGACT AATATAGGAG TACGTAGACA AGATGGTACA   2940
ATAAAAAGGT GTACAATTTT AAAAGACAGT GGGATTTACC AATTCTACTT CTTGTGGGTT   3000
GGGGTCTGTG GGTACACAGG CATGTGTGGC CCAAACATTA TGTACCTCTG TATCATATGC   3060
TTTAGCATCT GATGCACAAA ATAGAGTGGT GGTTAAATGG TTAAGATGAA GAACACCCAA   3120
CCCCAGACAC CCATGTGTCC GTACACACCG GGTTTGTAAT ACATGGAGAC ATAGTATACG   3180
AAATCGTAGA CTACGTGTTT TATCTCACCA CCAGGTGCTT CTTTCCACAC AGGTACCCCA   3240
TAATAGACTG TGACCCACAA TTTTTCTGTA GCACTACAGA TCATCAACAT CCCAAGGAGC   3300
ATGGTGCCCC ATCTCCACCC CCATCTCCAC AAGTGACGAA GAAAGGTGTG TCCATGGGGT   3360
ATTATCTGAC ACTGGGTGTT AAAAAGACAT CGTGATGTCT AGTAGTTGTA GGGTTCCTCG   3420
TACCACGGGG TAGAGGTGGG GGTAGAGGTG TTCACGGCTG ATATTTCTCC TTCACTCTCA   3480
TTGCCACTGT CTTCTGCTCT TTCATATACG ATACAAACTT AACGCATATC GCGATAATGA   3540
AATAATTTAT GATTATTTCT CGCTTTCAAT TTAACACGAC TATAAAGAGG AAGTGAGAGT   3600
AACGGTGACA GAAGACGAGA AAGTATATGC TATGTTTGAA TTGCGTATAG CGCTATTACT   3660
TTATTAAATA CTAATAAAGA GCGAAAGTTA AATTGTGGGA CCATAACCCT CAAGAACCTT   3720
TGTATTTATT TTCACTTTTT AAGTATAGAA TAAAGAAGCT CTAATTAATT AAGCTACAAA   3780
TAGTTTCGTT TTCACCTTGT CTAATAACTA ATTAATTAAC CCGGTTGGGA GTTCTTGGAA   3840
ACATAAATAA AAGTGAAAAA TTCATATCTT ATTTCTTCGA GATTAATTAA TTCGATGTTT   3900
ATCAAAGCAA AAGTGGAACA GATTATTGAT TAATTAATTG GGCCACCATA TCTTGAGATA   3960
AAGTGAAAAT ATATATCATT ATATTACAAA GTACAATTAT TTAGGTTTAA TCATGGGTGC   4020
GAGAGCGTCA GTATTAAGCG GGGGAGAATT AGATCGATGG GAAAAAATTT AGAACTCTAT   4080
TTCACTTTTA TATATAGTAA TATAATGTTT CATGTTAATA AATCCAAATT AGTACCCACG   4140
CTCTCGCAGT CATAATTCGC CCCCTCTTAA TCTAGCTACC CTTTTTTAAA CCATGAGGCG   4200
GTTAAGGCCA GGGGGAAAGA AAAAATATAA ATTAAAACAT ATAGTATGGG CAAGCAGGGA   4260
GCTAGAACGA TTCGCAGTTA ATCCTGGCCT GTTAGAAACA TCAGAAGGCT GTAGACAAGC   4320
CAATTCCGGT CCCCCTTTCT TTTTTATATT TAATTTTGTA TATCATACCC GTTCGTCCCT   4380
CGATCTTGCT AAGCGTCAAT TAGGACCGGA CAATCTTTGT AGTCTTCCGA CATCTGTTGA   4440
GGATACTGGG ACAGCTACAA CCATCCCTTC AGACAGGATC AGAAGAACTT AGATCATTAT   4500
ATAATACAGT AGCAACCCTC TATTGTGTGC ATCAAAGGAT AGAGATAAAA GACACCAAGG   4560
AATATGACCC TGTCGATGTT GGTAGGGAAG TCTGTCCTAG TCTTCTTGAA TCTAGTAATA   4620
```

-continued

```
TATTATGTCA TCGTTGGGAG ATAACACACG TAGTTTCCTA TCTCTATTTT CTGTGGTTCC   4680
TTGAGGGCTT TAGACAAGAT AGAGGAAGAG CAAAACAAAA GTAAGAAAAA AGCACAGCAA   4740
GCAGCAGCTG ACACAGGACA CAGCAATCAG GTCAGCCAAA ATTACCCTAT AGTGCAGAAC   4800
ATCCAGCGAA ATCTGTTCTA TCTCCTTCTC GTTTTGTTTT CATTCTTTTT TCGTGTCGTT   4860
CGTCGTCGAC TGTGTCCTGT GTCGTTAGTC CAGTCGGTTT TAATGGGATA TCACGTCTTG   4920
TAGGTCGAGG GGGCAAATGG TACATCAGGC CATATCACCT AGAACTTTAA ATGCATGGGT   4980
AAAAGTAGTA GAAGAGAAGG CTTTCAGCCC AGAAGTGATA CCCATGTTTT CAGCATTATC   5040
AGAAGGAGCC CCCGTTTACC ATGTAGTCCG GTATAGTGGA TCTTGAAATT TACGTACCCA   5100
TTTTCATCAT CTTCTCTTCC GAAAGTCGGG TCTTCACTAT GGGTACAAAA GTCGTAATAG   5160
TCTTCCTCGG GAGGACCCCA CAAGATTTAA ACACCATGCT AAACACAGTG GGGGGACATC   5220
AAGCAGCCAT GCAAATGTTA AAAGAGACCA TCAATGAGGA AGCTGCAGAA TGGGATAGAG   5280
TGCATCCAGT GCATTGGGGT GTTCTAAATT TGTGGTACGA TTTGTGTCAC CCCCCTGTAG   5340
TTCGTCGGTA CGTTTACAAT TTTCTCTGGT AGTTACTCCT TCGACGTCTT ACCCTATCTC   5400
ACGTAGGTCA CGTAGAGGGC AGGGCCTATT GCACCAGGCC AGATGAGAGA ACCAAGGGGA   5460
AGTGACATAG CAGGAACTAC TAGTACCCTT CAGGAACAAA TAGGATGGAT GACAAATAAT   5520
CCACCTATCC CAGTAGGACG TCCCGGATAA CGTGGTCCGG TCTACTCTCT TGGTTCCCCT   5580
TCACTGTATC GTCCTTGATG ATCATGGGAA GTCCTTGTTT ATCCTACCTA CTGTTTATTA   5640
GGTGGATAGG GTCATCCTGA GGGAAATTTA TAAAAGATGG ATAATCCTGG GATTAAATAA   5700
AATAGTAAGA ATGTATAGCC CTACCAGCAT TCTGGACATA AGACAAGGAC CAAAAGAACC   5760
CTTTAGAGAC TATGTAGACC GGCTTTAAAT ATTTTCTACC TATTAGGACC CTAATTTATT   5820
TTATCATTCT TACATATCGG GATGGTCGTA AGACCTGTAT TCTGTTCCTG GTTTTCTTGG   5880
GAAATCTCTG ATACATCTGG CCGAGGTTCT ATAAAACTCT AAGAGCCGAG CAAGCTTCAC   5940
AGGAGGTAAA AAATTGGATG ACAGAAACCT TGTTGGTCCA AAATGCGAAC CCAGATTGTA   6000
AGACTATTTT AAAAGCATTG GGACCAAAGA TATTTTGAGA TTCTCGGCTC GTTCGAAGTG   6060
TCCTCCATTT TTTAACCTAC TGTCTTTGGA ACAACCAGGT TTTACGCTTG GGTCTAACAT   6120
TCTGATAAAA TTTTCGTAAC CCTGGTGAGG GCGGCTACAC TAGAAGAAAT GATGACAGCA   6180
TGTCAGGGAG TAGGAGGACC CGGCCATAAG GCAAGAGTTT TGGCTGAAGC AATGAGCCAA   6240
GTAACAAATT CAGCTACCAT AATGATGCAG CGCCGATGTG ATCTTCTTTA CTACTGTCGT   6300
ACAGTCCCTC ATCCTCCTGG GCCGGTATTC CGTTCTCAAA ACCGACTTCG TTACTCGGTT   6360
CATTGTTTAA GTCGATGGTA TTACTACGTC GAGGAGAGGC AATTTTAGGA ACCAAAGAAA   6420
GATTGTTAAG TGTTTCAATT GTGGCAAAGA AGGGCACACA GCCAGAAATT GCAGGGCCCC   6480
TAGGAAAAAG GGCTGTTGGA AATGTGGAAA GGAATCTCCG TTAAAATCCT TGGTTTCTTT   6540
CTAACAATTC ACAAAGTTAA CACCGTTTCT TCCCGTGTGT CGGTCTTTAA CGTCCCGGGG   6600
ATCCTTTTTC CCGACAACCT TTACACCTTT CCTTGAGGGG ACACCAAATG AAAGATTGTA   6660
CTGAGAGACA GGCTAATTTT TTAGGGAAGA TCTGGCCTTC CTACAAGGGA AGGCCAGGGA   6720
ATTTTCTTCA GAGCAGACCA GAGCCAACAG CCCCACCACC TGTGGTTTAC TTTCTAACAT   6780
GACTCTCTGT CCGATTAAAA AATCCCTTCT AGACCGGAAG GATGTTCCCT TCCGGTCCCT   6840
TAAAAGAAGT CTCGTCTGGT CTCGGTTGTC GGGGTGGTGA GGGAAGAGAG CTTCAGGTCT   6900
GGGGTAGAGA CAACAACTCC CCCTCAGAAG CAGGAGCCGA TAGACAAGGA ACTGTATCCT   6960
TTAACTTCCC TCAGATCACT CTTTGGCAAC GACCCCTCGT CACTTCTCTC GAAGTCCAGA   7020
```

-continued

```
CCCCATCTCT GTTGTTGAGG GGGAGTCTTC GTCCTCGGCT ATCTGTTCCT TGACATAGGA   7080

AATTGAAGGG AGTCTAGTGA GAAACCGTTG CTGGGGAGCA GTGAGGCAAT AAAGATAGGG   7140

GGGCAACTAA AGGAAGCTCT ATTAGATACA GGAGCAGATG ATACAGTATT AGAAGAAATG   7200

AGTTTGCCAG GAAGATGGAA ACCAAAAATG ATAGGGGGAA TTGGAGGTTA TTTCTATCCC   7260

CCCGTTGATT TCCTTCGAGA TAATCTATGT CCTCGTCTAC TATGTCATAA TCTTCTTTAC   7320

TCAAACGGTC CTTCTACCTT TGGTTTTTAC TATCCCCCTT AACCTCGAGG GTTTTATCAA   7380

AGTAAGACAG TATGATCAGA TACTCATAGA AATCTGTGGA CATAAAGCTA TAGGTACAGT   7440

ATTAGTAGGA CCTACACCTG TCAACATAAT TGGAAGAAAT CTGTTGACTC CAAAATAGTT   7500

TCATTCTGTC ATACTAGTCT ATGAGTATCT TTAGACACCT GTATTTCGAT ATCCATGTCA   7560

TAATCATCCT GGATGTGGAC AGTTGTATTA ACCTTCTTTA GACAACTGAG GAGGAGATTG   7620

GTTGCACTTT AAATTTTTAA CCCGGGGGAT CCCGATTTTT ATGACTAGTT AATCAAATAA   7680

AAAGCATACA AGCTATTGCT TCTCTAACCA ACGTGAAATT TAAAAATTGG GCCCCCTAGG   7740

GCTAAAAATA CTGATCAATT AGTTTATTTT TCGTATGTTC GATAACGAAG GAGCAGA      7797
```

(2) INFORMATION FOR SEQ ID NO:8:

(i) SEQUENCE CHARACTERISTICS:
(A) LENGTH: 19877 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
CGAGCTCGCG GCCGCCTATC AAAAGTCTTA ATGAGTTAGG TGTAGATAGT ATAGATATTA     60

CTACAAAGGT ATTCATATTT CCTATCAATT CTAAAGTAGA TGATATTAAT ACTCGAGCGC    120

CGGCGGATAG TTTTCAGAAT TACTCAATCC ACATCTATCA TATCTATAAT GATGTTTCCA    180

TAAGTATAAA GGATAGTTAA GATTTCATCT ACTATAATTA TACTCAAAGA TGATGATAGT    240

AGATAATAGA TACGCTCATA TAATGACTGC AAATTTGGAC GGTTCACATT TTAATCATCA    300

CGCGTTCATA AGTTTCAACT GCATAGATCA ATGAGTTTCT ACTACTATCA TCTATTATCT    360

ATGCGAGTAT ATTACTGACG TTTAAACCTG CCAAGTGTAA AATTAGTAGT GCGCAAGTAT    420

TCAAAGTTGA CGTATCTAGT TAATCTCACT AAAAAGATAG CCGATGTATT TGAGAGAGAT    480

TGGACATCTA ACTACGCTAA AGAAATTACA GTTATAAATA ATACATAATG GATTTTGTTA    540

TCATCAGTTA TTTAGAGTGA TTTTTCTATC GGCTACATAA ACTCTCTCTA ACCTGTAGAT    600

TGATGCGATT TCTTTAATGT CAATATTTAT TATGTATTAC CTAAAACAAT AGTAGTCAAT    660

AATTTAACAT AAGTACAATA AAAAGTATTA AATAAAAATA CTTACTTACG AAAAAATGAC    720

TAATTAGCTA TAAAAACCCA GATCTCTCGA GGTCGACGGT ATCGATAAGC TTAAATTGTA    780

TTCATGTTAT TTTTCATAAT TTATTTTTAT GAATGAATGC TTTTTTACTG ATTAATCGAT    840

ATTTTTGGGT CTAGAGAGCT CCAGCTGCCA TAGCTATTCG ATGATATCGA ATTCATAAAA    900

ATTATTGATG TCTACACATC CTTTTGTAAT TGACATCTAT ATATCCTTTT GTATAATCAA    960

CTCTAATCAC TTTACTATAG CTTAAGTATT TTTAATAACT ACAGATGTGT AGGAAAACAT   1020

TAACTGTAGA TATATAGGAA AACATATTAG TTGAGATTAG TGAAACGTAA CTTTTACAGT   1080

TTTCCCTACC AGTTTATCCC TATATTCAAC ATATCTATCC ATATGCATCT TAACACTCTC   1140

TGCCAAGATA GCTTCAGATT GAAAATGTCA AAAGGGATGG TCAAATAGGG ATATAAGTTG   1200

TATAGATAGG TATACGTAGA ATTGTGAGAG ACGGTTCTAT CGAAGTCTTG AAGTGAGGAT   1260
```

-continued

```
AGTCAAAAAG ATAAATGTAT AGAGCATAAT CCTTCTCGTA TACTCTGCCC TTTATTACAT   1320
CGCCCGCATT GGGCAACGAA TACACTCCTA TCAGTTTTTC TATTTACATA TCTCGTATTA   1380
GGAAGAGCAT ATGAGACGGG AAATAATGTA GCGGGCGTAA CCCGTTGCTT ATAGGAACAA   1440
AATGCAAGCA TACGATACAA ACTTAACGGA TATCGCGATA ATGAAATAAT TTATGATTAT   1500
TTCTCGCTTT CAATTTAACA CAACCCTCAA GAACTGTTTT ACGTTCGTAT GCTATGTTTG   1560
AATTGCCTAT AGCGCTATTA CTTTATTAAA TACTAATAAA GAGCGAAAGT TAAATTGTGT   1620
TGGGAGTTCT TGCACTTTGT ATTTATTTTC ACTTTTTAAG TATAGAATAA AGAAAGCTCT   1680
AATTAATTAA TGAACAGATT GTTTCGTTTT CCCCTTGGCG TATCACTAAT TAATTAACCC   1740
GGGCGAAACA TAAATAAAAG TGAAAAATTC ATATCTTATT TCTTTCGAGA TTAATTAATT   1800
ACTTGTCTAA CAAAGCAAAA GGGGAACCGC ATAGTGATTA ATTAATTGGG CCCGTGCAGC   1860
TCGAGGAATT CAACTATATC GACATATTTC ATTTGTATAC ACATAACCAT TACTAACGTA   1920
GAATGTATAG GAAGAGATGT AACGGGAACA GGGTTTGTTG ATTCACGTCG AGCTCCTTAA   1980
GTTGATATAG CTGTATAAAG TAAACATATG TGTATTGGTA ATGATTGCAT CTTACATATC   2040
CTTCTCTACA TTGCCCTTGT CCCAAACAAC TAAGGCAAAC TATTCTAATA CATAATTCTT   2100
CTGTTAATAC GTCTTGCACG TAATCTATTA TAGATGCCAA GATATCTATA TAATTATTTT   2160
GTAAGATGAT GTTAACTATG TGATCGTTTG ATAAGATTAT GTATTAAGAA GACAATTATG   2220
CAGAACGTGC ATTAGATAAT ATCTACGGTT CTATAGATAT ATTAATAAAA CATTCTACTA   2280
CAATTGATAC ACTACTATAT AAGTAGTGTA ATAATTCATG TATTTCGATA TATGTTCCAA   2340
CTCTGTCTTT GTGATGTCTA GTTTCGTAAT ATCTATAGCA TCCTCAAAAA ATATATTCGC   2400
ATATGATATA TTCATCACAT TATTAAGTAC ATAAAGCTAT ATACAAGGTT GAGACAGAAA   2460
CACTACAGAT CAAAGCATTA TAGATATCGT AGGAGTTTTT TATATAAGCG TATAATTCCC   2520
AAGTCTTCAG TTCTATCTTC TAAAAAATCT TCAACGTATG GAATATAATA ATCTATTTTA   2580
CCTCTTCTGA TATCATTAAT GATATAGTTT TTGACACTAT CTTCTAAGGG TTCAGAAGTC   2640
AAGATAGAAG ATTTTTTAGA AGTTGCATAC CTTATATTAT TAGATAAAAT GGAGAAGACT   2700
ATAGTAATTA CTATATCAAA AACTGTGATA GAAGTGTCAA TTGATTCTTA TTCACTATAT   2760
CTAAGAAACG GATAGCGTCC CTAGGACGAA CTACTGCCAT TAATATCTCT ATTATAGCTT   2820
CTGGACATAA TTCATCTATT ATACACAGTT AACTAAGAAT AAGTGATATA GATTCTTTGC   2880
CTATCGCAGG GATCCTGCTT GATGACGGTA ATTATAGAGA TAATATCGAA GACCTGTATT   2940
AAGTAGATAA TATGCAGAAT TAATGGGAAC TATTCCGTAT CTATCTAACA TAGTTTTAAG   3000
AAAGTCAGAA TCTAAGACCT GATGTTCATA TATTGGTTCA TACATGAAAT GATCTCTATT   3060
GATGGTCTTA ATTACCCTTG ATAAGGCATA GATAGATTGT ATCAAAATTC TTTCAGTCTT   3120
AGATTCTGGA CTACAAGTAT ATAACCAAGT ATGTACTTTA CTAGAGATAA CTACATAGTG   3180
ACTATTTCAT TCTCTGAAAA TTGGTAACTC ATTCTATATA TGCTTTCCTT GTTGATGAAG   3240
GATAGAATAT ACTCAATAGA ATTTGTACCA ACAAACTGTT CTCTTATCAC TGATAAAGTA   3300
AGAGACTTTT AACCATTGAG TAAGATATAT ACGAAAGGAA CAACTACTTC CTATCTTATA   3360
TGAGTTATCT TAAACATGGT TGTTTGACAA GAGATATGAA TCGTATATCA TCATCTGAAA   3420
TAATCATGTA AGGCATACAT TTAACAATTA GAGACTTGTC TCCTGTTATC AATATACTAT   3480
TCTTGTGATA ATTTATGTGT GAGGATACTT AGCATATAGT AGTAGACTTT ATTAGTACAT   3540
TCCGTATGTA AATTGTTAAT CTCTGAACAG AGGACAATAG TTATATGATA AGAACACTAT   3600
TAAATACACA CTCCCAAATT TGTCCACGTT CTTTAATTTT GTTATAGTAG ATATCAAATC   3660
```

```
CAATGGAGCT ACAGTTCTTG GCTTAAACAG ATATAGTTTT TCTGGAACAA ATTCTACAAC   3720
ATTAGTTTAA ACAGGTGCAA GAAATTAAAA CAATATCATC TATAGTTTAG GTTACCTCGA   3780
TGTCAAGAAC CGAATTTGTC TATATCAAAA AGACCTTGTT TAAGATGTTG TAATTTATAA   3840
AGGACTTTGG GTAGATAAGT GGGATGAAAT CCTATTTTAA TTAATGCTAT CGCATTGTCC   3900
TCGTGCAAAT ATCCAAACGC TTTTGTGATA GTATGGCATT CATTAATATT TCCTGAAACC   3960
CATCTATTCA CCCTACTTTA GGATAAAATT AATTACGATA GCGTAACAGG AGCACGTTTA   4020
TAGGTTTGCG AAAACACTAT CATACCGTAA GTAAGTCTAG AAACGCTCTA CGAATATCTG   4080
TGACAGATAT CATCTTTAGA GAATATACTA GTCGCGTTAA TAGTACTACA ATTTGTATTT   4140
TTTAATCTAT CTCAATAAAA AAATCAGATC TTTGCGAGAT GCTTATAGAC ACTGTCTATA   4200
GTAGAAATCT CTTATATGAT CAGCGCAATT ATCATGATGT TAAACATAAA AAATTAGATA   4260
GAGTTATTTT TTTATAATAT GTATGATTCA ATGTATAACT AAACTACTAA CTGTTATTGA   4320
TAACTAGAAT CAGAATCTAA TGATGACGTA ACCAAGAAGT TTATCTACTG CCAAATTATA   4380
CATACTAAGT TACATATTGA TTTGATGATT GACAATAACT ATTGATCTTA GTCTTAGATT   4440
ACTACTGCAT TGGTTCTTCA AATAGATGAC GGTTGATTTA GCTGCATTAT TTTTAGCATC   4500
TCGTTTAGAT TTTCCATCTG CCTTATCGAA TACTCTTCCG TCGATGTCTA CACAGGCATA   4560
AAATGTAAAT CGACGTAATA AAAATCGTAG AGCAAATCTA AAAGGTAGAC GGAATAGCTT   4620
ATGAGAAGGC AGCTACAGAT GTGTCCGTAT TTTACAAAAG AGCATAGGAG AGTTACTAGG   4680
CCCAACTGAT TCAATACGAA AAGACCAATC TCTCTTAGTT ATTTGGCAGT ACTCATTAAT   4740
AATGGTGACA GGGTTTCCTC TCAATGATCC GGGTTGACTA AGTTATGCTT TTCTGGTTAG   4800
AGAGAATCAA TAAACCGTCA TGAGTAATTA TTACCACTGT CCCAAGTCTA GCATCTTTCC   4860
AATCAATAAT TTTTTTAGCC GGAATAACAT CATCAAAAGA CTTATGATCC TCTCTCATTG   4920
ATTTTTCGCG GGATACATCT CGTAGAAAGG TTAGTTATTA AAAAAATCGG CCTTATTGTA   4980
GTAGTTTTCT GAATACTAGG AGAGAGTAAC TAAAAAGCGC CCTATGTAGA AATCTATTAT   5040
GACGTCAGCC ATAGCATCAG CATCCGGCTT ATCCGCCTCC GTTGTCATAA ACCAACGAGG   5100
AGGAATATCG TCGGAGCTGT ATAGATAATA CTGCAGTCGG TATCGTAGTC GTAGGCCGAA   5160
TAGGCGGAGG CAACAGTATT TGGTTGCTCC TCCTTATAGC AGCCTCGACA TAAAATTCAC   5220
CATAGCACTA CGTTGAAGAT CGTACAGAGC TTTATTAACT TCTCGCTTCT CCATATTAAG   5280
TTGTCTAGTT AGTTGTGCAG CAGTAGCGTG GTATCGTGAT GCAACTTCTA GCATGTCTCG   5340
AAATAATTGA AGAGCGAAGA GGTATAATTC AACAGATCAA TCAACACGTC GTCATCGAAT   5400
AATATCCTTC GATTCCAATG TTTTTAATAG CCGCACACAC AATCTCTGCG TCAGAACGCT   5460
CGTCAATATA GATCTTAGAC ATTTTTAGAG AGAAAGGAAG CTAAGGTTAC AAAAATTATC   5520
GGCGTGTGTG TTAGAGACGC AGTCTTGCGA GCAGTTATAT CTAGAATCTG TAAAAATCTC   5580
TCTTGGAACA CTAACACAAC CAGCAATAAA ACTGAACCTA CTTTATCATT TTTTTATTCA   5640
TCATCCTCTG GTGGTTCGTC GTTTCTATCG AATGTAGCTC TGATTAACCC GTCATCTATA   5700
GATTGTGTTG GTCGTTATTT TGACTTGGAT GAAATAGTAA AAAAATAAGT AGTAGGAGAC   5760
CACCAAGCAG CAAAGATAGC TTACATCGAG ACTAATTGGG CAGTAGATAT GGTGATGCTG   5820
GTTCTGGAGA TTCTGGAGGA GATGGATTAT TATCTGGAAG AATCTCTGTT ATTTCCTTGT   5880
TTTCATGTAT CGATTGCGTT GTAACATTAA GATTGCGAAA CCACTACGAC CAAGACCTCT   5940
AAGACCTCCT CTACCTAATA ATAGACCTTC TTAGAGACAA TAAAGGAACA AAAGTACATA   6000
GCTAACGCAA CATTGTAATT CTAACGCTTT TGCTCTAAAT TTGGGAGGCT TAAAGTGTTG   6060
```

-continued

```
TTTGCAATCT CTACACGCGT GTCTAACTAG TGGAGGTTCG TCAGCTGCTC TAGTTTGAAT   6120
CATCATCGGC GTAGTATTCC ACGAGATTTA AACCCTCCGA ATTTCACAAC AAACGTTAGA   6180
GATGTGCGCA CAGATTGATC ACCTCCAAGC AGTCGACGAG ATCAAACTTA GTAGTAGCCG   6240
CATCATAAGG TACTTTTACA GTTAGGACAC GGTGTATTGT ATTTCTCGTC GAGAACGTTA   6300
AAATAATCGT TGTAACTCAC ATCCTTTATT TTATCTATAT TGTATTCTAC TCCTTTCTTA   6360
ATGAAAATGT CAATCCTGTG CCACATAACA TAAAGAGCAG CTCTTGCAAT TTTATTAGCA   6420
ACATTGAGTG TAGGAAATAA AATAGATATA ACATAAGATG AGGAAAGAAT ATGCATTTTA   6480
TACCGAATAA GAGATAGCGA AGGAATTCTT TTTATTGATT AACTAGTCAA ATGAGTATAT   6540
ATAATTGAAA AAGTAAAATA TAAATCATAT AATAATGAAA TACGTAAAAT ATGGCTTATT   6600
CTCTATCGCT TCCTTAAGAA AAATAACTAA TTGATCAGTT TACTCATATA TATTAACTTT   6660
TTCATTTTAT ATTTAGTATA TTATTACTTT CGAAATATCA GTAATAGACA GGAACTGGCA   6720
GATTCTTCTT CTAATGAAGT AAGTACTGCT AAATCTCCAA AATTAGATAA AAATGATACA   6780
GCAAATACAG CTTCATTCAA GCTTTATAGT CATTATCTGT CCTTGACCGT CTAAGAAGAA   6840
GATTACTTCA TTCATGACGA TTTAGAGGTT TTAATCTATT TTTACTATGT CGTTTATGTC   6900
GAAGTAAGTT CGAATTACCT TTTAATTTTT TCAGACACAC CTTATTACAA ACTAACTAAG   6960
TCAGATGATG AGAAAGTAAA TATAAATTTA ACTTATGGGT ATAATATAAT AAAGATTCAT   7020
GCTTAATGGA AAATTAAAAA AGTCTGTGTG GAATAATGTT TGATTGATTC AGTCTACTAC   7080
TCTTTCATTT ATATTTAAAT TGAATACCCA TATTATATTA TTTCTAAGTA GATATTAATA   7140
ATTTACTTAA CGATGTTAAT AGACTTATTC CATCAACCCC TTCAAACCTT TCTGGATATT   7200
ATAAAATACC AGTTAATGAT ATTAAAATAG ATTGTTTAAG CTATAATTAT TAAATGAATT   7260
GCTACAATTA TCTGAATAAG GTAGTTGGGG AAGTTTGGAA AGACCTATAA TATTTTATGG   7320
TCAATTACTA TAATTTTATC TAACAAATTC AGATGTAAAT AATTATTTGG AGGTAAAGGA   7380
TATAAAATTA GTCTATCTTT CACATGGAAA TGAATTACCT AATATTAATA ATTATGATAG   7440
GAATTTTTTA GGATTTACAG TCTACATTTA TTAATAAACC TCCATTTCCT ATATTTTAAT   7500
CAGATAGAAA GTGTACCTTT ACTTAATGGA TTATAATTAT TAATACTATC CTTAAAAAAT   7560
CCTAAATGTC CTGTTATATG TATCAACAAT ACAGGCAGAT CTATGGTTAT GGTAAAACAC   7620
TGTAACGGGA AGCAGCATTC TATGGTAACT GGCCTATGTT TAATAGCCAG ATCATTTTAC   7680
GACAATATAC ATAGTTGTTA TGTCCGTCTA GATACCAATA CCATTTTGTG ACATTGCCCT   7740
TCGTCGTAAG ATACCATTGA CCGGATACAA ATTATCGGTC TAGTAAAATG TCTATAAACA   7800
TTTTACCACA AATAATAGGA TCCTCTAGAT ATTTAATATT ATATCTAACA ACAACAAAAA   7860
AATTTAACGA TGTATGGCCA GAAGTATTTT CTACTAATAA AGATATTTGT AAAATGGTGT   7920
TTATTATCCT AGGAGATCTA TAAATTATAA TATAGATTGT TGTTGTTTTT TTAAATTGCT   7980
ACATACCGGT CTTCATAAAA GATGATTATT AGATAAAGAT AGTCTATCTT ATCTACAAGA   8040
TATGAAAGAA GATAATCATT TAGTAGTAGC TACTAATATG GAAAGAAATG TATACAAAAA   8100
CGTGGAAGCT TTTATATTAA TCTATTTCTA TCAGATAGAA TAGATGTTCT ATACTTTCTT   8160
CTATTAGTAA ATCATCATCG ATGATTATAC CTTTCTTTAC ATATGTTTTT GCACCTTCGA   8220
AAATATAATT ATAGCATATT ACTAGAAGAT TTAAAATCTA GACTTAGTAT AACAAAACAG   8280
TTAAATGCCA ATATCGATTC TATATTTCAT CATAACAGTA GTACATTAAT CAGTGATATA   8340
TATCGTATAA TGATCTTCTA AATTTTAGAT CTGAATCATA TTGTTTTGTC AATTTACGGT   8400
TATAGCTAAG ATATAAAGTA GTATTGTCAT CATGTAATTA GTCACTATAT CTGAAACGAT   8460
```

```
CTACAGACTC AACTATGCAA GGAATAAGCA ATATGCCAAT TATGTCTAAT ATTTTAACTT   8520
TAGAACTAAA ACGTTCTACC AATACTAAAA ATAGGATACG GACTTTGCTA GATGTCTGAG   8580
TTGATACGTT CCTTATTCGT TATACGGTTA ATACAGATTA TAAAATTGAA ATCTTGATTT   8640
TGCAAGATGG TTATGATTTT TATCCTATGC TGATAGGCTG TTAAAAGCTG CAATAAATAG   8700
TAAGGATGTA GAAGAAATAC TTTGTTCTAT ACCTTCGGAG GAAAGAACTT TAGAACAACT   8760
TAAGTTTAAT CAAACTTGTA ACTATCCGAC AATTTTCGAC GTTATTTATC ATTCCTACAT   8820
CTTCTTTATG AAACAAGATA TGGAAGCCTC CTTTCTTGAA ATCTTGTTGA ATTCAAATTA   8880
GTTTGAACAT TTTATGAAGG TACCAAATAC TTCCATGGTT TTTTTTCATT ATTTAGAAAT   8940
TATGCATTTT AGATCTTTAT AAGCGGCCGT GATTAACTAG TCATAAAAAC CCGGGATCGA   9000
TTCTAGACTC GAGGGTACCG GATCTTAATA AAAAAAGTAA TAAATCTTTA ATACGTAAAA   9060
TCTAGAAATA TTCGCCGGCA CTAATTGATC AGTATTTTTG GGCCCTAGCT AAGATCTGAG   9120
CTCCCATGGC CTAGAATTAT AATTAGTCAT CAGGCAGGGC GAGAACGAGA CTATCTGCTC   9180
GTTAATTAAT TAGGTCGACG GATCCCCCAA CAAAAACTAA TCAGCTATCG GGGTTAATTA   9240
ATTAGTTATA TTAATCAGTA GTCCGTCCCG CTCTTGCTCT GATAGACGAG CAATTAATTA   9300
ATCCAGCTGC CTAGGGGGTT GTTTTTGATT AGTCGATAGC CCCAATTAAT TAATCAATAT   9360
AGACAAGGTG AAAACGAAAC TATTTGTAGC TTAATTAATT AGAGCTTCTT TATTCTATAC   9420
TTAAAAAGTG AAAATAAATA CAAAGGTTCT TGAGGGTTGT GTTAAATTGA TCTGTTCCAC   9480
TTTTGCTTTG ATAAACATCG AATTAATTAA TCTCGAAGAA ATAAGATATG AATTTTTCAC   9540
TTTTATTTAT GTTTCCAAGA ACTCCCAACA CAATTTAACT AAAGCGAGAA ATAATCATAA   9600
ATTATTTCAT TATCGCGATA TCCGTTAAGT TTGTATCGTA ATGCCACTAA CAGAAGAAGC   9660
AGAGCTAGAA CTGGCAGAAA ACTTTCGCTC TTTATTAGTA TTTAATAAAG TAATAGCGCT   9720
ATAGGCAATT CAAACATAGC ATTACGGTGA TTGTCTTCTT CGTCTCGATC TTGACCGTCT   9780
TTTGTTTGGA AGGAAGATAG AGAGATTCTA AAAGAACCAG TACATGGAGT GTATTATGAC   9840
CCATCAAAAG ACTTAATAGC AGAAATACAG AAGCAGGGGC AAGGCCAATC TCTCTAAGAT   9900
TTTCTTGGTC ATGTACCTCA CATAATACTG GGTAGTTTTC TGAATTATCG TCTTTATGTC   9960
TTCGTCCCCG TTCCGGTTAG GGAGATTAAA AGGGGGGGTT GGACATATCA AATTTATCAA  10020
GAGCCATTTA AAAATCTGAA AACAGGAATG GAGTGGAGAT TTGATTCTAG ATTAGCATTT  10080
CATCACGTAA CCTGTATAGT TTAAATAGTT CTCGGTAAAT TTTTAGACTT TTGTCCTTAC  10140
CTCACCTCTA AACTAAGATC TAATCGTAAA GTAGTGCATT TTGTGGATGT GTAGAAGAAA  10200
TGCTAGAGAA TTACATCCTG AATATTTTAA AAATTGTAAG CTTATGGCAA TATTCCAAAG  10260
TAGCATGACA AAAATCTTAG AGCCTTTTAG ACGATCTCTT AATGTAGGAC TTATAAAATT  10320
TTTAACATTC GAATACCGTT ATAAGGTTTC ATCGTACTGT TTTTAGAATC TCGGAAAATC  10380
TAAAGGGTAC TAAGTTGAGT AAACAAAATC CAGACATAGT TATCTATCAA TACATGGATG  10440
ATTTGTATGT AGGATCTGAC TTAGAAATAG GGCAGCATAG AACAAAAATA TTTGTTTTAG  10500
GTCTGTATCA ATAGATAGTT ATGTACCTAC TAAACATACA TCCTAGACTG AATCTTTATC  10560
CCGTCGTATC TTGTTTTTAT GAAATGTTAA TAGAGGGAGT TGAGGAGCTG AGACAACATC  10620
TGTTGAGGTG GGACTTACA ACCATGGTAG GTTTTCCAGT AACACCTCAA GTACCTTTAA  10680
GACCAATGAC TCTCCTCGAC TCTGTTGTAG ACAACTCCAC CCCTGAATGT TGGTACCATC  10740
CAAAAGGTCA TTGTGGAGTT CATGGAAATT CTGGTTACTG AGGAGGAGTG TTTAGATGAA  10800
GTTTTACAAA GCAGCTGTAG ATCTTTCTCA CTTTTTAAAA GAAAAAGGAG GTTTAGAAGG  10860
```

-continued

```
GCTAATTCAT TCTCAACGAA GACAAGATAT TCTTATGTTT CGTCGACATC TAGAAAGAGT  10920
GAAAAATTTT CTTTTTCCTC CAAATCTTCC CGATTAAGTA AGAGTTGCTT CTGTTCTATA  10980
AGAATAAAAA AGGGGGGAGA GGATGATTTG TGGATTTATC ATACACAAGG ATATTTTCCT  11040
GATTGGCAGA ATTACACACC AGGACCAGGA GTCAGATACC CATTAACCTT TGGTCTAAAC  11100
ACCTAAATAG TATGTGTTCC TATAAAAGGA CTAACCGTCT TAATGTGTGG TCCTGGTCCT  11160
CAGTCTATGG GTAATTGGAA ACCAATTTGG TATGATTGGA AGTTGTTGGT GCTACAAGCT  11220
AGTACCAATG ATTGAGACTG TACCAGTAAA ATTAAAGCCA GGAATGGATG GCCCAAAAGT  11280
TAAACAATGG CCATTGACCA CGATGTTCGA TCATGGTTAC TAACTCTGAC ATGGTCATTT  11340
TAATTTCGGT CCTTACCTAC CGGGTTTTCA ATTTGTTACC GGTAACTCTA TGTAAGTAGA  11400
GTTACAGAAG AAAAAATAAA AGCATTAGTA GAAATTTGTA CAGAGATGGA AAAGGAAGGG  11460
AAAATTTCAA AAATTGGGCC TTAATTTTTC TTGTCTTCTT TTTTATTTTC GTAATCATCT  11520
TTAAACATGT CTCTACCTTT TCCTTCCCTT TTAAAGTTTT TAACCCGGAA TTAAAAAGAT  11580
GGAAAGCTGT GGGGTGCAGC CCGGGGGATC CTTTTTATAG CTAATTAGTC ACGTACCTTT  11640
GAGAGTACCA CTTCAGCTAC CTCTTTTGTG TCTCAGAGTA ACTTTCTTTA ATCAATTCCA  11700
AAACACGTCG GGCCCCCTAG GAAAAATATC GATTAATCAG TGCATGGAAA CTCTCATGGT  11760
GAAGTCGATG GAGAAAACAC AGAGTCTCAT TGAAAGAAAT TAGTTAAGGT TTTGTGAGAG  11820
TAAATTACTA GCAGAAGCTA AGAGCGGAGC ACCATAGACC ATAGGAGGAG CAGATAATGT  11880
AGTATACTAA TATTAACTCA CATTTGACTA ATTAGCTATA AAAACCCGGG ATCGATTCTA  11940
GAATAAAAAT TATCCCTGCC TAACTCTATT CACTACAGAG AGTACAGCAA AAACATTACA  12000
TCATATGATT ATAATTGAGT GTAAACTGAT TAATCGATAT TTTTGGGCCC TAGCTAAGAT  12060
CTTATTTTTA ATAGGGACGG ATTGAGATAA GTGATGTCTC TCATGTCGTT TTTGCAGAGA  12120
TAAGTATTCT TAAACCTACC AAGCCTCCTA CTATCATTAT GAATAATCTT TTTTCTCTCT  12180
GCACCACTCT TCTCTTTGCC TTGGTGGGTG CTACTCCTAA TGGTTCAATT GTTACTACTT  12240
TATAATAAGA ATTTGGATGG TTCGGAGGAT GATAGTAATA CTTATTAGAA AAAAGAGAGA  12300
CGTGGTGAGA AGAGAAACGG AACCACCCAC GATGAGGATT ACCAAGTTAA CAATGATGAA  12360
ATATGGGATA GTTAAGGGTT TATATAATTC ACTTCTCCAA TTGTCCCTCA TATCTCCTCC  12420
TCCAGGTCTG AAGATCTCGG TGTCGTTCGT GTCCGTGTCC TTACCACCAT CTCTTGTTAA  12480
TAGTAGCCCT GTAATATTAA ATATATTAAG TGAAGAGGTT AACAGGGAGT ATAGAGGAGG  12540
AGGTCCAGAC TTCTAGAGCC ACAGCAAGCA CAGGCACAGG AATGGTGGTA GAGAACAATT  12600
ATCATCGGGA CATTATAAGG GTTTGGTGTG GTGATGAACA TCTAATTTGT CCTTCAATGG  12660
GAGGGGCATA TATTGCTTTT CCTACTTCCT GCCACATGTT TATAATTTGT TTTATTTTGC  12720
ATTGAAGTGT GATATTGTTA TTTGACCCTG TACTACTTGT AGATTAAACA GGAAGTTACC  12780
CTCCCCGTAT ATAACGAAAA GGATGAAGGA CGGTGTACAA ATATTAAACA AAATAAAACG  12840
TAACTTCACA CTATAACAAT AAACTGGGAC ACGAAGCTGT GGAGTATTAT TCCAAGTATT  12900
ATTACCATTC CAAGTACTAT TAAACAGTGG TGATGAATTA CAGTAGAAGA ATTCCCCTCC  12960
ACAATTAAAA CTGTGCATTA CAATTTCTGG GTCCCCTCCT GATCATAATA AGGTTCATAA  13020
TAATGGTAAG GTTCATGATA ATTTGTCACC ACTACTTAAT GTCATCTTCT TAAGGGGAGG  13080
TGTTAATTTT GACACGTAAT GTTAAAGACC CAGGGGAGGA CTTTGTCGGC GGGGGGATTG  13140
ATTAAAGACT ATTGTTTTAT TCTTAAATTG TTCTTTTAAT TTGCTAACTA TCTGTCTTAA  13200
AGTGTCATTC CATTTTGCTC TACTAATGTT ACAATGTGCT TGTCTTATAG TTCCCCTAAC  13260
```

-continued

```
TAATTTCTGA TAACAAAATA AGAATTTAAC AAGAAAATTA AACGATTGAT AGACAGAATT  13320
TCACAGTAAG GTAAAACGAG ATGATTACAA TGTTACACGA ACAGAATATC AAGGTTACAT  13380
GGGTATTATA TTTTTTGTTG TATAAAATGC TCTCCCTGGT CCTATATGTA TCCTTTTTCT  13440
TTTATTGTAG TTGGGTCTTG TACAATTAAT TTGTACAGAT TCATTCAGAT GTACTATGAT  13500
GGTATAATAT AAAAAACAAC ATATTTTACG AGAGGGACCA GGATATACAT AGGAAAAAGA  13560
AAATAACATC AACCCAGAAC ATGTTAATTA AACATGTCTA AGTAAGTCTA CATGATACTA  13620
CCATTAGGTC TGGTTTAGCA TTATCATTGA AATTCTCAGA TCTAATTACT ACCTCTTCTT  13680
CTGCTAGACT GCCATTTAAC AGCAGTTGAG TTGATACTAC TGGCCTAATT CCATGTGTAC  13740
ATTGTACTGT GCTAAATCGT AATAGTAACT TTAAGAGTCT AGATTAATGA TGGAGAAGAA  13800
GACGATCTGA CGGTAAATTG TCGTCAACTC AACTATGATG ACCGGATTAA GGTACACATG  13860
TAACATGACA CGAAAGTGTC TGGGACATTT TTACATGATC CTTTTCCACT GAACTTTTTA  13920
TCGTTACACT TTAGAATCGC AAAACCAGCC GGGGCACAAT AGTGTATGGG AATTGGCTCA  13980
AAGGATATCT TTGGACAAGC TTGCTGTAAA AATGTACTAG GAAAAGGTGA CTTGAAAAAT  14040
AGCAATGTGA AATCTTAGCG TTTTGGTCGG CCCCGTGTTA TCACATACCC TTAACCGAGT  14100
TTCCTATAGA AACCTGTTCG AACCGGCAGA ACCAGGTGTA ATGACTGAGG TATTACAACT  14160
TATCAACCTA TAGCTGGTAC TATCATTATT TATTGATACT ATATCAAGTT TATAAAGAAG  14220
TGCATATTCT TTCTGCATCT TATCTCTTAT GCTTGTACAT TACTGACTCC ATAATGTTGA  14280
ATAGTTGGAT ATCGACCATG ATAGTAATAA ATAACTATGA TATAGTTCAA ATATTTCTTC  14340
ACGTATAAGA AAGACGTAGA ATAGAGAATA CGAACATTCT ATGGGGTGAT ATTGAAAGAG  14400
CAGTTTTTCA TTTCTCCTCC CTTTATTGTT CCCTCGCTAT TACTATTGTT ATTAGCAGTA  14460
CTATTATTGG TATTAGTAGT ATTCCTCAAA TCAGTGCAAT TTAACCACTA TAACTTTCTC  14520
GTCAAAAAGT AAAGAGGAGG GAAATAACAA GGGAGCGATA ATGATAACAA TAATCGTCAT  14580
GATAATAACC ATAATCATCA TAAGGAGTTT AGTCACGTTA AATTTCGGTG ATTTTTCGGA  14640
GTAACACAGA GTGGGGTTAA TTTTACACAT GGCTTTAGGC TTTGATCCCA TAAACTGATT  14700
ATATCCTCAT GCATCTGTTC TACCATGTTA TTTTTCCACA TGTTAAAATT TTCTGTCACT  14760
CATTGTGTCT CACCCCAATT AAAATGTGTA CCGAAATCCG AAACTAGGGT ATTTGACTAA  14820
TATAGGAGTA CGTAGACAAG ATGGTACAAT AAAAAGGTGT ACAATTTTAA AAGACAGTGT  14880
CTCTGGATTT ACCAATTCTA CTTCTTGTGG GTTGGGGTCT GTGGGTACAC AGGCATGTGT  14940
GGCCCAAACA TTATGTACCT CTGTATCATA TGCTTTAGCA TCTGATGCAC AAAATAGAGT  15000
GGTGGTTAAA TGGTTAAGAT GAAGAACACC CAACCCCAGA CACCCATGTG TCCGTACACA  15060
CCGGGTTTGT AATACATGGA GACATAGTAT ACGAAATCGT AGACTACGTG TTTTATCTCA  15120
CCACCATCAT ATAAACTTTG GTGCTTCTTT CCACACAGGT ACCCCATAAT AGACTGTGAC  15180
CCACAATTTT TCTGTAGCAC TACAGATCAT CAACATCCCA AGGAGCATGG TGCCCCATCT  15240
CCACCCCCAT CTCCACAAGT GACGAAGAAA GGTGTGTCCA TGGGGTATTA TCTGACACTG  15300
GGTGTTAAAA AGACATCGTG ATGTCTAGTA GTTGTAGGGT TCCTCGTACC ACGGGGTAGA  15360
GGTGGGGGTA GAGGTGTTCA CAGTTACGTG GGGCTGATAT TTCTCCTTCA CTCTCATTGC  15420
CACTGTCTTC TGCTCTTTCA TATACGATAC AAACTTAACG CATATCGCGA TAATGAAATA  15480
ATTTATGATT ATTTCTCGCT TTCAATTTAA CACGACTATA AAGAGGAAGT GAGAGTAACG  15540
GTGACAGAAG ACGAGAAAGT ATATGCTATG TTTGAATTGC GTATAGCGCT ATTACTTTAT  15600
TAAATACTAA TAAAGAGCGA AAGTTAAATT GTGATGGACC ATAACCCTCA AGAACCTTTG  15660
```

-continued

TATTTATTTT CACTTTTTAA GTATAGAATA AAGAAGCTCT AATTAATTAA GCTACAAATA 15720

GTTTCGTTTT CACCTTGTCT AATAACTAAT TAATTAACCC GGTTGGGAGT TCTTGGAAAC 15780

ATAAATAAAA GTGAAAAATT CATATCTTAT TTCTTCGAGA TTAATTAATT CGATGTTTAT 15840

CAAAGCAAAA GTGGAACAGA TTATTGATTA ATTAATTGGG CCACCATATC TTGAGATAAA 15900

GTGAAAATAT ATATCATTAT ATTACAAAGT ACAATTATTT AGGTTTAATC ATGGGTGCGA 15960

GAGCGTCAGT ATTAAGCGGG GGAGAATTAG ATCGATGGGA AAAAATTTAG AACTCTATTT 16020

CACTTTTATA TATAGTAATA TAATGTTTCA TGTTAATAAA TCCAAATTAG TACCCACGCT 16080

CTCGCAGTCA TAATTCGCCC CCTCTTAATC TAGCTACCCT TTTTTAAACC ATGAAGGGAG 16140

GCGGTTAAGG CCAGGGGGAA AGAAAAAATA TAAATTAAAA CATATAGTAT GGGCAAGCAG 16200

GGAGCTAGAA CGATTCGCAG TTAATCCTGG CCTGTTAGAA ACATCAGAAG GCTGTAGACA 16260

AGCCAATTCC GGTCCCCCTT TCTTTTTTAT ATTTAATTTT GTATATCATA CCCGTTCGTC 16320

CCTCGATCTT GCTAAGCGTC AATTAGGACC GGACAATCTT TGTAGTCTTC CGACATCTGT 16380

TGGAAGTGCG AGGATACTGG GACAGCTACA ACCATCCCTT CAGACAGGAT CAGAAGAACT 16440

TAGATCATTA TATAATACAG TAGCAACCCT CTATTGTGTG CATCAAAGGA TAGAGATAAA 16500

AGACACCAAG GAATATGACC CTGTCGATGT TGGTAGGGAA GTCTGTCCTA GTCTTCTTGA 16560

ATCTAGTAAT ATATTATGTC ATCGTTGGGA GATAACACAC GTAGTTTCCT ATCTCTATTT 16620

TCTGTGGTTC CTTGTGTATC TGAGGGCTTT AGACAAGATA GAGGAAGAGC AAAACAAAAG 16680

TAAGAAAAAA GCACAGCAAG CAGCAGCTGA CACAGGACAC AGCAATCAGG TCAGCCAAAA 16740

TTACCCTATA GTGCAGAACA TCCAGCGAAA TCTGTTCTAT CTCCTTCTCG TTTTGTTTTC 16800

ATTCTTTTTT CGTGTCGTTC GTCGTCGACT GTGTCCTGTG TCGTTAGTCC AGTCGGTTTT 16860

AATGGGATAT CACGTCTTGT AGGTCAAAAA TGGAGGGGGC AAATGGTACA TCAGGCCATA 16920

TCACCTAGAA CTTTAAATGC ATGGGTAAAA GTAGTAGAAG AGAAGGCTTT CAGCCCAGAA 16980

GTGATACCCA TGTTTTCAGC ATTATCAGAA GGAGCCCCCG TTTACCATGT AGTCCGGTAT 17040

AGTGGATCTT GAAATTTACG TACCCATTTT CATCATCTTC TCTTCCGAAA GTCGGGTCTT 17100

CACTATGGGT ACAAAAGTCG TAATAGTCTT CCTCGGGATA AAGAGAGGAC CCCACAAGAT 17160

TTAAACACCA TGCTAAACAC AGTGGGGGGA CATCAAGCAG CCATGCAAAT GTTAAAAGAG 17220

ACCATCAATG AGGAAGCTGC AGAATGGGAT AGAGTGCATC CAGTGCATTG GGGTGTTCTA 17280

AATTTGTGGT ACGATTTGTG TCACCCCCCT GTAGTTCGTC GGTACGTTTA CAATTTTCTC 17340

TGGTAGTTAC TCCTTCGACG TCTTACCCTA TCTCACGTAG GTCACGTATT TGGAATAAGA 17400

GGGCAGGGCC TATTGCACCA GGCCAGATGA GAGAACCAAG GGGAAGTGAC ATAGCAGGAA 17460

CTACTAGTAC CCTTCAGGAA CAAATAGGAT GGATGACAAA TAATCCACCT ATCCCAGTAG 17520

GACGTCCCGG ATAACGTGGT CCGGTCTACT CTCTTGGTTC CCCTTCACTG TATCGTCCTT 17580

GATGATCATG GGAAGTCCTT GTTTATCCTA CCTACTGTTT ATTAGGTGGA TAGGGTCATC 17640

CTAGAGGAGT TTGTGGAGGG AAATTTATAA AAGATGGATA ATCCTGGGAT TAAATAAAAT 17700

AGTAAGAATG TATAGCCCTA CCAGCATTCT GGACATAAGA CAAGGACCAA AAGAACCCTT 17760

TAGAGACTAT GTAGACCGGC TTTAAATATT TTCTACCTAT TAGGACCCTA ATTTATTTTA 17820

TCATTCTTAC ATATCGGGAT GGTCGTAAGA CCTGTATTCT GTTCCTGGTT TTCTTGGGAA 17880

ATCTCTGATA CATCTGGCCG TGGAGGTTCT ATAAAACTCT AAGAGCCGAG CAAGCTTCAC 17940

AGGAGGTAAA AAATTGGATG ACAGAAACCT TGTTGGTCCA AAATGCGAAC CCAGATTGTA 18000

AGACTATTTT AAAAGCATTG GGACCAAAGA TATTTTGAGA TTCTCGGCTC GTTCGAAGTG 18060

-continued

```
TCCTCCATTT TTTAACCTAC TGTCTTTGGA ACAACCAGGT TTTACGCTTG GGTCTAACAT  18120
TCTGATAAAA TTTTCGTAAC CCTGGTTAAT TACTAGGAGG GCGGCTACAC TAGAAGAAAT  18180
GATGACAGCA TGTCAGGGAG TAGGAGGACC CGGCCATAAG GCAAGAGTTT TGGCTGAAGC  18240
AATGAGCCAA GTAACAAATT CAGCTACCAT AATGATGCAG CGCCGATGTG ATCTTCTTTA  18300
CTACTGTCGT ACAGTCCCTC ATCCTCCTGG GCCGGTATTC CGTTCTCAAA ACCGACTTCG  18360
TTACTCGGTT CATTGTTTAA GTCGATGGTA TTACTACGTC AATTACGGGG AAATATGAGG  18420
AGAGGCAATT TTAGGAACCA AAGAAAGATT GTTAAGTGTT TCAATTGTGG CAAAGAAGGG  18480
CACACAGCCA GAAATTGCAG GGCCCCTAGG AAAAAGGGCT GTTGGAAATG TGGAAAGGAA  18540
TCTCCGTTAA AATCCTTGGT TTCTTTCTAA CAATTCACAA AGTTAACACC GTTTCTTCCC  18600
GTGTGTCGGT CTTTAACGTC CCGGGGATCC TTTTTCCCGA CAACCTTTAC ACCTTTCCTT  18660
GCCGGTACAG CCGGAGGGGA CACCAAATGA AAGATTGTAC TGAGAGACAG GCTAATTTTT  18720
TAGGGAAGAT CTGGCCTTCC TACAAGGGAA GGCCAGGGAA TTTTCTTCAG AGCAGACCAG  18780
AGCCAACAGC CCCACCACCT GTGGTTTACT TTCTAACATG ACTCTCTGTC CGATTAAAAA  18840
ATCCCTTCTA GACCGGAAGG ATGTTCCCTT CCGGTCCCTT AAAAGAAGTC TCGTCTGGTC  18900
TCGGTTGTCG GGGTGGTGCT AGGGTAGAGG GAAGAGAGCT TCAGGTCTGG GGTAGAGACA  18960
ACAACTCCCC CTCAGAAGCA GGAGCCGATA GACAAGGAAC TGTATCCTTT AACTTCCCTC  19020
AGATCACTCT TTGGCAACGA CCCCTCGTCA CTTCTCTCGA AGTCCAGACC CCATCTCTGT  19080
TGTTGAGGGG GAGTCTTCGT CCTCGGCTAT CTGTTCCTTG ACATAGGAAA TTGAAGGGAG  19140
TCTAGTGAGA AACCGTTGCT GGGGAGCAGT GTTTTGTGAG GCAATAAAGA TAGGGGGGCA  19200
ACTAAAGGAA GCTCTATTAG ATACAGGAGC AGATGATACA GTATTAGAAG AAATGAGTTT  19260
GCCAGGAAGA TGGAAACCAA AAATGATAGG GGGAATTGGA GGTTATTTCT ATCCCCCCGT  19320
TGATTTCCTT CGAGATAATC TATGTCCTCG TCTACTATGT CATAATCTTC TTTACTCAAA  19380
CGGTCCTTCT ACCTTTGGTT TTTACTATCC CCCTTAACCT CTGGATGATG GGGGAGGGTT  19440
TTATCAAAGT AAGACAGTAT GATCAGATAC TCATAGAAAT CTGTGGACAT AAAGCTATAG  19500
GTACAGTATT AGTAGGACCT ACACCTGTCA ACATAATTGG AAGAAATCTG TTGACTCCAA  19560
AATAGTTTCA TTCTGTCATA CTAGTCTATG AGTATCTTTA GACACCTGTA TTTCGATATC  19620
CATGTCATAA TCATCCTGGA TGTGGACAGT TGTATTAACC TTCTTTAGAC AACTGAGGCG  19680
AGTGTGTGAG GAGATTGGTT GCACTTTAAA TTTTTAACCC GGGGGATCCC GATTTTTATG  19740
ACTAGTTAAT CAAATAAAAA GCATACAAGC TATTGCTTCT CTAACCAACG TGAAATTTAA  19800
AAATTGGGCC CCCTAGGGCT AAAAATACTG ATCAATTAGT TTATTTTTCG TATGTTCGAT  19860
AACGAAGGCT CAGAGAG                                                 19877
```

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
GAAATAGTTA GCGTCAAC                                                18
```

(2) INFORMATION FOR SEQ ID NO:10:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

TGTCTAATGT GTTGAAGAAA AGATCATACA AGTTATAC 38

(2) INFORMATION FOR SEQ ID NO:11:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

AACTTGTATG ATCTTTTCTT CAACACATTA GACATGTATT TAC 43

(2) INFORMATION FOR SEQ ID NO:12:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

TAAGTTTGTA TCGTAATGGA CTCTAAAGAG ACTATTC 37

(2) INFORMATION FOR SEQ ID NO:13:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

AGTCTCTTTA GAGTCCATTA CGATACAAAC TTAAC 35

(2) INFORMATION FOR SEQ ID NO:14:

(i) SEQUENCE CHARACTERISTICS:
(A) LENGTH: 82 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

CCGACGATTT TAAAACGCCA CCGTCAGGGA AAGTTTCATA AGAAGCACCG GAAGAGAAGA 60

GAATTCTCGG GACAATTGGA TC 82

(2) INFORMATION FOR SEQ ID NO:15:

(i) SEQUENCE CHARACTERISTICS:
(A) LENGTH: 81 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

GTCTAGCTGG TGCTGAGTTT CTACGTGAGT TGATTCGTCT CTTGCGTGCC TCTCGTGATC 60

CAATTGTCCC GAGATATTCT C 81

(2) INFORMATION FOR SEQ ID NO:16:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

GTAGAAACTC AGCACCAGCT AGACAAGCTT CTTTATTCTA TACTTAAAAA GTGAAAATAA 60

ATAC 64

(2) INFORMATION FOR SEQ ID NO:17:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

ACTACTAATT AGCTATAAAA ACCCGGGATT AGTTTTTATT ACTAACTAAT TACTATACTG 60

(2) INFORMATION FOR SEQ ID NO:18:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

ATCATCGGAT CCTTTAATAA TCTTATGAAC TTTTATAAAT ATGAG 45

(2) INFORMATION FOR SEQ ID NO:19:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

ATCATCGAAG AGCTTCCGCT ATCTGCATTA AAGTTT 36

(2) INFORMATION FOR SEQ ID NO:20:

(i) SEQUENCE CHARACTERISTICS:
(A) LENGTH: 42 base pairs
(B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:20:

ATCATCCCCG GGAAGCTTTT AGTTATTGAA ATTAATCATA TA 42

(2) INFORMATION FOR SEQ ID NO:21:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

CATCATGAGC TCACTTATTA CATCCTACT 29

(2) INFORMATION FOR SEQ ID NO:22:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

TACTACGGTA CCTTTAATAA GCAATCACT 29

(2) INFORMATION FOR SEQ ID NO:23:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

CCCTCTAGAT CGCGATATCC GTTAAGTTTG TATCGTAATG CTTGCATTTT GTTATTCGT 59

(2) INFORMATION FOR SEQ ID NO:24:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

CCCGAATTCA TAAAAATTAT TGATGTCTAC A 31

(2) INFORMATION FOR SEQ ID NO:25:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:25:

GGCCGCGTCG ACATGCA 17

(2) INFORMATION FOR SEQ ID NO:26:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

TGTCGACGC 9

(2) INFORMATION FOR SEQ ID NO:27:

(i) SEQUENCE CHARACTERISTICS:
(A) LENGTH: 55 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

TTTCATTATC GCGATATCCG TTAAGTTTGT ATCGTAATGT CCACTCGTGG CGATC 55

(2) INFORMATION FOR SEQ ID NO:28:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

GGAGGGTTTC AGAGGCAG 18

(2) INFORMATION FOR SEQ ID NO:29:

(i) SEQUENCE CHARACTERISTICS:
(A) LENGTH: 58 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

CCCCTCGAGT CGCGATATCC GTTAAGTTTG TATCGTAATG CCACTAACAG AAGAAGCA 58

(2) INFORMATION FOR SEQ ID NO:30:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:30:

AAATCTCCAC TCCATCCTTG TTTTCAGATT TTTAAA 36

(2) INFORMATION FOR SEQ ID NO:31:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:31:

AATCTGAAAA CAGGAATGGA GTGGAGATTT GATTCT 36

(2) INFORMATION FOR SEQ ID NO:32:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:32:

CCCAAGCTTA CAATTTTTAA AATATTCAGG 30

(2) INFORMATION FOR SEQ ID NO:33:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

CCCAAGCTTA TGGCAATATT CCAAAGTAGC 30

(2) INFORMATION FOR SEQ ID NO:34:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

TGGAAAACCT ACCATGGTTG TAAGTCCCCA CCTCAA 36

(2) INFORMATION FOR SEQ ID NO:35:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

TGGGGACTTA CAACCATGGT AGGTTTTCCA GTAACA 36

(2) INFORMATION FOR SEQ ID NO:36:

(i) SEQUENCE CHARACTERISTICS:
(A) LENGTH: 36 base pairs
(B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:36:

TACAGTCTCA ATCATTGGTA CTAGCTTGTA GCACCA 36

(2) INFORMATION FOR SEQ ID NO:37:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

TACAAGCTAG TACCAATGAT TGAGACTGTA CCAGTA 36

(2) INFORMATION FOR SEQ ID NO:38:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

CCCCCTGCAG AAAAATTAAG GCCCAATTTT TGAAAT 36

(2) INFORMATION FOR SEQ ID NO:39:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

TAGGAAGATA CGTATTATTT TATAC 25

(2) INFORMATION FOR SEQ ID NO:40:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

ATCCCATTAT GAAAGCTTAT AG 22

(2) INFORMATION FOR SEQ ID NO:41:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:41:

CTCGAGCTGC AGGATATCAT CGATGGATCC TTTTTATAGC TAATTAGTCA CGTACCTTTA 60

TCATTAGTAA CAAAT 75

(2) INFORMATION FOR SEQ ID NO:42:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

GGATCCATCG ATGATATCCT GCAGCTCGAG TTTTTATGAC TAGTTAATCA CGGCCGCTCA 60

ATATTGTATT GGATGGTTAG 80

(2) INFORMATION FOR SEQ ID NO:43:

(i) SEQUENCE CHARACTERISTICS:
(A) LENGTH: 280 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:43:

```
Met Pro Leu Thr Glu Glu Ala Glu Leu Glu Leu Ala Glu Asn Arg Glu
1               5                   10                  15

Ile Leu Lys Glu Pro Val His Gly Val Tyr Tyr Asp Pro Ser Lys Asp
            20                  25                  30

Leu Ile Ala Glu Ile Gln Lys Gln Gly Gln Gly Gln Trp Thr Tyr Gln
        35                  40                  45

Ile Tyr Gln Glu Pro Phe Lys Asn Leu Lys Thr Gly Met Glu Trp Arg
    50                  55                  60

Phe Asp Ser Arg Leu Ala Phe His His Val Ala Arg Glu Leu His Pro
65                  70                  75                  80

Glu Tyr Phe Lys Asn Cys Lys Leu Met Ala Ile Phe Gln Ser Ser Met
                85                  90                  95

Thr Lys Ile Leu Glu Pro Phe Arg Lys Gln Asn Pro Asp Ile Val Ile
            100                 105                 110

Tyr Gln Tyr Met Asp Asp Leu Tyr Val Gly Ser Asp Leu Glu Ile Gly
        115                 120                 125

Gln His Arg Thr Lys Ile Glu Glu Leu Arg Gln His Leu Leu Arg Trp
    130                 135                 140

Gly Leu Thr Thr Met Val Gly Phe Pro Val Thr Pro Gln Val Pro Leu
145                 150                 155                 160

Arg Pro Met Thr Tyr Lys Ala Ala Val Asp Leu Ser His Phe Leu Lys
                165                 170                 175

Glu Lys Gly Gly Leu Glu Gly Leu Ile His Ser Gln Arg Arg Gln Asp
            180                 185                 190

Ile Leu Asp Leu Trp Ile Tyr His Thr Gln Gly Tyr Phe Pro Asp Trp
        195                 200                 205

Gln Asn Tyr Thr Pro Gly Pro Gly Val Arg Tyr Pro Leu Thr Phe Gly
    210                 215                 220

Trp Cys Tyr Lys Leu Val Pro Met Ile Glu Thr Val Pro Val Lys Leu
225                 230                 235                 240
```

```
Lys Pro Gly Met Asp Gly Pro Lys Val Lys Gln Trp Pro Leu Thr Glu
            245                 250                 255

Glu Lys Ile Lys Ala Leu Val Glu Ile Cys Thr Glu Met Glu Lys Glu
            260                 265                 270

Gly Lys Ile Ser Lys Ile Gly Pro
        275                 280
```

(2) INFORMATION FOR SEQ ID NO:44:

(i) SEQUENCE CHARACTERISTICS:
(A) LENGTH: 550 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:44:

```
Gly Gln Arg Val Arg Asn Val Val Ser Leu Val Ala Phe Val Ile Arg
1               5                   10                  15

Leu Gly Val Leu Gly Gly Val Ile Met Ile Phe Leu Arg Lys Glu Arg
            20                  25                  30

Gln Val Val Arg Arg Lys Ala Lys Thr Pro Ala Val Gly Leu Pro Glu
        35                  40                  45

Ile Thr Val Val Lys Tyr Lys Tyr Leu Glu Ser Arg Trp Asn Asp Arg
    50                  55                  60

Met Asp Gly Gly Gly Pro Arg Phe Ile Glu Thr Asp Asn Thr Asp Thr
65                  70                  75                  80

Asp Lys Gly Gly Asp Arg Thr Leu Leu Leu Gly Thr Ile Asn Ser Ser
                85                  90                  95

Cys Arg Ile Gln Gly Glu Ile Pro Pro Ala Tyr Ile Ala Lys Gly Val
            100                 105                 110

Glu Gln Trp Met Asn Ile Ile Gln Lys Ile Lys Cys Gln Leu Thr Ile
        115                 120                 125

Asn Asn Asn Ser Gly Thr Thr Asn Asn Trp Thr Asn Asn Gly Asn Trp
    130                 135                 140

Thr Ser Asn Phe Leu Pro Ser Ser Asn Cys Tyr Phe Phe Glu Gly Gly
145                 150                 155                 160

Cys Asn Phe Ser His Met Val Ile Glu Pro Asp Gly Gly Ser Ser Gln
                165                 170                 175

Asn Phe Val Ile Thr Lys Asn Lys Phe Gln Glu Lys Leu Lys Ser Val
            180                 185                 190

Ile Gln Arg Leu Thr Asp Asn Trp Lys Ala Arg Ser Ile Asn Cys His
        195                 200                 205

Ala Gln Arg Ile Thr Gly Ile Ile Asn Lys Thr Thr Tyr Phe Ala Arg
    210                 215                 220

Gly Pro Gly Ile His Ile Arg Lys Arg Lys Asn Tyr Asn Pro Arg Thr
225                 230                 235                 240

Cys Asn Ile Gln Val Ser Glu Asn Leu His Val Ile Ile Thr Lys Ala
                245                 250                 255

Asn Asp Asn Phe Asn Glu Ser Arg Ile Val Val Glu Glu Glu Ala Leu
            260                 265                 270

Ser Gly Asn Leu Leu Leu Gln Thr Ser Val Val Pro Arg Ile Gly His
        275                 280                 285

Thr Cys Gln Val Thr Ser Val Asn Lys Cys Ser Gly Lys Gly Ser Phe
    290                 295                 300
```

```
Lys Lys Asp Asn Cys Lys Leu Ile Ala Phe Gly Ala Pro Ala Cys Tyr
305                 310                 315                 320

His Ile Pro Ile Pro Glu Phe Ser Ile Lys Pro Cys Ala Gln Thr Ile
                325                 330                 335

Val Ser Thr Asn Cys Ser Ile Leu Arg Tyr Ser Thr Ser Asp Asn Asn
            340                 345                 350

Ile Ser Val Ile Asp Leu Lys Tyr Leu Leu Ala Tyr Glu Lys Gln Met
        355                 360                 365

Lys Asp Arg Ile Ser Thr Thr Ile Asn Phe Ser Cys Asn Lys Met Glu
    370                 375                 380

Gly Gly Lys Ile Thr Gly Glu Ser Asn Ser Asn Asn Asn Ala Thr Ser
385                 390                 395                 400

Asn Asn Thr Asn Thr Thr Asn Arg Leu Asp Thr Cys Asn Leu Thr Val
                405                 410                 415

Cys Leu Pro Thr Leu Lys Val Cys Pro Lys Leu Ser Gln Asp Trp Leu
            420                 425                 430

Ser Ile Ile Asp Glu His Met Gln Glu Val Met Asn Asn Lys Trp Met
        435                 440                 445

Asn Phe Asn Glu Thr Val Asn Val Leu Glu Val Glu Gln Pro Asn Pro
    450                 455                 460

Asp Thr Pro Val Cys Ala His Thr Ala Trp Val Asn His Val Glu Thr
465                 470                 475                 480

Asp Tyr Ala Lys Ala Asp Ser Ala Cys Phe Leu Thr Thr Thr Ala Glu
                485                 490                 495

Lys Trp Val Pro Val Gly Tyr Tyr Val Thr Val Trp Leu Lys Glu Thr
            500                 505                 510

Ala Ser Cys Ile Met Leu Met Gly Leu Leu Met Thr Gly Trp Arg Trp
        515                 520                 525

Gly Trp Arg Trp Leu His Gln Tyr Lys Glu Lys Val Arg Met Ala Val
    530                 535                 540

Thr Lys Gln Glu Lys Met
545                 550
```

(2) INFORMATION FOR SEQ ID NO:45:

(i) SEQUENCE CHARACTERISTICS:
(A) LENGTH: 500 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:45:

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
```

-continued

```
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500
```

(2) INFORMATION FOR SEQ ID NO:46:

-continued (i) SEQUENCE CHARACTERISTICS:
(A) LENGTH: 99 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:46:

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

(2) INFORMATION FOR SEQ ID NO:47:

(i) SEQUENCE CHARACTERISTICS:
(A) LENGTH: 88 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:47:

```
Gln His Arg Cys Met Arg Lys Tyr Asn Val Asp Ile Tyr Gly Lys Thr
1               5                   10                  15

Tyr Asp Val Arg Ile Val Lys Val Lys Val Thr Lys Gly Val Leu Lys
            20                  25                  30

Asp Arg Tyr Glu Val Tyr Arg Asp Met His Met Lys Val Ser Glu Ala
        35                  40                  45

Leu Ile Ala Glu Ser His Pro Tyr Asp Phe Leu Tyr Ile Tyr Leu Ala
    50                  55                  60

Tyr Asp Lys Glu Tyr Val Arg Gly Lys Ile Val Asp Gly Ala Asn Pro
65                  70                  75                  80

Leu Ser Tyr Cys Phe Ala Leu Met
                85
```

(2) INFORMATION FOR SEQ ID NO:48:

(i) SEQUENCE CHARACTERISTICS:
(A) LENGTH: 190 amino acids
(B) TYPE: amino acid
(C) STRANDEDNESS: Not Relevant
(D) TOPOLOGY: linear (ii) MOLECULE TYPE: amino acid (xi) SEQUENCE DESCRIPTION: SEQ ID NO:48:

```
Phe Arg Ile Ile Val Tyr Gly Leu Leu Lys Asp Val Ala Leu Lys Ala
1               5                   10                  15

Ala Asn Asn Lys Ala Asp Arg Lys Ser Lys Gly Asp Ala Lys Asp Phe
            20                  25                  30
```

-continued

```
Val Arg Gly Asp Ile Asp Val Cys Ala Tyr Phe Thr Pro Ser Asn Ser
        35                  40                  45

Pro Gly Val Ser Glu Ile Arg Phe Ser Trp Asp Arg Lys Thr Ile Gln
    50                  55                  60

Cys Tyr Glu Asn Ile Ile Thr Val Pro Asn Ala Asp Lys Trp Asp Ile
65                  70                  75                  80

Ile Lys Lys Ala Pro Ile Val Asp Asp Phe Ser Lys His Asp Glu Arg
                85                  90                  95

Met Ser Lys Glu Arg Ser Val Asp Asp Ile Ile Val Asp Ala Met Ala
            100                 105                 110

Asp Ala Asp Pro Lys Asp Ala Glu Thr Thr Met Phe Trp Arg Pro Pro
        115                 120                 125

Ile Asp Asp Ser Ser Tyr Val Met Ala Ser Arg Gln Leu Asp Tyr Leu
    130                 135                 140

Ala Lys Asn Val Glu Arg Lys Glu Met Asn Leu Gln Arg Thr Leu Gln
145                 150                 155                 160

Ala Ala Thr Ala Gly Glu Ile Gly Ile Asn Lys Ile Ala Ala Cys Val
                165                 170                 175

Ile Glu Ala Asp Ser Arg Glu Asp Ile Tyr Ile Lys Ser Met
            180                 185                 190
```